US011744263B2

(12) United States Patent
Haahr et al.

(10) Patent No.: US 11,744,263 B2
(45) Date of Patent: Sep. 5, 2023

(54) ANIMAL FEED ADDITIVES COMPRISING A POLYPEPTIDE HAVING PROTEASE ACTIVITY AND USES THEREOF

(71) Applicant: Novozymes A/S, Bagsvaerd (DK)

(72) Inventors: Laerke Tvedebrink Haahr, Bagsvaerd (DK); Tine Hoff, Holte (DK); Peter Rahbek Oestergaard, Virum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/630,156

(22) PCT Filed: Aug. 31, 2018

(86) PCT No.: PCT/EP2018/073529
§ 371 (c)(1),
(2) Date: Jan. 10, 2020

(87) PCT Pub. No.: WO2019/043191
PCT Pub. Date: Mar. 7, 2019

(65) Prior Publication Data
US 2020/0229463 A1    Jul. 23, 2020

(30) Foreign Application Priority Data

Sep. 1, 2017    (EP) .................................... 17189061

(51) Int. Cl.
| | | |
|---|---|---|
| *A23K 10/14* | (2016.01) | |
| *A23K 20/147* | (2016.01) | |
| *A23K 20/174* | (2016.01) | |
| *A23K 20/189* | (2016.01) | |
| *A23K 40/10* | (2016.01) | |
| *A23K 50/75* | (2016.01) | |
| *C12N 9/54* | (2006.01) | |
| *A23K 50/30* | (2016.01) | |
| *A23K 10/30* | (2016.01) | |

(52) U.S. Cl.
CPC ............ *A23K 10/14* (2016.05); *A23K 20/147* (2016.05); *A23K 20/174* (2016.05); *A23K 20/189* (2016.05); *A23K 40/10* (2016.05); *A23K 50/75* (2016.05); *C12N 9/54* (2013.01); *A23K 10/30* (2016.05); *A23K 50/30* (2016.05)

(58) Field of Classification Search
None
See application file for complete search history.

(56) References Cited

U.S. PATENT DOCUMENTS

| | | | | |
|---|---|---|---|---|
| 5,700,676 A | * | 12/1997 | Bott ........................ | C11D 3/386 |
| | | | | 435/220 |
| 7,157,416 B2 | * | 1/2007 | Becker ................ | C11D 3/38663 |
| | | | | 424/94.1 |
| 2001/0026797 A1 | * | 10/2001 | Sjoeholm ............... | A23K 10/30 |
| | | | | 426/54 |
| 2004/0209343 A1 | * | 10/2004 | Svendsen ................ | C12N 9/54 |
| | | | | 435/222 |
| 2011/0110910 A1 | * | 5/2011 | Svendsen .................. | A61P 1/00 |
| | | | | 424/94.2 |
| 2015/0329844 A1 | * | 11/2015 | Benie ............. | C12Y 304/21014 |
| | | | | 435/68.1 |
| 2016/0160159 A1 | * | 6/2016 | O'Connell ..... | C12Y 304/21062 |
| | | | | 435/219 |
| 2016/0208234 A1 | * | 7/2016 | Rasmussen .............. | C12N 9/54 |
| 2016/0298102 A1 | * | 10/2016 | Gjermansen ........... | C11D 3/386 |

FOREIGN PATENT DOCUMENTS

| | | | |
|---|---|---|---|
| JP | 2003521907 A | 7/2003 | |
| JP | 2004283034 A | 10/2004 | |
| JP | 2008301779 A | 12/2008 | |
| JP | 2008546395 A | 12/2008 | |
| WO | WO-9217577 A1 * | 10/1992 | ............. C11D 3/386 |
| WO | 2001/58275 A2 | 8/2001 | |
| WO | 2006/136160 A | 12/2006 | |
| WO | 2006/136160 A2 | 12/2006 | |
| WO | 2009/019157 A1 | 2/2009 | |
| WO | WO-2009019157 A1 * | 2/2009 | ............... C12N 9/54 |
| WO | 2015/014790 A2 | 2/2015 | |
| WO | 2015/024739 A2 | 2/2015 | |
| WO | WO-2015091990 A1 * | 6/2015 | ........... C12Y 304/00 |
| WO | 2015/197871 A1 | 12/2015 | |
| WO | 2016/071302 A1 | 5/2016 | |
| WO | 2016/097350 A1 | 6/2016 | |

OTHER PUBLICATIONS

Barrettetai., Perspectives in biochemistry and biophysics: Families and Clans of serine peptidases, Archives Biochem. Biophys. 318, 1995, 247-50. (Year: 1995).*
Uniprot, Accession No. P00780, 2015, www.uniprot.org. (Year: 2015).*
Uniprot, Accession No. P00782, 2016, www.uniport.org. (Year: 2016).*
Uniprot, Accessing No. A0A182DWC8, 2017, www.uniprot.org. (Year: 2015).*
Caine et al., Effect of protease treatment of soybean meal on content of total soluble matterand crude protein and level of soybean trypsin inhibitors, Animal Feed Sci. Technol. 71, 1998, 177-83. (Year: 1998).*
Marcu et al., The Influence of Genetics on Economic Efficiency of Broiler Chickens Growth, Animal Sci. Biotechnologies 46, 2013, 339-46. (Year: 2013).*
Uniprot, Accession No. A0A2N0ZEE9, 2018, www.uniprot.org. (Year: 2018).*
Smith, Using proteases in broiler diets, Int. Poultry Production 19, 2011, 15-17. (Year: 2011).*

(Continued)

*Primary Examiner* — Todd M Epstein
(74) *Attorney, Agent, or Firm* — Adam Rucker

(57) ABSTRACT

The present invention relates to animal feed or animal feed additives comprising polypeptides having protease activity and uses thereof. It also relates to the methods for producing the proteases and for using the proteases to improve animal performance and the nutritional value of an animal feed.

24 Claims, No Drawings
Specification includes a Sequence Listing.

(56) References Cited

OTHER PUBLICATIONS

Uniprot, Accession No. A0A182DWC8, 2018, www.uniprot.org. (Year: 2018).*
Scientific Opinion on the safety and efficacy of Cibenza® EP150, EFSA J. 13, 2015, 4055. (Year: 2015).*
Mauer et al., EBI Accession No. AWH23244 (2009).
Mauer et al., EBI Accession No. AWH23245 (2009).
Mauer et al., EBI Accession No. AWH23247 (2009).
Nielsen et al., EBI Accession No. BDB54575—(2016).
Nielsen et al., EBI Accession No. BDB54844—(2016).
Dohnalek et al; 2016, Understanding Enzymes Function Design Engineering and Analysis, pp. 203-265.
Dohnalek et al., Understanding Enzymes: Function, Design, Engineering, and Analysis, 2016, 203-265.
VASANTHA_2016_UniProt_Access_no_P00782.

* cited by examiner

SEQUENCE LISTING

<160> NUMBER OF SEQ ID NOS: 11

<210> SEQ ID NO 1
<211> LENGTH: 314
<212> TYPE: PRT
<213> ORGANISM: Bacillus horneckiae
<220> FEATURE:
<221> NAME/KEY: mat_peptide -continued

<222> LOCATION: (1)..(314)

<400> SEQUENCE: 1

Glu Val Thr Ala Thr Pro Ser Thr Gln Thr Pro Trp Gly Ile Lys Ser
1               5                   10                  15

Ile Tyr Asn Asp Gln Ser Ile Thr Lys Thr Thr Gly Gly Ser Gly Ile
            20                  25                  30

Lys Val Ala Val Leu Asp Thr Gly Val His Thr Gly His Ile Asp Leu
        35                  40                  45

Ala Gly Ser Ser Glu Gln Cys Lys Asp Phe Thr Gln Ser Asn Pro Leu
    50                  55                  60

Val Asn Gly Ser Cys Thr Asp Arg Gln Gly His Gly Thr His Val Ala
65                  70                  75                  80

Gly Thr Val Leu Ala His Gly Gly Ser Asp Gly Gln Gly Val Tyr Gly
                85                  90                  95

Val Ala Pro Gln Ala Lys Leu Trp Ala Tyr Lys Val Leu Gly Asp Asn
            100                 105                 110

Gly Ser Gly Tyr Ser Asp Asp Ile Ala Ala Ile Arg His Val Ala
        115                 120                 125

Asp Glu Ala Ser Arg Thr Gly Ser Lys Val Val Ile Asn Met Ser Leu
130                 135                 140

Gly Ser Ser Gly Lys Asp Ser Leu Ile Ala Ser Ala Val Asp Tyr Ala
145                 150                 155                 160

Tyr Gly Lys Gly Val Leu Ile Val Ala Ala Gly Asn Ser Gly Ser
                165                 170                 175

Gly Ser Asn Thr Ile Gly Tyr Pro Ala Ala Leu Val Asn Ala Val Ala
        180                 185                 190

Val Ala Ala Leu Glu Asn Val Gln Gln Asn Gly Thr Tyr Arg Val Ala
    195                 200                 205

Asn Phe Ser Ser Arg Gly Asn Pro Ala Thr Ala Gly Asp Phe Arg Ile
210                 215                 220

Gln Glu Arg Asp Val Glu Val Ser Ala Pro Gly Ala Ser Val Glu Ser
225                 230                 235                 240

Thr Trp Tyr Asn Gly Gly Tyr Asn Thr Ile Ser Gly Thr Ser Met Ala
                245                 250                 255

Thr Pro His Val Ala Gly Leu Ala Ala Lys Ile Trp Ser Ser Asn Ser
        260                 265                 270

Ser Leu Ser His Ser Gln Leu Arg Thr Glu Leu Gln Asn Arg Ala Lys
    275                 280                 285

Val Tyr Asp Ile Lys Gly Gly Ile Gly Ala Gly Thr Gly Asp Asp Tyr
290                 295                 300

Ala Ser Gly Phe Gly Tyr Pro Arg Val Lys
305                 310

<210> SEQ ID NO 2
<211> LENGTH: 311
<212> TYPE: PRT
<213> ORGANISM: Bacillus sp.
<220> FEATURE:
<221> NAME/KEY: mat_peptide
<222> LOCATION: (1)..(311)

<400> SEQUENCE: 2

Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Ser Gly Ile Lys Val Ala

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
 50                  55                  60

Ser Cys Thr Asp Arg Gln Gly His Gly Thr His Val Ala Gly Thr Val
 65                  70                  75                  80

Leu Ala His Gly Gly Ser Asn Gly Gln Gly Val Tyr Gly Val Ala Pro
                 85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
            115                 120                 125

Ser Arg Thr Gly Ser Lys Val Ile Asn Met Ser Leu Gly Ser Ser
            130                 135                 140

Ala Lys Asp Ser Leu Ile Ala Ser Ala Val Asp Tyr Ala Tyr Gly Lys
145                 150                 155                 160

Gly Val Leu Ile Val Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
            210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
            275                 280                 285

Ile Lys Gly Gly Ile Gly Ala Gly Thr Gly Asp Asp Tyr Ala Ser Gly
            290                 295                 300

Phe Gly Tyr Pro Arg Val Lys
305                 310

<210> SEQ ID NO 3
<211> LENGTH: 311
<212> TYPE: PRT
<213> ORGANISM: Artificial Sequence
<220> FEATURE:
<223> OTHER INFORMATION: Protein Engineered variant
<220> FEATURE:
<221> NAME/KEY: mat_peptide
<222> LOCATION: (1)..(311)

<400> SEQUENCE: 3

Ala Val Pro Ser Thr Gln Thr Pro Trp Gly Ile Lys Ser Ile Tyr Asn
1               5                   10                  15

Asp Gln Ser Ile Thr Lys Thr Gly Gly Lys Gly Ile Lys Val Ala
            20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly

```
                 50                  55                  60
Ser Cys Thr Asp Arg Gln Gly His Gly Thr His Val Ala Gly Thr Val
 65                  70                  75                  80

Leu Ala His Gly Gly Ser Asn Gly Gln Gly Val Tyr Gly Val Ala Pro
                 85                  90                  95

Gln Ala Lys Leu Trp Ala Tyr Lys Val Leu Gly Asp Lys Gly Glu Gly
                100                 105                 110

Tyr Ser Asp Asp Ile Ala Ala Ile Arg His Val Ala Asp Glu Ala
            115                 120                 125

Ser Arg Thr Gly Ser Lys Val Val Ile Asn Met Ser Leu Gly Ser Ser
130                 135                 140

Ala Lys Asp Ser Leu Ile Ala Ser Ala Val Asp Tyr Ala Tyr Gly Lys
145                 150                 155                 160

Gly Val Leu Ile Val Ala Ala Gly Asn Glu Gly Pro Lys Pro Asn
                165                 170                 175

Thr Ile Gly Tyr Pro Ala Gly Phe Val Asn Ala Val Ala Val Ala Ala
                180                 185                 190

Leu Glu Asn Val Gln Glu Lys Gly Thr Tyr Arg Val Ala Asp Phe Ser
                195                 200                 205

Ser Arg Gly Asn Pro Ala Thr Ala Gly Asp Tyr Ile Ile Gln Glu Arg
210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
                260                 265                 270

His Ser Gln Leu Arg Thr Glu Leu Gln Asn Arg Ala Lys Val Tyr Asp
                275                 280                 285

Ile Lys Gly Gly Ile Gly Ala Gly Pro Gly Asp Asp Tyr Ala Ser Gly
            290                 295                 300

Phe Gly Tyr Pro Arg Val Lys
305                 310

<210> SEQ ID NO 4
<211> LENGTH: 12
<212> TYPE: PRT
<213> ORGANISM: Artificial Sequence
<220> FEATURE:
<223> OTHER INFORMATION: Conserved motif TGXKV[I/V]XXMSLG.
<220> FEATURE:
<221> NAME/KEY: MISC_FEATURE
<222> LOCATION: (3)..(3)
<223> OTHER INFORMATION: The amino acid in position 3 is any amino acid.
<220> FEATURE:
<221> NAME/KEY: MISC_FEATURE
<222> LOCATION: (6)..(6)
<223> OTHER INFORMATION: The amino acid in position 3 is valine (V) or
      isoleucine (I).
<220> FEATURE:
<221> NAME/KEY: MISC_FEATURE
<222> LOCATION: (7)..(7)
<223> OTHER INFORMATION: The amino acid in position 7 is any amino acid.
<220> FEATURE:
<221> NAME/KEY: MISC_FEATURE
<222> LOCATION: (8)..(8)
<223> OTHER INFORMATION: The amino acid in position 8 is any amino acid.

<400> SEQUENCE: 4

Thr Gly Xaa Lys Val Xaa Xaa Xaa Met Ser Leu Gly
 1               5                  10
```

```
<210> SEQ ID NO 5
<211> LENGTH: 418
<212> TYPE: PRT
<213> ORGANISM: Bacillus sp-13380
<220> FEATURE:
<221> NAME/KEY: PEPTIDE
<222> LOCATION: (1)..(418)
<223> OTHER INFORMATION: Signal peptide: Residues 1-27

<400> SEQUENCE: 5

Met Lys Lys Lys Arg Ile Ile Gly Ser Ala Val Leu Ser Val Ala Met
 1               5                  10                  15

Gly Leu Ser Val Phe Ala Ser Gly Ala Phe Gly Gln Gln Val Glu Ser
            20                  25                  30

Asn Glu Thr Tyr Arg Val Val Ile Gln Gly Pro Ser Ala Glu Lys Ala
        35                  40                  45

Lys Ala Lys Ser Asn Tyr Gly Val Arg Trp Asp Phe Gly Gln Lys Gly
    50                  55                  60

Phe Thr Thr Thr Val Asn Ala Lys Gln Tyr Gln Ala Leu Leu Lys Asn
65                  70                  75                  80

Lys Asn Leu Lys Ile Asp Arg Val Asp Glu Val Lys Asn Ala Pro Val
                85                  90                  95

Thr Ala Ala Lys Pro Gly Ser Gly Ala Ala Ser Ala Pro Ala Asp Gly
            100                 105                 110

Thr Pro Trp Gly Ile Glu Ala Ile Tyr Asn Asp Ser Ser Ile Gln Ser
        115                 120                 125

Thr Ser Gly Gly Asn Gly Val Lys Val Ala Val Leu Asp Thr Gly Val
130                 135                 140

Asn Thr Ala His Ala Asp Leu Ala Gly Gln Ala Glu Gln Cys Lys Asp
145                 150                 155                 160

Phe Thr Gln Arg Lys Thr Pro Leu Ile Asp Gly Ser Cys Gly Asp Lys
                165                 170                 175

Asn Gly His Gly Thr His Val Ala Gly Thr Val Leu Ala His Gly Gly
            180                 185                 190

Ala Asn Gly Gln Gly Val Tyr Gly Val Ala Pro Asp Ala Asp Leu Trp
        195                 200                 205

Ala Tyr Lys Val Leu Asn Asp Arg Gly Ser Gly Tyr Ser Asp Asp Ile
    210                 215                 220

Ala Gly Ala Ile Lys His Ala Ala Asp Glu Ala Val Arg Thr Gly Ser
225                 230                 235                 240

Lys Val Val Ile Ser Met Ser Leu Gly Ser Ser Lys Ser Thr Leu
                245                 250                 255

Ile Ala Asp Ala Val Asp Tyr Ala Tyr Ser Lys Gly Val Leu Val Val
            260                 265                 270

Ala Ala Ala Gly Asn Asp Gly Pro Ala Asp Asn Thr Ile Gly Tyr Pro
        275                 280                 285

Gly Ala Leu Val Asn Ala Val Ala Val Ala Ala Leu Glu Asn Val Gln
    290                 295                 300

Gln Asn Gly Ser Tyr Arg Val Ala Asp Phe Ser Ser Arg Gly Asn Pro
305                 310                 315                 320

Ala Thr Asp Gly Asp Phe Val Ile Gln Glu Arg Asp Val Glu Val Ser
                325                 330                 335

Ala Pro Gly Arg Ala Ile Glu Ser Thr Trp Tyr Asp Gly Ser Tyr Ser
            340                 345                 350
```

Thr Ile Ser Gly Thr Ser Met Ala Thr Pro His Val Ser Gly Leu Ala
            355                 360                 365

Ala Lys Ile Trp Ala Gln Asn Pro Ser Met Ser His Thr Gln Leu Arg
370                 375                 380

Ala Glu Leu Gln Ser Arg Ala Lys Gln Asn Asp Ile Leu Gly Gly Thr
385                 390                 395                 400

Gly Ala Ala Ala Gly Asp Asp Tyr Ala Ser Gly Phe Gly Phe Pro Arg
                405                 410                 415

Val Lys

<210> SEQ ID NO 6
<211> LENGTH: 417
<212> TYPE: PRT
<213> ORGANISM: Bacillus idriensis
<220> FEATURE:
<221> NAME/KEY: PEPTIDE
<222> LOCATION: (1)..(417)
<223> OTHER INFORMATION: Signal peptide: Residues 1-27

<400> SEQUENCE: 6

Met Lys Ile Arg Lys Val Leu Gly Val Ala Val Leu Ser Leu Ser Met
1               5                   10                  15

Ser Leu Ser Met Phe Gly Thr Asn Thr Phe Ala Gln Asp Ala Ala Lys
            20                  25                  30

Thr Asp Val Asn Gln Asp Ser Ile Arg Val Val Ile Lys Gly Thr Asp
        35                  40                  45

Thr Glu Lys Val Lys Met Lys Lys Ser His Lys Val Arg Arg Asp Phe
50                  55                  60

Gly Lys Asp Gly Phe Thr Thr Thr Val Asn Ala Lys Glu Tyr Glu Ala
65                  70                  75                  80

Leu Ile Lys Asn Asp Lys Ile Lys Val Glu Lys Val Ser Thr Leu Gln
                85                  90                  95

Val Ala Ala Gly Lys Pro Ile Lys Thr Met Ala Leu Pro Ser Thr Arg
            100                 105                 110

Thr Pro Trp Gly Ile Lys Ala Ile Tyr Asn Asn Ser Ser Leu Thr Ser
        115                 120                 125

Thr Ser Gly Gly Asp Gly Ile Lys Ile Ala Val Leu Asp Thr Gly Val
130                 135                 140

Gln Thr Ser His Ile Asp Leu Ser Gln Asn Val Glu Gln Cys Lys Asp
145                 150                 155                 160

Phe Thr Val Gly Ser Ser Tyr Thr Asn Gly Ser Cys Thr Asp Arg Asn
                165                 170                 175

Gly His Gly Thr His Val Ala Gly Thr Ala Leu Ala Asn Gly Gly Ser
            180                 185                 190

Asp Gly Met Gly Ile Tyr Gly Val Ala Pro Gln Ser Glu Leu Trp Ala
        195                 200                 205

Tyr Lys Val Leu Thr Asp Ser Gly Ser Gly Tyr Ser Asp Asp Ile Ala
210                 215                 220

Ala Ala Ile Arg His Ala Ala Asp Glu Gly Thr Arg Thr Gly Ser Lys
225                 230                 235                 240

Val Ile Ile Ser Met Ser Leu Gly Ser Ser Gly Lys Asp Ser Leu Ile
                245                 250                 255

Ala Ser Ala Val Asp Tyr Ala Tyr Gly Lys Gly Ala Leu Val Ile Ala
            260                 265                 270

Ala Ala Gly Asn Ser Gly Ser Gly Asn Asn Thr Ile Gly Tyr Pro Gly
        275                 280                 285

```
Ala Leu Val Asn Ala Val Ala Val Ala Leu Glu Asn Val Gln Gln
    290                 295                 300

Asn Gly Thr Tyr Arg Val Ala Asn Phe Ser Ser Arg Gly Asn Ser Ala
305                 310                 315                 320

Thr Asp Gly Asp Phe Ile Ile Gly Glu Arg Asp Val Glu Ile Ser Ala
                325                 330                 335

Pro Gly Ala Ser Ile Glu Ser Thr Trp Ile Asn Ser Gly Tyr Asn Thr
                340                 345                 350

Ile Ser Gly Thr Ser Met Ala Thr Pro His Val Ser Gly Leu Ala Ala
            355                 360                 365

Lys Ile Trp Ser Ser Asn Lys Ser Gln Ser Asn Val Gln Val Arg Ala
        370                 375                 380

Glu Leu Gln Asn Arg Ala Lys Leu Tyr Asp Ile Lys Gly Gly Ile Gly
385                 390                 395                 400

Ala Ala Thr Gly Asp Asp His Ala Ser Gly Phe Gly Phe Ala Arg Val
                405                 410                 415

Gln

<210> SEQ ID NO 7
<211> LENGTH: 413
<212> TYPE: PRT
<213> ORGANISM: Bacillus sp
<220> FEATURE:
<221> NAME/KEY: PEPTIDE
<222> LOCATION: (1)..(413)
<223> OTHER INFORMATION: Signal peptide: Residues 1-27

<400> SEQUENCE: 7

Leu Leu Ser Met Thr Met Gly Leu Ser Val Phe Thr Ala Gly Ala Phe
1               5                   10                  15

Ala Lys Glu Pro Glu Thr Gln Asn Glu Thr Tyr Arg Val Leu Ile Gln
                20                  25                  30

Gly Pro Ala Asn Ala Lys Ala Ser Val Asn Ser Gln Val Asp Lys Arg
            35                  40                  45

Trp Asp Phe Gly Ser Asp Gly Met Thr Ala Glu Val Asn Ala Lys Gln
50                  55                  60

Tyr Gln Ala Leu Leu Lys Asn Lys Asn Leu Lys Ile Glu Lys Val Ser
65                  70                  75                  80

Glu Val Thr Leu Asp Thr Ala Arg Thr Glu Ala Ser Lys Lys Asp Ser
                85                  90                  95

Val Ser Ile Gln Ala Ala Gly Tyr Pro Ser Asp Gln Thr Pro Trp Gly
            100                 105                 110

Ile Ala Ser Ile Tyr Asn Asn Ser Ser Ile Thr Ser Thr Ser Gly Gly
        115                 120                 125

Ser Gly Ile Lys Val Ala Val Leu Asp Thr Gly Val Tyr Thr Gly His
    130                 135                 140

Ile Asp Leu Glu Gly Ser Ala Glu Gln Cys Lys Asp Phe Thr Gln Ser
145                 150                 155                 160

Thr Pro Leu Val Asn Gly Ser Cys Thr Asp Arg Gln Gly His Gly Thr
                165                 170                 175

His Val Ala Gly Thr Val Leu Ala His Gly Gly Tyr Asp Gly Gln Gly
            180                 185                 190

Ile Tyr Gly Val Ala Pro Gln Ala Lys Leu Trp Ala Tyr Lys Val Leu
        195                 200                 205

Gly Asp Asn Gly Ser Gly Tyr Ser Asp Asp Ile Ala Gly Ala Ile Arg
```

```
                210               215               220
His Val Asp Glu Ala Ser Arg Thr Gly Ser Lys Val Val Ile Asn
225                 230                 235                 240

Met Ser Leu Gly Ser Ser Gly Lys Asp Ser Leu Ile Ser Ser Ala Val
                    245                 250                 255

Asp Tyr Ala Tyr Ser Lys Gly Val Leu Val Ala Ala Gly Asn
                260                 265                 270

Ser Gly Tyr Ser Ala Asn Thr Ile Gly Tyr Pro Gly Ala Leu Lys Asn
                275                 280                 285

Ala Ile Ala Val Ala Ala Leu Glu Asn Val Gln Gln Asn Gly Thr Tyr
290                 295                 300

Arg Val Ala Asn Phe Ser Ser Arg Gly Asn Pro Asn Thr Asp Gly Asp
305                 310                 315                 320

Tyr Ile Ile Gln Glu Lys Asp Val Glu Val Ser Ala Pro Gly Ala Ser
                    325                 330                 335

Ile Glu Ser Thr Trp Tyr Asn Gly Gly Tyr Asn Thr Ile Ser Gly Thr
                340                 345                 350

Ser Met Ala Thr Pro His Val Ala Gly Leu Ala Ala Lys Ile Trp Ser
                    355                 360                 365

Ser Ser Pro Ser Met Ser His Thr Gln Leu Arg Thr Glu Leu Gln Asn
                370                 375                 380

Arg Ala Lys Gln Tyr Asp Ile Lys Gly Tyr Gly Ala Ala Thr Gly
385                 390                 395                 400

Asp Asp Tyr Ala Ser Gly Phe Gly Tyr Pro Arg Val Lys
                    405                 410

<210> SEQ ID NO 8
<211> LENGTH: 420
<212> TYPE: PRT
<213> ORGANISM: Bacillus sp
<220> FEATURE:
<221> NAME/KEY: PEPTIDE
<222> LOCATION: (1)..(420)
<223> OTHER INFORMATION: Signal peptide: Residues 1-29

<400> SEQUENCE: 8

Met Thr Lys Lys Lys Thr Val Ala Ala Ala Leu Leu Ser Leu Thr Leu
1               5                   10                  15

Gly Met Ser Val Phe Thr Ser Gly Ile Ser Ala Gln Val Ser Asp Glu
                20                  25                  30

Ala Lys Gly Ser Glu Thr Tyr Arg Val Leu Ile Gln Ala Pro Ser Asn
                35                  40                  45

Ser Val Asn Ala Leu Glu Thr Lys Tyr Glu Lys Arg Trp Asp Phe Gly
50                  55                  60

Lys Glu Gly Phe Thr Ala Asp Val Asn Ala Lys Glu Leu Gln Thr Leu
65                  70                  75                  80

Gln Ala Thr Lys Asn Val Glu Val Gln Lys Val Asn Glu Met Ser Ile
                85                  90                  95

Ala Thr Val Thr Gly Glu Val Ser Lys Ala Glu Val Thr Ala Val Pro
                100                 105                 110

Ser Ser Gln Thr Pro Trp Gly Ile Lys Ser Ile Tyr Asn Asn Gln Ser
                115                 120                 125

Leu Thr Ala Thr Ser Gly Gly Asn Gly Ile Lys Val Ala Val Leu Asp
                130                 135                 140

Thr Gly Val Tyr Thr Asn His Ile Asp Leu Ala Gly Ser Ala Glu Gln
145                 150                 155                 160
```

```
Cys Lys Asp Phe Thr Gln Ser Ser Pro Leu Val Asn Gly Ser Cys Thr
                165                 170                 175

Asp Arg Gln Gly His Gly Thr His Val Ala Gly Thr Val Leu Ala His
            180                 185                 190

Gly Gly Ser Asp Gly Gln Gly Val Tyr Gly Val Ala Pro Asp Ala Lys
            195                 200                 205

Leu Trp Ala Tyr Lys Val Leu Gly Asp Asn Gly Ser Gly Tyr Ser Asp
    210                 215                 220

Asp Ile Ala Ala Ala Ile Arg His Val Ala Asp Gln Ala Thr Ser Thr
225                 230                 235                 240

Gly Ser Lys Val Val Ile Asn Met Ser Leu Gly Ser Ser Gly Lys Asp
                245                 250                 255

Ser Leu Ile Ser Ser Ala Val Asp Tyr Ala Tyr Asn Lys Gly Val Leu
            260                 265                 270

Val Val Ala Ala Ala Gly Asn Ser Gly Ser Gly Ser Asn Thr Ile Gly
    275                 280                 285

Tyr Pro Gly Ala Leu Val Asn Ala Val Ala Val Ala Ala Leu Glu Asn
        290                 295                 300

Val Gln Gln Asn Gly Thr Tyr Arg Val Ala Asn Phe Ser Ser Arg Gly
305                 310                 315                 320

Asn Pro Ser Thr Asp Gly Asp Tyr Val Ile Gln Glu Arg Asp Ile Glu
                325                 330                 335

Val Ser Ala Pro Gly Ala Ala Val Glu Ser Thr Trp Tyr Asn Gly Gly
            340                 345                 350

Tyr Asn Thr Ile Ser Gly Thr Ser Met Ala Thr Pro His Val Ala Gly
        355                 360                 365

Leu Ala Ala Lys Ile Trp Ala Ser Asn Pro Ser Trp Ser Lys Ser Thr
    370                 375                 380

Leu Arg Thr Glu Leu Gln Asn Arg Ala Lys Val Tyr Asp Ile Lys Gly
385                 390                 395                 400

Gly Val Gly Ala Thr Thr Gly Asp Asp Tyr Ala Ser Gly Phe Gly Tyr
                405                 410                 415

Pro Arg Val Lys
            420

<210> SEQ ID NO 9
<211> LENGTH: 425
<212> TYPE: PRT
<213> ORGANISM: Bacillus oceanisediminis
<220> FEATURE:
<221> NAME/KEY: PEPTIDE
<222> LOCATION: (1)..(425)
<223> OTHER INFORMATION: Signal peptide: Residues 1-25

<400> SEQUENCE: 9

Met Lys Lys Lys Arg Val Leu Gly Ala Ala Leu Leu Ser Met Thr Met
1               5                   10                  15

Gly Leu Ser Val Phe Thr Ala Gly Ala Phe Ala Lys Gly Pro Glu Ala
            20                  25                  30

Asn Glu Ser Tyr Arg Val Leu Ile Gln Gly Pro Ala Ala Glu Arg Ala
        35                  40                  45

Asn Val Lys Ala Gln Ile Glu Glu Arg Trp Asp Phe Gly Lys Asp Gly
    50                  55                  60

Leu Thr Ala Glu Val Asn Ser Lys Gln Tyr Gln Ala Leu Leu Lys Asn
65                  70                  75                  80
```

```
Lys Asn Ile Thr Ile Glu Lys Val Ser Glu Val Thr Leu Asp Thr Ala
                85                  90                  95
Arg Thr Glu Ala Ser Ser Lys Asn Asp Ser Ile Ser Leu Glu Ala
            100                 105                 110
Ala Gly Tyr Pro Ser Asp Gln Thr Pro Trp Gly Ile Glu Ser Ile Tyr
            115                 120                 125
Asn Asn Ser Tyr Ile Ser Ser Thr Ser Gly Gly Ser Gly Ile Lys Val
130                 135                 140
Ala Val Leu Asp Thr Gly Val Tyr Thr Asn His Ile Asp Leu Glu Gly
145                 150                 155                 160
Ser Ala Glu Gln Cys Lys Asp Phe Thr Gln Ser Tyr Ser Ser Met Val
                165                 170                 175
Asn Gly Thr Cys Thr Asp Arg Gln Gly His Gly Thr His Val Ala Gly
            180                 185                 190
Thr Val Leu Ala His Gly Gly Tyr Asp Gly Leu Gly Val Tyr Gly Val
            195                 200                 205
Ala Pro Gln Ala Lys Leu Trp Ala Tyr Lys Val Leu Gly Asp Asn Gly
            210                 215                 220
Ser Gly Tyr Ser Asp Asp Ile Ala Gly Ala Ile Arg His Val Ala Asp
225                 230                 235                 240
Glu Ala Val Arg Thr Gly Ser Lys Val Val Ile Asn Met Ser Leu Gly
                245                 250                 255
Ser Ser Gly Lys Asp Ser Leu Ile Ala Ser Ala Val Asp Tyr Ala Tyr
                260                 265                 270
Ser Lys Gly Val Leu Ile Val Ala Ala Ala Gly Asn Ser Gly Tyr Ser
            275                 280                 285
Ala Asn Thr Ile Gly Tyr Pro Gly Ala Leu Thr Asn Ala Ile Ala Val
            290                 295                 300
Ala Ala Leu Glu Asn Val Gln Gln Asn Gly Thr Tyr Arg Val Ala Asn
305                 310                 315                 320
Phe Ser Ser Arg Gly Asn Pro Asn Thr Asp Gly Asp Tyr Tyr Ile Gln
                325                 330                 335
Glu Arg Asp Val Glu Val Ser Ala Pro Gly Ala Ser Ile Glu Ser Thr
            340                 345                 350
Trp Tyr Asn Gly Gly Tyr Asn Thr Ile Ser Gly Thr Ser Met Ala Thr
            355                 360                 365
Pro His Val Ala Gly Leu Ala Ala Lys Ile Trp Ser Ser Asn Pro Tyr
            370                 375                 380
Met Ser His Thr Gln Leu Arg Thr Glu Leu Arg Asn Arg Ala Lys Gln
385                 390                 395                 400
Tyr Asp Ile Lys Gly Gly Tyr Gly Ala Ala Thr Gly Asp Asp Tyr Ala
                405                 410                 415
Ser Gly Phe Gly Tyr Pro Arg Val Arg
            420                 425

<210> SEQ ID NO 10
<211> LENGTH: 1278
<212> TYPE: DNA
<213> ORGANISM: Bacillus oceanisediminis

<400> SEQUENCE: 10
atgaagaaga agcgcgtact tggcgcagct cttctttcaa tgacaatggg cctttcagta    60
ttcacagctg gcgcatttgc taaaggtcct gaggctaacg agtcttaccg cgtacttatc   120
caaggacctg cggctgaacg cgctaacgtt aaagcccaaa tcgaggagcg ctgggacttt   180
```

```
ggtaaagacg gtcttacggc tgaggttaac tctaaacagt accaggctct tcttaagaac     240
aaaaacatca ctatcgagaa agtttcagag gttacgttag acacagctcg cactgaggct     300
tcatcaagca aaaacgactc aatctcactt gaggcagctg gctatccttc agaccaaact     360
ccttggggca tcgagtcaat ctacaacaac tcttacatct catcaacatc aggaggctca     420
ggtatcaaag ttgcagtttt agacactggc gtttacacaa accacatcga ccttgagggc     480
tctgcagagc agtgcaaaga ctttactcag tcttactcat caatggttaa cggtacgtgc     540
acagaccgcc agggccatgg cacacacgta gcaggcacag ttcttgcgca cggtggctac     600
gacggccttg gtgtatatgg cgttgcacct caagccaaac tttgggctta caaagttctt     660
ggcgacaacg gatcaggcta ttcagacgac atcgcaggcg ctatccgcca cgtagctgac     720
gaggctgttc gcacaggatc aaaagtagta atcaacatgt cacttggaag ctcaggtaaa     780
gactcactta tcgcgtcagc tgttgactat gcttattcaa aaggcgttct tatcgttgct     840
gcggctggta actcaggtta ttcagcaaac acaatcggct accctggtgc gcttacgaac     900
gcaatcgctg ttgccgctct tgagaacgta caacagaacg gcacttatcg cgttgcgaac     960
ttttcatcac gcggaaaccc taacacagac ggcgactact atatccagga gcgcgacgtt    1020
gaggtttcag ctcctggtgc ttcaatcgag tcaacgtggt acaatggtgg ctacaacact    1080
atctcaggca cgtcaatggc tacgcctcac gttgctggcc ttgctgcgaa aatctggtct    1140
tcaaaccctt acatgtcaca cactcaactt cgcactgagc ttcgcaatcg cgctaaacaa    1200
tacgacatca aagtggata tggagctgct actggtgacg actacgcatc aggttttggt     1260
tatcctcgcg ttcgctaa                                                 1278
```

```
<210> SEQ ID NO 11
<211> LENGTH: 27
<212> TYPE: PRT
<213> ORGANISM: Bacillus clausii
<220> FEATURE:
<221> NAME/KEY: PEPTIDE
<222> LOCATION: (1)..(27)
<223> OTHER INFORMATION: Signal peptide: Residues 1-27

<400> SEQUENCE: 11

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```

ANIMAL FEED ADDITIVES COMPRISING A POLYPEPTIDE HAVING PROTEASE ACTIVITY AND USES THEREOF

CROSS-REFERENCE TO RELATED APPLICATIONS

This application is a 35 U.S.C. 371 national application of international application no. PCT/EP2018/073529 filed Aug. 31, 2018, which claims priority or the benefit under 35 U.S.C. 119 of European application no. 17189061.9 filed Sep. 1, 2017. The content of each application is fully incorporated herein by reference.

REFERENCE TO A SEQUENCE LISTING

This application contains a Sequence Listing in computer readable form, which is incorporated herein by reference. The name of the file containing the Sequence Listing is Replacement_SQ_02_27_2023.txt, which was created on Feb. 27, 203, and has 30,073 bytes.

BACKGROUND OF THE INVENTION

Field of the Invention

The present invention relates to animal feed or animal feed additives comprising polypeptides having protease activity and uses thereof. It also relates to the methods for producing the proteases and for using the proteases to improve animal performance and the nutritional value of an animal feed.

Background of the Invention

In the use of proteases in animal feed (in vivo), and/or the use of such proteases for treating vegetable proteins (in vitro) it is noted that proteins are essential nutritional factors for animals and humans. Most livestock and many human beings get the necessary proteins from vegetable protein sources. Important vegetable protein sources are, e.g., oilseed crops, legumes and cereals.

When a protein source such as soybean meal is included in the feed of mono-gastric animals such as pigs and poultry, a significant proportion of the soybean meal is not digested efficiently (the apparent ileal nitrogen digestibility in piglets, growing pigs and poultry such as broilers, laying hens and roosters is only around 80%). By improving the digestibility of protein, the animal can uptake more of the protein thereby improving performance, such as increased body weight gain.

The gastrointestinal tract of animals consists of a series of segments each representing different pH environments. In mono-gastric animals such as pigs and poultry and many types of fish, the stomach is strongly acidic with a pH potentially as low as 2-3, while the intestine has a more neutral pH of around 6-7.5. Apart from the stomach and intestine, poultry also have a crop preceding the stomach. The pH in the crop is mostly determined by the feed ingested and hence typically lies in the range of pH 4-6. Protein digestion by a protease may occur along the entire digestive tract, provided that the protease is active and survives the conditions in the digestive tract. Hence, proteases which are highly acid stable that can survive in the gastric environment and at the same time are efficiently active at the broad range of physiological pH of the digestive tract in the target animal are especially desirable.

One way of determining whether a protease can improve the uptake of protein is by investigating whether the ileal nitrogen digestibility is improved when the protease is added to the animal diet. Running in vivo trials can both confirm the gastric stability of the protease as well as the effectiveness of the protease in degrading the protein. It is an objective of the present invention to provide proteases which show increased improved growth performance, such as by apparent ileal nitrogen digestibility.

SUMMARY OF THE INVENTION

The invention relates to an animal feed additive comprising one or more polypeptides having protease activity, wherein the polypeptide is an S8 protease selected from the group consisting of:

(a) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;

(b) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2;

(c) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;

(d) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;

(e) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;

(f) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6;

(g) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7;

(h) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8;

(i) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;

(j) a variant of SEQ ID NO: 1, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(k) a variant of SEQ ID NO: 2, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(l) a variant of SEQ ID NO: 3, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a variant of SEQ ID NO: 5, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(n) a variant of SEQ ID NO: 6, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(o) a variant of SEQ ID NO: 7, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(p) a variant of SEQ ID NO: 8, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(q) a variant of SEQ ID NO: 9, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(r) a polypeptide comprising the polypeptide of (a), (b), (c), (d), (e), (f), (g), (h), or (i) and an N-terminal and/or C-terminal His-tag and/or HQ-tag;

(s) a polypeptide comprising the polypeptide of (a), (b), (c), (d), (e), (f), (g), (h), or (i) and an N-terminal and/or C-terminal extension of up to 10 amino acids, e.g., 1, 2, 3, 4, 5, 6, 7, 8, 9 or 10 amino acids; and (t) a fragment of the polypeptide of (a), (b), (c), (d), (e), (f), (g), (h), or (i) having protease activity and having at least 90% of the length of the mature polypeptide.

The invention further relates to animal feed and liquid formulation comprising the animal feed additive; methods of improving one or more performance parameters of an animal; methods of preparing an animal feed; methods for the treatment of proteins; methods for increasing digestibility and/or solubility of protein and methods for improving the nutritional value of an animal feed using the animal feed additive and uses thereof. The present invention further relates to methods of producing a polypeptide of the invention in a recombinant *Bacillus* host cell.

The invention further relates to a use of the animal feed additive invention or the liquid formulation in the preparation of a composition for use in animal feed; for improving the nutritional value of an animal feed; for increasing digestible and/or soluble protein in animal feed; for increasing the degree of hydrolysis of proteins in animal diets; for improving one or more performance parameters in an animal; and/or for the treatment of proteins.

OVERVIEW OF SEQUENCE LISTING

SEQ ID NO: 1 is the amino acid sequence of the mature S8 protease from *Bacillus horneckiae*.

SEQ ID NO: 2 is the amino acid sequence of the mature S8 protease from *Bacillus* sp. TY145.

SEQ ID NO: 3 is the amino acid sequence of a variant S8 protease from *Bacillus* sp. TY145

SEQ ID NO: 4 is the conserved motif TGXK[V/T][I/V]X[N/S]MSLG.

SEQ ID NO: 5 is the amino acid sequence of the mature S8 protease from *Bacillus* sp. 13380 (also disclosed in WO2017064253) and has approximately 78% identity to SEQ ID NO: 1

SEQ ID NO: 6 is the amino acid sequence of the mature S8 protease from *Bacillus idriensis* (also disclosed in WO2015091989) and has 80% identity to SEQ ID NO: 1.

SEQ ID NO: 7 is the amino acid sequence of the mature S8 protease from *Bacillus* sp. 13380 (also disclosed in WO2015091989) and has 89% identity to SEQ ID NO: 1.

SEQ ID NO: 8 is the amino acid sequence of the mature S8 protease from *Bacillus* sp. 62451 (also disclosed in WO2015091989) and has 90% identity to SEQ ID NO: 1.

SEQ ID NO: 9 is the amino acid sequence of the mature S8 protease from *Bacillus oceanisediminis* and has 87% identity to SEQ ID NO: 1.

SEQ ID NO:10 The DNA sequence encoding the S8 proteases *Bacillus oceanisediminis*

Definitions

Activity of the polypeptide on soybean-maize meal: The term "activity of the polypeptide on soybean-maize meal" means that the protease activity of the enzyme was determined on soybean meal-maize meal mixed in a 30:70 ratio using the o-Phthaldialdehyde (OPA) assay as described herein. Examples of assay-pH-values are pH 3.0, 4.0, 5.0, 6.0 and 7.0. Examples of assay-temperatures are 30, 35, 40, 45 and 50° C. Examples of assay-times are 2, 3 and 4 hours. Examples of enzyme concentrations are 50, 100, 150, 200, 250 and 300 mg enzyme protein/kg dry matter of substrate.

In a preferred embodiment, the activity of the polypeptide on soybean-maize meal was determined by adding soybean meal-maize meal mixed in a 30:70 ratio (2 g) to buffers containing 100 mM succinic acid, 100 mM HEPES, 100 mM CHES, 100 mM CAPS, 12.5 mM $CaCl_2$), 150 mM KCl, 0.01% Triton X-100 (10 mL) that had been prepared and adjusted using HCl or NaOH to a pH value such that after soybean-maize meal substrate had been mixed with assay buffer, the final pH of the slurry was pH 3.0, 4.0, 5.0, 6.0 or 7.0; then mixing an aliquot of substrate slurry (2 mL) for 30 min at 40° C.; adding protease (200 mg enzyme protein/kg substrate) dissolved in 100 µl 100 mM sodium acetate buffer (9.565 g/L NaOAc, 1.75 g/L acetic acid, 5 mM $CaCl_2$), 0.01% BSA, 0.01% Tween20, pH 6.0); incubating the samples for 3 hours at 40° C. (magnetic stirring); centrifuging the samples (10 min, 4000 rpm, 0° C.); and collecting the supernatants for analysis using the o-Phthaldialdehyde (OPA) assay (herein called "soybean-maize meal assay"). In another preferred embodiment, the activity of the polypeptide on soybean-maize meal is determined as described in example 4 herein.

In an embodiment, the polypeptides of the present invention have at least 50%, e.g., at least 60%, at least 70%, at least 80%, at least 90%, at least 95%, or at least 100% of the activity on soybean-maize meal at pH 4 as the polypeptide of SEQ ID NO: 1.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Animal: The term "animal feed" refers to all animals except humans. Examples of animals are non-ruminants, and ruminants. Ruminant animals include, for example, animals such as sheep, goats, cattle, e.g., beef cattle, cows, and young calves, deer, yank, camel, llama and kangaroo. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, Java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Body Weight Gain: The term "body weight gain" means an increase in live weight of an animal during a given period of time, e.g., the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Composition: The term "composition" refers to a composition comprising a carrier and at least one enzyme of the present invention. The compositions described herein may be mixed with an animal feed and referred to as a "mash feed."

Concentrates: The term "concentrates" means feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean, rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

European Production Efficacy Factor (EPEF): The term "European Production Efficacy Factor" is one term which determines production efficiency and takes into account feed conversion, mortality and daily gain. EEF is calculated as [(survival rate (%)×body weight gain (kg))/(Study duration in days×FCR)]×100.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide having one or more (e.g., several) amino acids absent from the amino and/or carboxyl terminus of a mature polypeptide; wherein the fragment has protease activity.

In one aspect, the fragment comprises at least 90% of the length of the mature polypeptide, such as at least 283 amino acids of SEQ ID NO: 1, at least 279 amino acids of SEQ ID NO: 2 or at least 279 amino acids of SEQ ID NO: 3.

In one aspect, the fragment comprises at least 92% of the length of the mature polypeptide, such as at least 290 amino acids of SEQ ID NO: 1, at least 286 amino acids of SEQ ID NO: 2 or at least 286 amino acids of SEQ ID NO: 3.

In one aspect, the fragment comprises at least 94% of the length of the mature polypeptide, such as at least 295 amino acids of SEQ ID NO: 1, at least 292 amino acids of SEQ ID NO: 2 or at least 292 amino acids of SEQ ID NO: 3.

In one aspect, the fragment comprises at least 96% of the length of the mature polypeptide, such as at least 301 amino acids of SEQ ID NO: 1, at least 298 amino acids of SEQ ID NO: 2 or at least 298 amino acids of SEQ ID NO: 3.

In one aspect, the fragment comprises at least 98% of the length of the mature polypeptide, such as at least 308 amino acids of SEQ ID NO: 1, at least 304 amino acids of SEQ ID NO: 2 or at least 304 amino acids of SEQ ID NO: 3.

In one aspect, the fragment comprises at least 99% of the length of the mature polypeptide, such as at least 311 amino acids of SEQ ID NO: 1, at least 307 amino acids of SEQ ID NO: 2 or at least 307 amino acids of SEQ ID NO: 3.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Apparent ileal nitrogen digestibility: The term "apparent ileal nitrogen digestibility" (or AIDN) is the percentage difference in nitrogen concentration between ileal digesta and feed, when taking the apparent disappearance of dry matter at the end of the small intestine (ileum) into account. AIDN is used as an estimate of small intestine crude protein digestibility, without taking small intestine endogenous protein release into account. This means that the true digestibility of crude protein is always larger compared to the AIDN. An increased AIDN is in general correlated to an increased small intestine absorption of amino acids and is a marker of improved performance in animals. Apparent ileal nitrogen digestibility (AIDN) is calculated using the formula:

$$AIDN\ (\%)=100-[(CMf/CMe)\times(CNe/CNf)]\times 100;$$

wherein
$CMf$=concentration of marker in feed;
$CMe$=concentration of marker in ileal digesta;
$CNf$=concentration of nutrient in feed;
$CNe$=concentration of nutrient in ileal digesta.

The term "improves the ileal nitrogen digestibility by at least x % (e.g., 4%) compared to negative control" means that if the percentage apparent ileal nitrogen-digestibility for the negative control (i.e., the same feed but without a protease added to the diet) is y % (e.g., 75%), then the percentage apparent ileal nitrogen-digestibility for the group with the protease is at least y %+x % (so in this example >79%).

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 314 of SEQ ID NO: 1 based on EDMAN N-terminal sequencing data and intact MS data. In one aspect, the mature polypeptide is amino acids 1 to 311 of SEQ ID NO: 2 based on EDMAN N-terminal sequencing data and intact MS data. In one aspect, the mature polypeptide is amino acids 1 to 311 of SEQ ID NO: 3 based on EDMAN N-terminal sequencing data and intact MS data.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the order Bacillales wherein the term order is the taxonomic rank. In another preferred embodiment, the polypeptide is obtained or obtainable from the family Bacillaceae, Planococcaceae or Paenibacillaceae wherein the term family is the taxonomic rank. In another preferred embodiment, the polypeptide is obtained or obtainable from the genus *Bacillus*, wherein the term genus is the taxonomic rank.

If the taxonomic rank of a polypeptide is not known, it can easily be determined by a person skilled in the art by performing a BLASTP search of the polypeptide (using, e.g., the National Center for Biotechnology Information (NCIB) website—www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Performance parameters: the term "performance parameters" means one of more of the terms selected from the list consisting of body weight gain, European Production Efficiency Factor (EPEF), European Production Efficacy Factor (EFF) and FCR. The term "improving one or more performance parameters" means that there is an increase in body weight gain, an increase in European Production Efficiency Factor (EPEF), an increase in European Production Efficacy Factor (EFF) and/or a decrease in FCR in one or more animals.

Protease: The term "protease" is defined herein as an enzyme that hydrolyzes peptide bonds. It includes any enzyme belonging to the EC 3.4 enzyme group (including each of the thirteen subclasses thereof, en.wikipedia.org/wiki/Category:EC_3.4). The EC number refers to Enzyme Nomenclature 1992 from NC-IUBMB, Academic Press, San Diego, Calif., including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The term "subtilases" refer to a sub-group of serine protease according to Siezen et al., 1991, *Protein Engng.* 4: 719-737 and Siezen et al., 1997, *Protein Science* 6: 501-523. Serine proteases or serine peptidases is a subgroup of proteases characterized by having a serine in the active site, which forms a covalent adduct with the substrate. Further, the subtilases (and the serine proteases) are characterized by having two active site amino acid residues apart from the serine, namely a histidine and an aspartic acid residue. The subtilases may be divided into 6 sub-divisions, i.e., the Subtilisin family, the Thermitase family, the Proteinase K family, the Lantibiotic peptidase family, the Kexin family and the Pyrolysin family.

Protease activity: The term "protease activity" means proteolytic activity (EC 3.4). Polypeptides having protease activity, or proteases, are sometimes also designated peptidases, proteinases, peptide hydrolases, or proteolytic enzymes. Proteases may be of the exo-type that hydrolyze peptides starting at either end thereof, or of the endo-type that act internally in polypeptide chains (endopeptidases). Endopeptidases show activity on N- and C-terminally blocked peptide substrates that are relevant for the specificity of the protease in question.

There are several protease activity types such as trypsin-like proteases cleaving at the carboxyterminal side of Arg and Lys residues and chymotrypsin-like proteases cleaving at the carboxyterminal side of hydrophobic amino acid residues. Proteases of the invention are serine endopeptidases (EC 3.4.21) with a slightly alkaline pH-optimum (pH optimum 8-9.5).

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and hemoglobin. In the classical Anson and Mirsky method, denatured hemoglobin is used as substrate and after the assay incubation with the protease in question, the amount of trichloroacetic acid soluble hemoglobin is determined as a measurement of protease activity (Anson and Mirsky, 1932, *J. Gen. Physiol.* 16: 59 and Anson, 1938, *J. Gen. Physiol.* 22: 79).

For purposes of the present invention, protease activity was determined using assays which are described in "Materials and Methods", such as the Suc-AAPF-pNA assay and the Protazyme AK assay. For the Protazyme AK assay, insoluble Protazyme AK (Azurine-Crosslinked Casein) substrate liberates a blue color when incubated with the protease and the color is determined as a measurement of protease activity. For the Suc-AAPF-pNA assay, the colorless Suc-AAPF-pNA substrate liberates yellow paranitroaniline when incubated with the protease and the yellow color is determined as a measurement of protease activity.

The polypeptides of the present invention have at least 20%, e.g., at least 40%, at least 65%, at least 70%, at least 80%, at least 90%, at least 95%, and at least 100% of the protease activity of the polypeptide of SEQ ID NO: 1.

Roughage: The term "roughage" means dry plant material with high levels of fiber, such as fiber, bran, husks from seeds and grains and crop residues (such as stover, copra, straw, chaff, sugar beet waste).

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the—nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the—nobrief option) is used as the percent identity and is calculated as follows:

(Identical Deoxyribonucleotides×100)/(Length of
Alignment−Total Number of Gaps in Alignment)

Silage: The term "silage" means fermented, high-moisture stored fodder which can be fed to ruminants (cud-chewing animals such as cattle and sheep) or used as a biofuel feedstock for anaerobic digesters. It is fermented and stored in a process called ensilage, ensiling or silaging, and is usually made from grass or cereal crops (e.g., maize, sorghum, oats, rye, timothy, etc. forage grass plants), or legume crops like clovers/trefoils, alfalfa, vetches, using the entire green plant (not just the grain). Silage can be made from many field crops, and special terms may be used depending on type (oatlage for oats, haylage for alfalfa). Silage is made either by placing cut green vegetation in a silo, by piling it in a large heap covered with plastic sheet, or by wrapping large bales in plastic film.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 20%, e.g., at least 40%, at least 65%, at least 70%, at least 80%, at least 90%, at least 95%, or at least 100% of the protease activity of SEQ ID NO: 1.

Nomenclature

For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Animal Feed Additives Comprising Polypeptides Having Protease Activity

Proteases work by degrading protein into smaller fragments which are more easily digested and utilized by the animal. Animal diets mainly comprise a carbohydrate source (e.g., maize, wheat, rye) and a protein source (typically soybean meal) which are then supplemented with a small amount of fat and a premix containing, e.g., vitamins and minerals. The protease will mainly help digest the protein source and one way of measuring this utilization is determining the ileal nitrogen digestibility in an animal, such as broilers. The higher the ileal nitrogen digestibility, the better the protein has been degraded which would typically lead to improved body weight gain and FCR in the animal.

In order to determine whether the protease has actually improved the ileal nitrogen digestibility, it is desirable to run the in vivo trial with both a positive and negative control. The enzyme is added on top of the negative control whilst the positive control swaps out some of the soybean meal with a more digestible protein source, such as soy protein concentrate. The PC will normally show an improved ileal nitrogen digestibility compared to NC, although if the protein content in the NC is highly digestible then the difference may be quite small. However, proteases of interest, such as those of the present invention, will show an improved ileal nitrogen digestibility compared to NC and preferably also PC.

Thus in a first aspect, the invention relates to an animal feed additive comprising one or more polypeptides having protease activity, wherein the polypeptide is an S8 protease and has at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 1.

The animal feed additive preferably comprises or consists of SEQ ID NO: 1 or an allelic variant thereof; comprises SEQ ID NO: 1 and an N-terminal and/or C-terminal His-tag and/or HQ-tag; comprises SEQ ID NO: 1 and an N-terminal and/or C-terminal extension of between 1 and 10 amino acids; or is a fragment thereof having protease activity and having at least 90% such as at least 91%, at least 92%, at least 93%, at least 94%, at least 95%, at least 96%, at least 97%, at least 98% or at least 99% of the length of SEQ ID NO: 1. In another embodiment, the animal feed additive comprises or consists of amino acids 1 to 314 of SEQ ID NO: 1. In another embodiment, the animal feed additive comprises or consists of amino acids 2 to 314 of SEQ ID NO: 1. In another embodiment, the animal feed additive comprises or consists of amino acids 4 to 314 of SEQ ID NO: 1. In an embodiment, the polypeptide has been isolated.

In a continuation of the first aspect, the invention relates to an animal feed additive comprising one or more variants of SEQ ID NO: 1, wherein the variant is an S8 protease having protease activity and comprises one or more substitutions, and/or deletions, and/or insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising a substitution and/or deletion and/or insertion or any combination thereof in SEQ ID NO: 1 is between 1 and 50, such as 1-45, 1-40, 1-35, 1-30, 1-25, 1-20, 1-15, 1-10 or 1-5 positions. In an embodiment, the number of positions comprising a substitution and/or deletion and/or insertion or any combination thereof in SEQ ID NO: 1 is not more than 10, e.g., 1, 2, 3, 4, 5, 6, 7, 8, 9 or 10. In another embodiment, the number of substitutions and/or deletions and/or insertions in SEQ ID NO: 1 is not more than 10, e.g., 1, 2, 3, 4, 5, 6, 7, 8, 9 or 10. In a further embodiment, the number of substitutions, preferably conservative substitutions, in SEQ ID NO: 1 is not more than 10, e.g., 1, 2, 3, 4, 5, 6, 7, 8, 9 or 10.

As stated, an embodiment of the invention relates to an animal feed or animal feed additive comprising a variant of SEQ ID NO: 1, SEQ ID NO: 2, SEQ ID NO: 3; SEQ ID NO: 5, SEQ ID NO: 6, SEQ ID NO: 7, SEQ ID NO: 8, or SEQ ID NO: 9, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. A number of single mutation and multiple mutation variants of SEQ ID NO: 1, SEQ ID NO: 2, SEQ ID NO: 3; SEQ ID NO: 5, SEQ ID NO: 6, SEQ ID NO: 7, SEQ ID NO: 8, and SEQ ID NO: 9, have been prepared. Examples 12, 14 and 15 illustrate the gastric stability and for their in vivo performance of SEQ ID NO: 1. Single mutation (data not shown) and multiple mutation variants were tested and found to have better acid stability, gastric stability and residual activity compared to the parent polypeptide of SEQ ID NO: 1. Accordingly, an embodiment of the invention relates to an animal feed additive or animal feed composition comprising SEQ ID NO: 1, SEQ ID NO: 2, SEQ ID NO: 3; SEQ ID NO: 5, SEQ ID NO: 6, SEQ ID NO: 7, SEQ ID NO: 8, or SEQ ID NO: 9, or a variant thereof wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions, typically 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, more typically 1, 2, 3, 4, 5, 6, 7, 8, 9, 10, 11, 12, 13, 14, 15, 16, 17, 18, 19 or 20 positions, or 1, 2, 3, 4, 5, 6, 7, 8, 9, 10, 11, 12, 13, 14, or 15 positions, or 1, 2, 3, 4, 5, 6, 7, 8, 9, 10, 11 or 12 positions.

The variant with the combination of mutations S173P, S175P, T297P improved the acid stability compared to SEQ ID NO: 1 and was used as a starting point for further mutations. Accordingly, in one embodiment of the invention the polypeptide has at least 80%, such as at least 85% such as at least 90%, such as at least 95%, such as at least 96%, at least 97%, at least 98% or at least 99% sequence identity with any one of SEQ ID NO: 1, SEQ ID NO: 2, SEQ ID NO: 3; SEQ ID NO: 5, SEQ ID NO: 6, SEQ ID NO: 7, SEQ ID NO: 8, or SEQ ID NO: 9 comprising the S173P, S175P, T297P mutations. It is interesting to note that SEQ ID NO:3, which is a mutated form of SEQ ID NO:2 comprises the mutations S173P, S175P, T297P. As shown in the Examples, the animal feed additive suitably comprises an S8 protease having at least 90% identity to a polypeptide selected from the group consisting of SEQ ID NO:1, SEQ ID NO:2 SEQ ID NO:3, SEQ ID NO:5, SEQ ID NO:6, SEQ ID NO:7, SEQ ID NO:8 and SEQ ID NO:9, more typically consisting of SEQ ID NO:1, SEQ ID NO:5, SEQ ID NO:6, SEQ ID NO:7, SEQ ID NO:8 and SEQ ID NO:9, wherein the polypeptide comprises none, one or more of the mutations selected from the group consisting of S173P, S175P, T297P; L61P, V124A, R130D, S173P, S175P, T297P; H39D, L61P, S173P, S175P, T297P; L61P, H83T, S173P, S175P, T297P; L61P, E127N, S129M, S173P, S175P, T297P; H123W, V124A, R130D, S173P, S175P, T297P; N59D, H83T, S173P, S175P, T297P; N59D, E127N, S129M, S173P, S175P, T297P; L61Y, E127N, S129M, S173P, S175P, T297P; N59D, L61P, E127N, S129M, S173P, S175P, T297P; I43P, L61P, H123W, V124A, S173P, S175P, T297P; I43P, L61P, H83T, S173P, S175P, T297P; H39D, N59D, H83T, S173P, S175P, T297P; H39D, N59D, L61Y, S173P, S175P, T297P; H39D, H83T, H123W, V124A, S173P, S175P, T297P; H39D, L61Y, H123W, V124A, S173P, S175P, T297P; H39D, H83T, E127N, S129M, S173P, S175P, T297P; H39D, L61Y, H83T, S173P, S175P, T297P; L61Y, H83T, E127N, S129M, S173P, S175P, T297P; H39D, N59D, L61Y, H83T, S173P, S175P, T297P; I43P, L61P, S173P, S175P, T297P; H83T, V124A, R130D, S173P, S175P, T297P; L61Y, V124A, R130D, S173P, S175P, T297P; I43P, N59D, S173P, S175P, T297P; H83T, E127N, S129M, S173P, S175P, T297P; L61P, H123W, V124A, R130D, S173P, S175P, T297P; I43P, L61P, V124A, R130D, S173P, S175P, T297P; H39D, N59D, L61P, S173P, S175P, T297P; I43P, L61P, E127N, S129M, S173P, S175P, T297P; L61P, H83T, E127N, S129M, S173P, S175P, T297P; I43P, H83T, V124A, R130D, S173P, S175P, T297P; I43P, L61Y, V124A, R130D, S173P, S175P, T297P; I43P, N59D, H123W, V124A, S173P, S175P, T297P; N59D, H83T, H123W, V124A, S173P, S175P, T297P; N59D, L61Y, H123W, V124A, S173P, S175P, T297P; H39D, N59D, E127N, S129M, S173P, S175P, T297P; I43P, L61Y, H123W, V124A, S173P, S175P, T297P; H39D, N59D, L61P, H83T, S173P, S175P, T297P; I43P, N59D, L61P, H83T, S173P, S175P, T297P; H39D, I43P, N59D, L61Y, S173P, S175P, T297P and L61Y, H83T, S173P, S175P, T297P.

The animal feed additive, in an embodiment of the invention, typically comprises a polypeptide selected from the group consisting of SEQ ID NO: 1, SEQ ID NO: 2, SEQ ID NO: 3; SEQ ID NO: 5, SEQ ID NO: 6, SEQ ID NO: 7, SEQ ID NO: 8, or SEQ ID NO: 9, or a variant thereof wherein the variant has protease activity and comprises one or more substitutions, and/or one or more deletions, and/or one or more insertions or any combination thereof wherein one or more substitutions are multiple mutations comprising mutations selected from the group consisting of S173P, S175P, T297P; L61P, V124A, R130D, S173P, S175P, T297P; H39D, L61P, S173P, S175P, T297P; L61P, H83T, S173P, S175P, T297P; L61P, E127N, S129M, S173P, S175P, T297P; H123W, V124A, R130D, S173P, S175P, T297P; N59D, H83T, S173P, S175P, T297P; N59D, E127N, S129M, S173P, S175P, T297P; L61Y, E127N, S129M, S173P, S175P, T297P; N59D, L61P, E127N, S129M, S173P, S175P, T297P; I43P, L61P, H123W, V124A, S173P, S175P, T297P; I43P, L61P, H83T, S173P, S175P, T297P; H39D, N59D, H83T, S173P, S175P, T297P; H39D, N59D, L61Y, S173P, S175P, T297P; H39D, H83T, H123W, V124A, S173P, S175P, T297P; H39D, L61Y, H123W, V124A, S173P, S175P, T297P; H39D, H83T, E127N, S129M, S173P, S175P, T297P; H39D, L61Y, H83T, S173P, S175P, T297P; L61Y, H83T, E127N, S129M, S173P, S175P, T297P; H39D, N59D, L61Y, H83T, S173P, S175P, T297P; I43P, L61P, S173P, S175P, T297P; H83T, V124A, R130D, S173P, S175P, T297P; L61Y, V124A, R130D, S173P, S175P, T297P; I43P, N59D, S173P, S175P, T297P; H83T, E127N, S129M, S173P, S175P, T297P; L61P, H123W, V124A, R130D, S173P, S175P, T297P; I43P, L61P, V124A, R130D, S173P, S175P, T297P; H39D, N59D, L61P, S173P, S175P, T297P; I43P, L61P, E127N, S129M, S173P, S175P, T297P; L61P, H83T, E127N, S129M, S173P, S175P, T297P; I43P, H83T, V124A, R130D, S173P, S175P, T297P; I43P, L61Y, V124A, R130D, S173P, S175P, T297P; I43P, N59D, H123W, V124A, S173P, S175P, T297P; N59D, H83T, H123W, V124A, S173P, S175P, T297P; N59D, L61Y, H123W, V124A, S173P, S175P, T297P; H39D, N59D, E127N, S129M, S173P, S175P, T297P; I43P, L61Y, H123W, V124A, S173P, S175P, T297P; H39D, N59D, L61P, H83T, S173P, S175P, T297P; I43P, N59D, L61P, H83T, S173P, S175P, T297P; H39D, I43P, N59D, L61Y, S173P, S175P, T297P and L61Y, H83T, S173P, S175P, T297P.

Furthermore, a number of homologs were prepared. SEQ ID NO:1, SEQ ID NO:5 and SEQ ID NO:6, SEQ ID NO:7 SEQ ID NO:8 and SEQ ID NO:9 are homologs of each other.

| | |
|---|---|
| SEQ ID NO: 5 | S8, *Bacillus* sp-13380 (78% to SEQ ID NO: 1) |
| SEQ ID NO: 6 | S8, *Bacillus idriensis* (80% to SEQ ID NO: 1) |
| SEQ ID NO: 7 | S8, *Bacillus* sp-13380 (89% to SEQ ID NO: 1) |
| SEQ ID NO: 8 | S8, *Bacillus* sp-62451 (90% to SEQ ID NO: 1) |
| SEQ ID NO: 9 | S8, *Bacillus oceanisediminis* (87% SEQ ID NO: 1) |

An embodiment of the invention relates to the animal feed additive of the invention wherein the polypeptide is an S8 protease selected from the group consisting of an S8 protease from *Bacillus* sp-13380 having at least 75%, such as at least 76%, at least 77%, such as at least 78% sequence identity to SEQ ID NO: 1, an S8 protease from *Bacillus idriensis* having at 80% sequence identity to SEQ ID NO: 1, an S8 protease from *Bacillus* sp-62451 having at least 90% sequence identity to SEQ ID NO: 1, and an S8 protease from *Bacillus oceanisediminis* having at least 85%, such as at least 86%, such as at least 87% SEQ ID NO: 1. A further embodiment of the invention relates to a feed additive comprising an S8 protease having at least 90% identity to a polypeptide selected from the group consisting of SEQ ID NO:1, SEQ ID NO:5 and SEQ ID NO:6, SEQ ID NO:7, SEQ ID NO:8 and SEQ ID NO:9.

In an embodiment to any part of the first aspect, the polypeptide (or variant) comprises one or more motifs TGXK[V/T][I/V]X[N/S]MSLG (SEQ ID NO: 4). In an embodiment to any part of the first aspect, the polypeptide (or variant) is obtained or obtainable from the taxonomic order Bacillales, preferably the taxonomic family Bacillaceae, or more preferably the taxonomic genus *Bacillus*.

In an embodiment to any part of the first aspect, the polypeptide (or variant) has at least 70%, at least 75%, at least 80%, at least 85%, at least 90%, at least 95% or at least 100% of the protease activity of the polypeptide of SEQ ID NO: 1. In an embodiment to any part of the first aspect, the polypeptide (or variant) improves the ileal nitrogen digestibility by at least 1%, such as at least 1.5%, at least 2.0%, least 2.5%, at least 3.0%, least 3.5%, or at least 4.0% compared to negative control where no protease (variant) is added to the diet.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989*, Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996*, J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992*, Science* 255: 306-312; Smith et al., 1992*, J. Mol. Biol.* 224: 899-904; Wlodaver et al., 1992*, FEBS Lett.* 309: 59-64. The identity of essential amino acids can also be inferred from an alignment with a related polypeptide.

Peptidase family S8 contains serine endopeptidases and is the second largest family of serine peptidases, both in terms of number of sequences and characterized peptidases. In subfamily S8A, the active site residues frequently occur in the motifs Asp-Thr/Ser-Gly, His-Gly-Thr-His and Gly-Thr- Ser-Met-Ala-Xaa-Pro. From this the catalytic residues were identified as Asp-35, His-72 and Ser-251 and the fourth active site amino acid was identified as Asn-170 for SEQ ID NO: 1, 2 and 3. Mutation of any of the amino acids of the catalytic residues will result in a change or loss of enzyme activity.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

In a second aspect, the invention relates to an animal feed additive comprising one or more polypeptides having protease activity, wherein the polypeptide is an S8 protease and has at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 2.

The animal feed additive preferably comprises or consists of SEQ ID NO: 2 or an allelic variant thereof; comprises SEQ ID NO: 2 and an N-terminal and/or C-terminal His-tag and/or HQ-tag; comprises SEQ ID NO: 2 and an N-terminal and/or C-terminal extension of between 1 and 10 amino acids; or is a fragment thereof having protease activity and having at least 90% such as at least 91%, at least 92%, at least 93%, at least 94%, at least 95%, at least 96%, at least 97%, at least 98% or at least 99% of the length of SEQ ID NO: 2. In another embodiment, the animal feed additive comprises or consists of amino acids 1 to 311 of SEQ ID NO: 2. In an embodiment, the polypeptide has been isolated.

In a continuation of the second aspect, the invention relates to an animal feed additive comprising one or more variants of SEQ ID NO: 2, wherein the variant is an S8 protease having protease activity and comprises one or more substitutions, and/or deletions, and/or insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising a substitution and/or deletion and/or insertion or any combination thereof in SEQ ID NO: 2 is between 1 and 50, such as 1-45, 1-40, 1-35, 1-30, 1-25, 1-20, 1-15, 1-10 or 1-5 positions. In an embodiment, the number of positions comprising a substitution and/or deletion and/or insertion or any combination thereof in SEQ ID NO: 2 is not more than 10, e.g., 1, 2, 3, 4, 5, 6, 7, 8, 9 or 10. In another embodiment, the number of substitutions and/or deletions and/or insertions in SEQ ID NO: 2 is not more than 10, e.g., 1, 2, 3, 4, 5, 6, 7, 8, 9 or 10. In a further embodiment, the number of substitutions, preferably conservative substitutions, in SEQ ID NO: 2 is not more than 10, e.g., 1, 2, 3, 4, 5, 6, 7, 8, 9 or 10. Examples of amino acid changes, conservative substitutions and fusion peptides are described in the second aspect herein.

In an embodiment to any part of the second aspect, the polypeptide (or variant) comprises one or more motifs TGXK[V/T][I/V]X[N/S]MSLG (SEQ ID NO: 4). In an embodiment to any part of the second aspect, the polypeptide (or variant) is obtained or obtainable from the taxonomic order Bacillales, preferably the taxonomic family Bacillaceae, or more preferably the taxonomic genus *Bacillus*.

In an embodiment to any part of the second aspect, the polypeptide (or variant) has at least 40%, such as at least 50%, at least 60%, at least 70%, at least 75%, at least 80%, at least 85%, at least 90%, at least 95% or at least 100% of the protease activity of the polypeptide of SEQ ID NO: 1. In an embodiment to any part of the second aspect, the polypeptide (or variant) improves the ileal nitrogen digestibility by at least 1%, such as at least 1.5%, at least 2.0%, least 2.5%, at least 3.0%, least 3.5%, or at least 4.0% compared to negative control where no protease (variant) is added to the diet.

In a third aspect, the invention relates to an animal feed additive comprising one or more polypeptides having protease activity, wherein the polypeptide is an S8 protease and has at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3.

The animal feed additive preferably comprises or consists of SEQ ID NO: 3 or an allelic variant thereof; comprises SEQ ID NO: 3 and an N-terminal and/or C-terminal His-tag and/or HQ-tag; comprises SEQ ID NO: 3 and an N-terminal and/or C-terminal extension of between 1 and 10 amino acids; or is a fragment thereof having protease activity and having at least 90% such as at least 91%, at least 92%, at least 93%, at least 94%, at least 95%, at least 96%, at least 97%, at least 98% or at least 99% of the length of SEQ ID NO: 3. In another embodiment, the animal feed additive comprises or consists of amino acids 1 to 311 of SEQ ID NO: 3. In an embodiment, the polypeptide has been isolated.

In a continuation of the third aspect, the invention relates to an animal feed additive comprising one or more variants of SEQ ID NO: 3, wherein the variant is an S8 protease having protease activity and comprises one or more substitutions, and/or deletions, and/or insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising a substitution and/or deletion and/or insertion or any combination thereof in SEQ ID NO: 3 is between 1 and 50, such as 1-45, 1-40, 1-35, 1-30, 1-25, 1-20, 1-15, 1-10 or 1-5 positions. In an embodiment, the number of positions comprising a substitution and/or deletion and/or insertion or any combination thereof in SEQ ID NO: 3 is not more than 10, e.g., 1, 2, 3, 4, 5, 6, 7, 8, 9 or 10. In another embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 is not more than 10, e.g., 1, 2, 3, 4, 5, 6, 7, 8, 9 or 10. Examples of amino acid changes, conservative substitutions and fusion peptides are described in the second aspect herein.

A further interesting aspect of the invention is directed to a feed additive comprising an S8 protease having at least 90% identity such as at least 95%, such as at least 96%, at least 97%, at least 98% or at least 99% sequence identity to a polypeptide selected from the group consisting of SEQ ID NO:2 and SEQ ID NO:3. The amino acid sequences of SEQ ID NO:2 and SEQ ID NO:3 differ at 13 positions. Accordingly, an embodiment of the invention relates to a feed additive comprising an S8 protease having at least 90% identity such as at least 95%, such as at least 96%, at least 97%, at least 98% or at least 99% sequence identity with a polypeptide selected from the group consisting of SEQ ID NO:1, SEQ ID NO:2 and SEQ ID NO:3, particularly SEQ ID NO:2 and SEQ ID NO:3 wherein the polypeptide comprises a mutation at none, one or more of positions 27, 109, 111, 171, 173, 174, 175, 180, 182, 184, 198, 199 and 297. The animal feed additive of the invention preferably comprises an S8 protease having at least 90% identity to a polypeptide selected from the group consisting of SEQ ID NO:2 and SEQ ID NO:3, or wherein the S8 protease is a polypeptide comprises a mutation at none, one or more of positions 27, 109, 111, 171, 173, 174, 175, 180, 182, 184, 198, 199 and 297 of SEQ ID NO:2 or SEQ ID NO:3. An embodiment of the invention relates to a feed additive comprising an S8 protease having at least 90% identity such as at least 95%, such as at least 96%, at least 97%, at least 98% or at least 99% sequence identity with a polypeptide selected from the group consisting of SEQ ID NO:1, SEQ ID NO:2 and SEQ ID NO:3, typically SEQ ID NO:2 and SEQ ID NO:3, wherein the polypeptide comprises none, one or more of the mutations selected from the group consisting of S27K, N109K, S111E, S171E, S173P, G174K, S175P, F180Y, G182A, L184F, Q198E, N199K and T297P.

An embodiment of the invention relates to a feed additive comprising an S8 protease having at least 90% identity such as at least 95%, such as at least 96%, at least 97%, at least 98% or at least 99% sequence identity with a polypeptide selected from the group consisting of SEQ ID NO:1, SEQ ID NO:2 and SEQ ID NO:3, typically SEQ ID NO:2 and SEQ ID NO:3, wherein the polypeptide comprises none, one or more of the mutations selected from the group consisting of S27K+N109K, S27K+S111E, S27K+S171E, S27K+S173P, S27K+G174K, S27K+S175P, S27K+F180Y, S27K+G182A, S27K+L184F, S27K+Q198E, S27K+N199K, N109K+S111E, N109K+S171E, N109K+S173P, N109K+G174K, N109K+S175P, N109K+F180Y, N109K+G182A, N109K+L184F, N109K+Q198E, N109K+N199K, S111E+S171E, S111E+S173P, S111E+G174K, S111E+S175P, S111E+F180Y, S111E+G182A, S111E+L184F, S111E+Q198E, S111E+N199K, S171E+S173P, S171E+G174K, S171E+S175P, S171E+F180Y, S171E+G182A, S171E+L184F, S171E+Q198E, S171E+N199K, S173P+G174K, S173P+S175P, S173P+F180Y, S173P+G182A, S173P+L184F, S173P+Q198E, S173P+N199K, G174K+S175P, G174K+F180Y, G174K+G182A, G174K+L184F, G174K+Q198E, G174K+N199K, S175P+F180Y, S175P+G182A, S175P+L184F, S175P+Q198E, S175P+N199K, F180Y+G182A, F180Y+L184F, F180Y+Q198E, F180Y+N199K, G182A+L184F, G182A+Q198E, G182A+N199K, L184F+Q198E, L184F+N199K, and Q198E+N199K.

An embodiment of the invention relates to a feed additive comprising an S8 protease having at least 90% identity to a polypeptide selected from the group consisting of SEQ ID NO:1, SEQ ID NO:2 and SEQ ID NO:3, typically SEQ ID NO:2 and SEQ ID NO:3, wherein the polypeptide comprises none, one or more of the mutations selected from the group consisting of S27K+N109K+S111E, S27K+N109K+S171E, S27K+N109K+S173P, S27K+N109K+G174K, S27K+N109K+S175P, S27K+N109K+F180Y, S27K+N109K+G182A, S27K+N109K+L184F, S27K+N109K+Q198E, S27K+N109K+N199K, S27K+S111E+S171E, S27K+S111E+S173P, S27K+S111E+G174K, S27K+S111E+S175P, S27K+S111E+F180Y, S27K+S111E+G182A, S27K+S111E+L184F, S27K+S111E+Q198E, S27K+S111E+N199K, S27K+S171E+S173P, S27K+S171E+G174K, S27K+S171E+S175P, S27K+S171E+F180Y, S27K+S171E+G182A, S27K+S171E+L184F, S27K+S171E+Q198E, S27K+S171E+N199K, S27K+S173P+G174K, S27K+S173P+S175P, S27K+S173P+F180Y, S27K+S173P+G182A, S27K+S173P+L184F, S27K+S173P+Q198E, S27K+S173P+N199K, S27K+G174K+S175P, S27K+G174K+F180Y, S27K+G174K+G182A, S27K+G174K+L184F, S27K+G174K+Q198E, S27K+G174K+N199K, S27K+S175P+F180Y, S27K+S175P+G182A, S27K+S175P+L184F, S27K+S175P+Q198E, S27K+S175P+N199K, S27K+F180Y+G182A, S27K+F180Y+Q198E, S27K+F180Y+N199K, S27K+G182A+L184F, S27K+G182A+Q198E, S27K+G182A+N199K, S27K+L184F+Q198E, S27K+L184F+N199K, S27K+

Q198E+N199K, N109K+S111E+S171E N109K+S111E+ S173P, N109K+S111E+G174K, N109K+S111E+S175P, N109K+S111E+F180Y, N109K+S111E+G182A, N109K+ S111E+L184F, N109K+S111E+Q198E, N109K+S111E+ N199K, N109K+S171E+S173P, N109K+S171E+G174K, N109K+S171E+S175P, N109K+S171E+F180Y, N109K+ S171E+G182A, N109K+S171E+L184F, N109K+S171E+ Q198E, N109K+S171E+N199K, N109K+S173P+G174K, N109K+S173P+S175P, N109K+S173P+F180Y, N109K+ S173P+G182A, N109K+S173P+L184F, N109K+S173P+ Q198E, N109K+S173P+N199K, N109K+G174K+S175P, N109K+G174K+F180Y, N109K+G174K+G182A, N109K+ G174K+L184F, N109K+G174K+Q198E, N109K+G174K+ N199K, N109K+S175P+F180Y, N109K+S175P+G182A, N109K+S175P+L184F, N109K+S175P+Q198E, N109K+ S175P+N199K, N109K+F180Y+G182A, N109K+F180Y+ L184F, N109K+F180Y+Q198E, N109K+F180Y+N199K, N109K+G182A+L184F, N109K+G182A+Q198E, N109K+ G182A+N199K, N109K+L184F+Q198E, N109K+L184F+ N199K, N109K+Q198E+N199K, S111E+S171E+S173P, S111E+S171E+G174K, S111E+S171E+S175P, S111E+ S171E+F180Y, S111E+S171E+G182A, S111E+S171E+ L184F, S111E+S171E+Q198E, S111E+S171E+N199K, S111E+S173P+G174K, S111E+S173P+S175P, S111E+ S173P+F180Y, S111E+S173P+G182A, S111E+S173P+ L184F, S111E+S173P+Q198E, S111E+S173P+N199K, S111E+G174K+S175P, S111E+G174K+F180Y, S111E+ G174K+G182A, S111E+G174K+L184F, S111E+G174K+ Q198E, S111E+G174K+N199K, S111E+S175P+F180Y, S111E+S175P+G182A, S111E+S175P+L184F, S111E+ S175P+Q198E, S111E+S175P+N199K, S111E+F180Y+ G182A, S111E+F180Y+L184F, S111E+F180Y+Q198E, S111E+F180Y+N199K, S111E+G182A+L184F, S111E+ G182A+Q198E, S111E+G182A+N199K, S111E+L184F+ Q198E, S111E+L184F+N199K, S111E+Q198E+N199K, S171E+S173P+G174K, S171E+S173P+S175P, S171E+ S173P+F180Y, S171E+S173P+G182A, S171E+S173P+ L184F, S171E+S173P+Q198E, S171E+S173P+N199K, S171E+G174K+S175P, S171E+G174K+F180Y, S171E+ G174K+G182A, S171E+G174K+L184F, S171E+G174K+ Q198E, S171E+G174K+N199K, S171E+S175P+F180Y, S171E+S175P+G182A, S171E+S175P+L184F, S171E+ S175P+Q198E, S171E+S175P+N199K, S171E+F180Y+ G182A, S171E+F180Y+L184F, S171E+F180Y+Q198E, S171E+F180Y+N199K, S171E+G182A+L184F, S171E+ G182A+Q198E, S171E+G182A+N199K, S171E+L184F+ Q198E, S171E+L184F+N199K, S171E+Q198E+N199K, S173P+G174K+S175P, S173P+G174K+F180Y, S173P+ G174K+G182A, S173P+G174K+L184F, S173P+G174K+ Q198E, S173P+G174K+N199K, S173P+S175P+F180Y, S173P+S175P+G182A, S173P+S175P+L184F, S173P+ S175P+Q198E, S173P+S175P+N199K, S173P+F180Y+ G182A, S173P+F180Y+L184F, S173P+F180Y+Q198E, S173P+F180Y+N199K, S173P+G182A+L184F, S173P+ G182A+Q198E, S173P+G182A+N199K, S173P+L184F+ Q198E, S173P+L184F+N199K, S173P+Q198E+N199K, G174K+S175P+F180Y, G174K+S175P+G182A, G174K+ S175P+L184F, G174K+S175P+Q198E, G174K+S175P+ N199K, G174K+F180Y+G182A, G174K+F180Y+L184F, G174K+F180Y+Q198E, G174K+F180Y+N199K, G174K+ G182A+L184F, G174K+G182A+Q198E, G174K+G182A+ N199K, G174K+L184F+Q198E, G174K+L184F+N199K, G174K+Q198E+N199K, S175P+F180Y+G182A, S175P+ F180Y+L184F, S175P+F180Y+Q198E, S175P+F180Y+ N199K, S175P+G182A+L184F, S175P+G182A+Q198E, S175P+G182A+N199K, S175P+L184F+Q198E, S175P+ L184F+N199K, S175P+Q198E+N199K, F180Y+G182A+ L184F, F180Y+G182A+Q198E, F180Y+G182A+N199K, F180Y+L184F+Q198E, F180Y+L184F+N199K, F180Y+ Q198E+N199K, G182A+L184F+Q198E, G182A+L184F+ N199K, G182A+Q198E+N199K and L184F+Q198E+ N199K.

An embodiment of the invention relates to a feed additive comprising an S8 protease having at least 90% identity to a polypeptide selected from the group consisting of SEQ ID NO:1, SEQ ID NO:2 and SEQ ID NO:3, typically SEQ ID NO:2 and SEQ ID NO:3, wherein the polypeptide comprises none, one or more of the mutations selected from the group consisting of S27K+N109K+S111E+S171E+S173P+ G174K+175P+F180Y+G182A, S27K+N109K+S111E+ S171E+S5173P+G174K+S175P+F180Y+L184F, S27K+ N109K+S111E+S171E+S173P+G174K+S175P+F180Y+ Q198E, S27K+N109K+S111E+S171E+S173P+G174K+ S175P+F180Y+N199K, S27K+N109K+S111E+S171E+ S173P+G174K+S175P+G182A+L184F, S27K+N109K+ S111E+S171E+S173P+G174K+S175P+G182A+Q198E, S27K+N109K+S111E+S171E+S173P+G174K+S175P+ G182A+N199K, S27K+N109K+S111E+S171E+S173P+ G174K+S175P+L184F+Q198E, S27K+N109K+S111E+ S171E+S173P+G174K+175P+L184F+N199K, S27K+ N109K+S111E+S171E+S173P+G174K+S175P+Q198E+ N199K, S27K+N109K+S111E+S171E+S173P+G174K+ F180Y+G182A+L184F, S27K+N109K+S111E+S171E+ S173P+G174K+F180Y+G182A+Q198E, S27K+N109K+ S111E+S171E+S173P+G174K+F180Y+G182A+N199K, S27K+N109K+S111E+S171E+S173P+G174K+F180Y+ L184F+Q198E, S27K+N109K+S111E+S171E+S173P+ G174K+F180Y+L184F+N199K, S27K+N109K+S111E+ S171E+S173P+G174K+F180Y+Q198E+N199K, S27K+ N109K+S111E+S171E+173P+G174K+G182A+L184F+ Q198E, S27K+N109K+S111E+S171E+173P+G174K+ G182A+L184F+N199K, S27K+N109K+S111E+S171E+ S173P+G174K+G182A+Q198E+N199K, S27K+N109K+ S111E+S171E+S173P+G174K+L184F+Q198E+N199K, S27K+N109K+S111E+S171E+S173P+S175P+F18Y+ G182A+L184F, S27K+N109K+S111E+S171E+S173P+ S175P+F18Y+G182A+Q198E, S27K+N109K+S111E+ S171E+S173P+S175P+F18Y+G182A+N199K, S27K+ N109K+S111E+S171E+S173P+S175P+F180Y+L184F+ Q198E, S27K+N109K+S111E+S171E+S173P+S175P+ F180Y+L184F+N199K, S27K+N109K+S111E+S171E+ S173P+S175P+F180Y+Q198E+N199K, S27K+N109K+ S111E+S171E+S173P+S175P+G182A+L184F+Q198E, S27K+N109K+S111E+S171E+S173P+S175P+G182A+ L184F+N199K, S27K+N109K+S111E+S171E+S173P+ S175P+G182A+Q198E+N199K, S27K+N109K+S111E+ S171E+S173P+S175P+L184F+Q198E+N199K, S27K+ N109K+S111E+S171E+S173P+F180Y+G182A+L184F+ Q198E, S27K+N109K+S111E+S171E+S173P+F180Y+ G182A+L184F+N199K, S27K+N109K+S111E+S171E+ S173P+F180Y+G182A+Q198E+N199K, S27K+N109K+ S111E+S171E+S173P+F18Y+L184F+Q198E+N199K, S27K+N109K+S111E+S171E+S173P+G182A+L184F+ Q198E+N199K, S27K+N109K+S111E+S171E+G174K+ S175P+F180Y+G182A+L184F, S27K+N109K+S111E+ S171E+G174K+S175P+F180Y+G182A+Q198E, S27K+ N109K+S111E+S171E+G174K+S175P+F180Y+G182A+ N199K, S27K+N109K+S111E+S171E+G174K+S175P+ F180Y+L184F+Q198E, S27K+N109K+S111E+S171E+ G174K+S175P+F180Y+L184F+N199K, S27K+N109K+ S111E+S171E+G174K+S175P+F180Y+Q198E+N199K, S27K+N109K+S111E+S171E+G174K+S175P+G182A+ L184F+Q198E, S27K+N109K+S111E+S171E+G174K+ S175P+G182A+L184F+N199K, S27K+N109K+S111E+

S171E+G174K+S175P+G182A+Q198E+N199K, S27K+ N109K+S111E+S171E+G174K+S175P+L184F+Q198E+ N199K, S27K+N109K+S111E+S171E+G174K+F18Y+ G182A+L184F+Q198E, S27K+N109K+S111E+S171E+ G174K+F18Y+G182A+L184F+N199K, S27K+N109K+ S111E+S171E+G174K+F18Y+G182A+Q198E+N199K, S27K+N109K+S111E+S171E+G174K+F18Y+L184F+ Q198E+N199K, S27K+N109K+S111E+S171E+G174K+ G182A+L184F+Q198E+N199K, S27K+N109K+S111E+ S171E+S175P+F180Y+G182A+L184F+Q198E, S27K+ N109K+S111E+S171E+S175P+F180Y+G182A+L184F+ N199K, S27K+N109K+S111E+S171E+S175P+F180Y+ G182A+Q198E+N199K, S27K+N109K+S111E+S171E+ S175P+F180Y+L184F+Q198E+N199K, S27K+N109K+ S111E+S171E+S175P+G182A+L184F+Q198E+N199K, S27K+N109K+S111E+S171E+F180Y+G182A+L184F+ Q198E+N199K, S27K+N109K+S111E+S173P+G174K+ S175P+F180Y+G182A+L184F, S27K+N109K+S111E+ S173P+G174K+S175P+F180Y+G182A+Q198E, S27K+ N109K+S111E+S173P+G174K+S175P+F18Y+G182A+ N199K, S27K+N109K+S111E+S173P+G174K+S175P+ F180Y+L184F+Q198E, S27K+N109K+S111E+S173P+ G174K+S175P+F180Y+L184F+N199K, S27K+N109K+ S111E+S173P+G174K+S175P+F180Y+Q198E+N199K, S27K+N109K+S111E+S173P+G174K+S175P+G182A+ L184F+Q198E, S27K+N109K+S111E+S173P+G174K+ S175P+G182A+L184F+N199K, S27K+N109K+S111E+ S173P+G174K+S175P+G182A+Q198E+N199K, S27K+ N109K+S111E+S173P+G174K+S175P+L184F+Q198E+ N199K, S27K+N109K+S111E+S173P+G174K+F180Y+ G182A+L184F+Q198E, S27K+N109K+S111E+S173P+ G174K+F180Y+G182A+L184F+N199K, S27K+N109K+ S111E+S173P+G174K+F180Y+G182A+Q198E+N199K, S27K+N109K+S111E+S173P+G174K+F180Y+L184F+ Q198E+N199K, S27K+N109K+S111E+S173P+G174K+ G182A+L184F+Q198E+N199K, S27K+N109K+S111E+ S173P+S175P+F180Y+G182A+L184F+Q198E, S27K+ N109K+S111E+S173P+S175P+F180Y+G182A+L184F+ N199K, S27K+N109K+S111E+S173P+S175P+F180Y+ G182A+Q198E+N199K, S27K+N109K+S111E+S173P+ S175P+F180Y+L184F+Q198E+N199K, S27K+N109K+ S111E+S173P+S175P+G182A+L184F+Q198E+N199K, S27K+N109K+S111E+S173P+F180Y+G182A+L184F+ Q198E+N199K, S27K+N109K+S111E+G174K+S175P+ F180Y+G182A+L184F+Q198E, S27K+N109K+S111E+ G174K+S175P+F18Y+G182A+L184F+N199K, S27K+ N109K+S111E+G174K+S175P+F18Y+G182A+Q198E+ N199K, S27K+N109K+S111E+G174K+S175P+F180Y+ L184F+Q198E+N199K, S27K+N109K+S111E+G174K+ S175P+G182A+L184F+Q198E+N199K, S27K+N109K+S111E+G174K+F180Y+G182A+L184F+Q198E+N199K, S27K+N109K+S111E+S175P+F180Y+G182A+L184F+Q198E+N199K, S27K+N109K+S171E+S173P+G174K+S175P+F180Y+G182A+L184F, S27K+N109K+S171E+S173P+G174K+S175P+F180Y+G182A+Q198E, S27K+N109K+S171E+S173P+G174K+S175P+F180Y+G182A+N199K, S27K+N109K+S171E+S173P+G174K+S175P+F180Y+L184F+Q198E, S27K+N109K+S171E+S173P+G174K+S175P+F180Y+L184F+N199K, S27K+N109K+S171E+S173P+G174K+S175P+F180Y+Q198E+N199K, S27K+N109K+S171E+S173P+G174K+S175P+G182A+L184F+Q198E, S27K+N109K+S171E+S173P+G174K+S175P+G182A+L184F+N199K, S27K+N109K+S171E+S173P+G174K+S175P+G182A+Q198E+N199K, S27K+N109K+S171E+S173P+G174K+S175P+L184F+Q198E+N199K, S27K+N109K+S171E+S173P+G174K+F18Y+G182A+L184F+Q198E, S27K+N109K+S171E+S173P+G174K+F180Y+G182A+L184F+N199K, S27K+N109K+S171E+S173P+G174K+F180Y+G182A+Q198E+N199K, S27K+N109K+S171E+S173P+G174K+F180Y+L184F+Q198E+N199K, S27K+N109K+S171E+S173P+G174K+G182A+L184F+Q198E+N199K, S27K+N109K+S171E+S173P+S175P+F180Y+G182A+L184F+Q198E, S27K+N109K+S171E+S173P+S175P+F180Y+G182A+L184F+N199K, S27K+N109K+S171E+S173P+S175P+F180Y+G182A+Q198E+N199K, S27K+N109K+S171E+S173P+S175P+F180Y+L184F+Q198E+N199K, S27K+N109K+S171E+S173P+S175P+G182A+L184F+Q198E+N199K, S27K+N109K+S171E+S173P+F180Y+G182A+L184F+Q198E+N199K, S27K+N109K+S171E+G174K+S175P+F180Y+G182A+L184F+Q198E, S27K+N109K+S171E+G174K+S175P+F18Y+G182A+L184F+N199K, S27K+N109K+S171E+G174K+S175P+F180Y+G182A+Q198E+N199K, S27K+N109K+S171E+G174K+S175P+F180Y+L184F+Q198E+N199K, S27K+N109K+S171E+G174K+S175P+G182A+L184F+Q198E+N199K, S27K+N109K+S171E+G174K+F180Y+G182A+L184F+Q198E+N199K, S27K+N109K+S171E+S175P+F180Y+G182A+L184F+Q198E+N199K, S27K+N109K+S173P+G174K+S175P+F180Y+G182A+L184F+Q198E, S27K+N109K+S173P+G174K+S175P+F180Y+G182A+L184F+N199K, S27K+N109K+S173P+G174K+S175P+F18Y+G182A+Q198E+N199K, S27K+N109K+S173P+G174K+S175P+F180Y+L184F+Q198E+N199K, S27K+N109K+S173P+G174K+S175P+G182A+L184F+Q198E+N199K, S27K+N109K+S173P+G174K+F180Y+G182A+L184F+Q198E+N199K, S27K+N109K+S173P+S175P+F180Y+G182A+L184F+Q198E+N199K, S27K+N109K+G174K+S175P+F180Y+G182A+L184F+Q198E+N199K, S27K+S111E+S171E+S173P+G174K+S175P+F180Y+G182A+L184F, S27K+S111E+S171E+S173P+G174K+S175P+F180Y+G182A+Q198E, S27K+S111E+S171E+S173P+G174K+S175P+F180Y+G182A+N199K, S27K+S111E+S171E+S173P+G174K+S175P+F180Y+L184F+Q198E, S27K+S111E+S171E+S173P+G174K+S175P+F180Y+L184F+N199K, S27K+S111E+S171E+S173P+G174K+S175P+F180Y+Q198E+N199K, S27K+S111E+S171E+S173P+G174K+S175P+G182A+L184F+Q198E, S27K+S111E+S171E+S173P+G174K+S175P+G182A+L184F+N199K, S27K+S111E+S171E+S173P+G174K+S175P+G182A+Q198E+N199K, S27K+S111E+S171E+S173P+G174K+S175P+L184F+Q198E+N199K, S27K+S111E+S171E+S173P+G174K+F180Y+G182A+L184F+Q198E, S27K+S111E+S171E+S173P+G174K+F180Y+G182A+L184F+N199K, S27K+S111E+S171E+S173P+G174K+F180Y+G182A+Q198E+N199K, S27K+S111E+S171E+S173P+G174K+F180Y+L184F+Q198E+N199K, S27K+S111E+S171E+S173P+G174K+G182A+L184F+Q198E+N199K, S27K+S111E+S171E+S173P+S175P+F180Y+G182A+L184F+Q198E, S27K+S111E+S171E+S173P+S175P+F180Y+G182A+L184F+N199K, S27K+S111E+S171E+S173P+S175P+F18Y+G182A+Q198E+N199K, S27K+S111E+S171E+S173P+S175P+F180Y+L184F+Q198E+N199K, S27K+S111E+S171E+S173P+S175P+G182A+L184F+Q198E+N199K, S27K+S111E+S171E+S173P+F180Y+G182A+L184F+Q198E+N199K, S27K+S111E+S171E+G174K+S175P+F180Y+G182A+L184F+Q198E, S27K+S111E+S171E+G174K+S175P+F180Y+G182A+L184F+N199K, S27K+S111E+S171E+G174K+S175P+F180Y+G182A+Q198E+N199K, S27K+S111E+S171E+G74K+S175P+F180Y+L184F+Q198E+N199K, S27K+S111E+S171E+G174K+S175P+G182A+L184F+Q198E+N199K, S27K+S111E+S171E+G174K+F180Y+G182A+L184F+Q198E+N199K, S27K+S111E+S171E+S175P+F180Y+

G182A+L184F+Q198E+N199K, S27K+S111E+S173P+ G174K+S175P+F180Y+G182A+L184F+Q198E, S27K+ S111E+S173P+G174K+S175P+F180Y+G182A+L184F+ N199K, S27K+S111E+S173P+G174K+S175P+F180Y+ G182A+Q198E+N199K, S27K+S111E+S173P+G174K+ S175P+F180Y+L184F+Q198E+N199K, S27K+S111E+ S173P+G174K+S175P+G182A+L184F+Q198E+N199K, S27K+S111E+S173P+G174K+F180Y+G182A+L184F+ Q198E+N199K, S27K+S111E+S173P+S175P+F180Y+ G182A+L184F+Q198E+N199K, S27K+S111E+G174K+ S175P+F180Y+G182A+L184F+Q198E+N199K, S27K+ S171E+S173P+G174K+S175P+F18Y+G182A+L184F+ Q198E, S27K+S171E+S173P+G174K+S175P+F180Y+ G182A+L184F+N199K, S27K+S171E+S173P+G174K+ S175P+F180Y+G182A+Q198E+N199K, S27K+S171E+ S173P+G174K+S175P+F180Y+L184F+Q198E+N199K, S27K+S171E+S173P+G174K+S175P+G182A+L184F+ Q198E+N199K, S27K+S171E+S173P+G174K+F180Y+ G182A+L184F+Q198E+N199K, S27K+S171E+S173P+ S175P+F180Y+G182A+L184F+Q198E+N199K, S27K+ S171E+G174K+S175P+F180Y+G182A+L184F+Q198E+ N199K, S27K+S173P+G174K+S175P+F180Y+G182A+ L184F+Q198E+N199K, N109K+S111E+S171E+S173P+ G174K+S175P+F18Y+G182A+L184F, N109K+S111E+ S171E+S173P+G174K+S175P+F180Y+G182A+Q198E, N109K+S111E+S171E+S173P+G174K+S175P+F18Y+ G182A+N199K, N109K+S111E+S171E+S173P+G174K+ S175P+F18Y+L184F+Q198E, N109K+S111E+S171E+ S173P+G174K+S175P+F180Y+L184F+N199K, N109K+ S111E+S171E+S173P+G174K+S175P+F180Y+Q198E+ N199K, N109K+S111E+S171E+S173P+G174K+S175P+ G182A+L184F+Q198E, N109K+S111E+S171E+S173P+ G174K+S175P+G182A+L184F+N199K, N109K+S111E+ S171E+S173P+G174K+S175P+G182A+Q198E+N199K, N109K+S111E+S171E+S173P+G174K+S175P+L184F+ Q198E+N199K, N109K+S111E+S171E+S173P+G174K+ F18Y+G182A+L184F+Q198E, N109K+S111E+S171E+ S173P+G174K+F180Y+G182A+L184F+N199K, N109K+ S111E+S171E+S173P+G174K+F180Y+G182A+Q198E+ N199K, N109K+S111E+S171E+S173P+G174K+F180Y+ L184F+Q198E+N199K, N109K+S111E+S171E+S173P+ G174K+G182A+L184F+Q198E+N199K, N109K+S111E+ S171E+S173P+S175P+F180Y+G182A+L184F+Q198E, N109K+S111E+S171E+S173P+S175P+F180Y+G182A+ L184F+N199K, N109K+S111E+S171E+S173P+S175P+ F180Y+G182A+Q198E+N199K, N109K+S111E+S171E+ S173P+S175P+F180Y+L184F+Q198E+N199K, N109K+ S111E+S171E+S173P+S175P+G182A+L184F+Q198E+ N199K, N109K+S111E+S171E+S173P+F180Y+G182A+ L184F+Q198E+N199K, N109K+S111E+S171E+G174K+ S175P+F180Y+G182A+L184F+Q198E, N109K+S111E+ S171E+G174K+S175P+F180Y+G182A+L184F+N199K, N109K+S111E+S171E+G174K+S175P+F180Y+G182A+ Q198E+N199K, N109K+S111E+S171E+G174K+S175P+ F18Y+L184F+Q198E+N199K, N109K+S111E+S171E+ G174K+S175P+G182A+L184F+Q198E+N199K, N109K+ S111E+S171E+G174K+F180Y+G182A+L184F+Q198E+ N199K, N109K+S111E+S171E+S175P+F180Y+G182A+ L184F+Q198E+N199K, N109K+S111E+S173P+G174K+ S175P+F180Y+G182A+L184F+Q198E, N109K+S111E+ S173P+G174K+S175P+F180Y+G182A+L184F+N199K, N109K+S111E+S173P+G174K+S175P+F18Y+G182A+ Q198E+N199K, N109K+S111E+S173P+G174K+S175P+ F180Y+L184F+Q198E+N199K, Ni 09K+S111E+S173P+ G174K+S175P+G182A+L184F+Q198E+N199K, N109K+ S111E+S173P+G174K+F180Y+G182A+L184F+Q198E+ N199K, N109K+S111E+S173P+S175P+F180Y+G182A+ L184F+Q198E+N199K, N109K+S111E+G174K+S175P+ F180Y+G182A+L184F+Q198E+N199K, N109K+S171E+ S173P+G174K+S175P+F18Y+G182A+L184F+Q198E, N109K+S171E+S173P+G174K+S175P+F180Y+G182A+ L184F+N199K, N109K+S171E+S173P+G174K+S175P+ F180Y+G182A+Q198E+N199K, N109K+S171E+S173P+ G174K+S175P+F180Y+L184F+Q198E+N199K, N109K+ S171E+173P+G174K+175P+G182A+L184F+Q198E+ N199K, N109K+S171E+S173P+G174K+F180Y+G182A+ L184F+Q198E+N199K, N109K+S171E+S173P+S175P+ F180Y+G182A+L184F+Q198E+N199K, N109K+S171E+ G174K+S175P+F180Y+G182A+L184F+Q198E+N199K, N109K+S173P+G174K+S175P+F180Y+G182A+L184F+ Q198E+N199K, S111E+S171E+S173P+G174K+S175P+ F180Y+G182A+L184F+Q198E, S111E+S171E+S173P+ G174K+S175P+F180Y+G182A+L184F+N199K, S111E+ S171E+S173P+G174K+S175P+F180Y+G182A+Q198E+ N199K, S111E+S171E+S173P+G174K+S175P+F180Y+ L184F+Q198E+N199K, S111E+S171E+S173P+G174K+ S175P+G182A+L184F+Q198E+N199K, S111E+S171E+ S173P+G174K+F180Y+G182A+L184F+Q198E+N199K, S111E+S171E+S173P+S175P+F180Y+G182A+L184F+ Q198E+N199K, S111E+S171E+G174K+S175P+F180Y+ G182A+L184F+Q198E+N199K, S111E+S173P+G174K+ S175P+F180Y+G182A+L184F+Q198E+N199K and S171E+S173P+G174K+S175P+F180Y+G182A+L184F+ Q198E+N199K An embodiment of the invention relates to a feed additive comprising an S8 protease having at least 90% identity to a polypeptide selected from the group consisting of SEQ ID NO:1, SEQ ID NO:2 and SEQ ID NO:3, typically SEQ ID NO:2 and SEQ ID NO:3, wherein the polypeptide comprises none, one or more of the mutations selected from the group consisting of S27K+N109K+S111E+S171E+S173P+ G174K+S175P+F180Y+G182A+L184F, S27K+N109K+ S111E+S171E+S173P+G174K+S175P+F180Y+G182A+ Q198E, S27K+N109K+S111E+S171E+S173P+G174K+ S175P+F180Y+G182A+N199K, S27K+N109K+S111E+ S171E+S173P+G174K+S175P+F180Y+L184F+Q198E, S27K+N109K+S111E+S171E+S173P+G174K+S175P+ F180Y+L184F+N199K, S27K+N109K+S111E+S171E+ S173P+G174K+S175P+F180Y+Q198E+N199K, S27K+ N109K+S111E+S171E+S173P+G174K+S175P+G182A+ L184F+Q198E, S27K+N109K+S111E+S171E+S173P+ G174K+S175P+G182A+L184F+N199K, S27K+N109K+ 111E+S171E+173P+G174K+175P+G182A+Q198E+ N199K, S27K+N109K+S111E+S171E+S173P+G174K+ S175P+L184F+Q198E+N199K, S27K+N109K+S111E+ S171E+S173P+G174K+F180Y+G182A+L184F+Q198E, S27K+N109K+S111E+S171E+S173P+G174K+F180Y+ G182A+L184F+N199K, S27K+N109K+S111E+S171E+ S173P+G174K+F180Y+G182A+Q198E+N199K, S27K+ N109K+S111E+S171E+S173P+G174K+F180Y+L184F+ Q198E+N199K, S27K+N109K+S111E+S171E+S173P+ G174K+G182A+L184F+Q198E+N199K, S27K+N109K+ S111E+S171E+S173P+S175P+F180Y+G182A+L184F+ Q198E, S27K+N109K+S111E+S171E+S173P+S175P+ F180Y+G182A+L184F+N199K, S27K+N109K+S111E+ S171E+S173P+S175P+F180Y+G182A+Q198E+N199K, S27K+N109K+S111E+S171E+S173P+S175P+F180Y+ L184F+Q198E+N199K, S27K+N109K+S111E+S171E+ S173P+S175P+G182A+L184F+Q198E+N199K, S27K+ N109K+S111E+S171E+S173P+F180Y+G182A+L184F+ Q198E+N199K, S27K+N109K+S111E+S171E+G174K+ S175P+F180Y+G182A+L184F+Q198E, S27K+N109K+ S111E+S171E+G174K+S175P+F18Y+G182A+L184F+ N199K, S27K+N109K+S111E+S171E+G174K+S175P+

F180Y+G182A+Q198E+N199K, S27K+N109K+S111E+S171E+G174K+S175P+F18Y+L184F+Q198E+N199K, S27K+N109K+S111E+S171E+G174K+S175P+G182A+L184F+Q198E+N199K, S27K+N109K+S111E+S171E+G174K+F180Y+G182A+L184F+Q198E+N199K, S27K+N109K+S111E+S171E+S175P+F180Y+G182A+L184F+Q198E+N199K, S27K+N109K+S111E+S173P+G174K+S175P+F180Y+G182A+L184F+Q198E, S27K+N109K+S111E+S173P+G174K+S175P+F180Y+G182A+L184F+N199K, S27K+N109K+S111E+S173P+G174K+S175P+F180Y+G182A+Q198E+N199K, S27K+N109K+S111E+S173P+G174K+S175P+F180Y+L184F+Q198E+N199K, S27K+N109K+S111E+S173P+G174K+S175P+G182A+L184F+Q198E+N199K, S27K+N109K+S111E+S173P+G174K+F180Y+G182A+L184F+Q198E+N199K, S27K+N109K+S111E+S173P+S175P+F180Y+G182A+L184F+Q198E+N199K, S27K+N109K+S1E+G174K+S175P+F180Y+G182A+L184F+Q198E+N199K, S27K+N109K+S171E+S173P+G174K+S175P+F180Y+G182A+L184F+Q198E, S27K+N109K+S171E+S173P+G174K+S175P+F180Y+G182A+L184F+N199K, S27K+N109K+S171E+S173P+G174K+S175P+F180Y+G182A+Q198E+N199K, S27K+N109K+S171E+S173P+G174K+S175P+F180Y+L184F+Q198E+N199K, S27K+N109K+S171E+S173P+G174K+S175P+G182A+L184F+Q198E+N199K, S27K+N109K+S171E+S173P+G174K+F180Y+G182A+L184F+Q198E+N199K, S27K+N109K+S171E+S173P+S175P+F180Y+G182A+L184F+Q198E+N199K, S27K+N109K+S171E+G174K+S175P+F180Y+G182A+L184F+Q198E+N199K, S27K+N109K+S173P+G174K+S175P+F180Y+G182A+L184F+Q198E+N199K, S27K+S111E+S171E+S173P+G174K+S175P+F180Y+G182A+L184F+Q198E, S27K+S111E+S171E+S173P+G174K+S175P+F18Y+G182A+L184F+N199K, S27K+S111E+S171E+S173P+G174K+S175P+F180Y+G182A+Q198E+N199K, S27K+S111E+S171E+S173P+G174K+S175P+F18Y+L184F+Q198E+N199K, S27K+S111E+S171E+S173P+G174K+S175P+G182A+L184F+Q198E+N199K, S27K+S111E+S171E+173P+G174K+F180Y+G182A+L184F+Q198E+N199K, S27K+S111E+S171E+S173P+S175P+F180Y+G182A+L184F+Q198E+N199K, S27K+S111E+S171E+G174K+S175P+F180Y+G182A+L184F+Q198E+N199K, S27K+S111E+S173P+G174K+S175P+F180Y+G182A+L184F+Q198E+N199K, S27K+S171E+S173P+G174K+S175P+F180Y+G182A+L184F+Q198E+N199K, N109K+S111E+S171E+S173P+G174K+S175P+F180Y+G182A+L184F+Q198E, N109K+S111E+S171E+S173P+G174K+S175P+F18Y+G182A+L184F+N199K, N109K+S111E+S171E+S173P+G174K+175P+F18Y+G182A+Q198E+N199K, N109K+S111E+S171E+S173P+G174K+S175P+F180Y+L184F+Q198E+N199K, N109K+S111E+S171E+S173P+G174K+S175P+G182A+L184F+Q198E+N199K, N109K+S111E+S171E+S173P+G174K+F180Y+G182A+L184F+Q198E+N199K, N109K+S111E+S171E+S173P+S175P+F180Y+G182A+L184F+Q198E+N199K, N109K+S111E+S171E+G174K+S175P+F180Y+G182A+L184F+Q198E+N199K, N109K+S111E+S173P+G174K+S175P+F180Y+G182A+L184F+Q198E+N199K, N109K+S171E+S173P+G174K+S175P+F180Y+G182A+L184F+Q198E+N199K and S111E+S171E+S173P+G174K+S175P+F180Y+G182A+L184F+Q198E+N199K An embodiment of the invention relates to a feed additive comprising an S8 protease having at least 90% identity to a polypeptide selected from the group consisting of SEQ ID NO:1, SEQ ID NO:2 and SEQ ID NO:3, typically SEQ ID NO:2 and SEQ ID NO:3, wherein the polypeptide comprises none, one or more of the mutations selected from the group consisting of S27K+N109K+S111E+S171E+S173P+G174K+S175P+F180Y+G182A+L184F+Q198E, S27K+N109K+S111E+S171E+S173P+G174K+S175P+F180Y+G182A+L184F+N199K, S27K+N109K+S111E+S171E+S173P+G174K+S175P+F180Y+G182A+Q198E+N199K, S27K+N109K+S111E+S171E+S173P+G174K+S175P+F180Y+L184F+Q198E+N199K, S27K+N109K+S111E+S171E+S173P+G174K+S175P+G182A+L184F+Q198E+N199K, S27K+N109K+S111E+S171E+S173P+G174K+F180Y+G182A+L184F+Q198E+N199K, S27K+N109K+S111E+S173P+G174K+S175P+F180Y+G182A+L184F+Q198E+N199K, S27K+N109K+S171E+S173P+G174K+S175P+F180Y+G182A+L184F+Q198E+N199K, S27K+S111E+S171E+S173P+G174K+S175P+F180Y+G182A+L184F+Q198E+N199K and N109K+S111E+S171E+S173P+G174K+S175P+F180Y+G182A+L184F+Q198E+N199K.

In an embodiment to any part of the third aspect, the polypeptide (or variant) comprises one or more motifs TGXK[V/T][I/V]X[N/S]MSLG (SEQ ID NO: 4). In an embodiment to any part of the third aspect, the polypeptide (or variant) is obtained or obtainable from the taxonomic order Bacillales, preferably the taxonomic family Bacillaceae, or more preferably the taxonomic genus *Bacillus*.

In an embodiment to any part of the third aspect, the polypeptide (or variant) has at least 40%, such as at least 50%, at least 60%, at least 70%, at least 75%, at least 80%, at least 85%, at least 90%, at least 95% or at least 100% of the protease activity of the polypeptide of SEQ ID NO: 1. In an embodiment to any part of the third aspect, the polypeptide (or variant) improves the ileal nitrogen digestibility by at least 1%, such as at least 1.5%, at least 2.0%, least 2.5%, at least 3.0%, least 3.5%, or at least 4.0% compared to negative control where no protease (variant) is added to the diet.

The animal feed additive of any of aspects one, two or three may further comprise one or more components selected from the list consisting of: one or more formulating agents; one or more additional enzymes; one or more microbes; one or more vitamins; one or more minerals; one or more amino acids; one or more prebiotics; one or more phytogenics; one or more organic acids; and one or more other feed ingredients.

The animal feed additive of any of aspects one, two or three may further comprise one or more formulating agents, as discussed below in the formulation section. Preferred formulating agents are glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

The animal feed additive of any of aspects one, two or three may further comprise one or more additional enzymes, as discussed below in the enzyme section. Preferred enzymes are acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The animal feed additive of any of aspects one, two or three may further comprise one or more microbes, as discussed below in the probiotics section. Preferred microbes are from *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp., *Streptococcus* sp. or any combination thereof.

The animal feed additive of any of aspects one, two or three may further comprise one or more vitamins, as discussed below in the vitamins and minerals section. The animal feed additive of any of aspects one, two or three may further comprise one or more minerals, as discussed below in the vitamins and minerals section. The animal feed additive of any of aspects one, two or three may further comprise one or more amino acids, as discussed below in the amino acids section. The animal feed additive of any of aspects one, two or three may further comprise one or more prebiotics, as discussed below in the prebiotics section. The animal feed additive of any of aspects one, two or three may further comprise one or more phytogenics, as discussed below in the phytogenics section. The animal feed additive of any of aspects one, two or three may further comprise one or more organic acids, as discussed below in the organic acids section.

In one embodiment, the S8 protease in the animal feed additive is formulated as a granule. In one embodiment, the S8 protease in the animal feed additive is formulated as a granule, wherein the granule comprises a core particle and one or more coatings. In one embodiment, the S8 protease in the animal feed additive is formulated as a granule comprising a core particle and one or more coatings, wherein the coating comprises a salt and/or wax and/or flour.

In one embodiment, the animal feed additive is in the form of a liquid formulation. In one embodiment, the animal feed additive is in the form of a liquid formulation, wherein the S8 protease is dosed between 0.001% to 25% w/w of the liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

In one embodiment, the animal feed additive is in the form of a liquid formulation, wherein the liquid formulation comprises 20% to 80% w/w polyol. In one embodiment, the animal feed additive is in the form of a liquid formulation comprising 20% to 80% w/w of polyol, wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600 or any combination thereof.

In one embodiment, the animal feed additive is in the form of a liquid formulation, wherein the liquid formulation comprises 0.01% to 2.0% w/w preservative. In one embodiment, the animal feed additive is in the form of a liquid formulation comprising 0.01% to 2.0% w/w preservative, wherein the preservative is selected from the group consisting of sodium sorbate, potassium sorbate, sodium benzoate and potassium benzoate or any combination thereof.

In one embodiment, the animal feed additive is in the form of a liquid formulation comprising:

(A) 0.001% to 25% w/w of an S8 protease of the invention (as described in aspects one, two or three above);

(B) 20% to 80% w/w of polyol;

(C) 0.001% to 2.0% w/w preservative; and (D) water.

Preferred examples of polyols and preservatives are described in the paragraphs below.

Granules Comprising Polypeptides Having Protease Activity

In a fourth aspect, the invention relates to a granule comprising one or more polypeptides having protease activity, wherein the polypeptide is an S8 protease selected from the group consisting of:

(a) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;

(b) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2;

(c) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;

(d) a variant of SEQ ID NO: 1, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(e) a variant of SEQ ID NO: 2, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(f) a variant of SEQ ID NO: 3, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(g) a polypeptide comprising the polypeptide of (a), (b), (c), (d), (e) or (f) and an N-terminal and/or C-terminal His-tag and/or HQ-tag;

(h) a polypeptide comprising the polypeptide of (a), (b), (c), (d), (e) or (f) and an N-terminal and/or C-terminal extension of up to 10 amino acids, e.g., 1, 2, 3, 4, 5, 6, 7, 8, 9 or 10 amino acids; and (i) a fragment of the polypeptide of (a), (b), (c), (d), (e) or (f) having protease activity and having at least 90% of the length of the mature polypeptide.

In an embodiment to any part of the fourth aspect, the polypeptide (or variant) comprises one or more motifs TGXK[V/T][I/V]X[N/S]MSLG (SEQ ID NO: 4). In an embodiment to any part of the fourth aspect, the polypeptide (or variant) is obtained or obtainable from the taxonomic order Bacillales, preferably the taxonomic family Bacillaceae, or more preferably the taxonomic genus *Bacillus*.

In an embodiment to any part of the fourth aspect, the polypeptide (or variant) has at least 40%, such as at least 50%, at least 60%, at least 70%, at least 75%, at least 80%, at least 85%, at least 90%, at least 95% or at least 100% of the protease activity of the polypeptide of SEQ ID NO: 1. In an embodiment to any part of the fourth aspect, the polypeptide (or variant) improves the ileal nitrogen digestibility by at least 1%, such as at least 1.5%, at least 2.0%, least 2.5%, at least 3.0%, least 3.5%, or at least 4.0% compared to negative control where no protease (variant) is added to the diet.

In an embodiment of the fourth aspect, the granule comprises a core particle and one or more coatings. In an embodiment, the granule comprises a core particle and one or more coatings, wherein the coating comprises a salt and/or wax and/or flour.

The granule of the fourth aspect may further comprise one or more components selected from the group consisting of: one or more formulating agents; one or more additional enzymes; one or more microbes; one or more vitamins; one or more minerals; one or more amino acids; one or more prebiotics; one or more phytogenics; one or more organic acids; and one or more other feed ingredients.

The granule of the fourth aspect may further comprise one or more formulating agents, as discussed below in the formulation section. Preferred formulating agents are glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

The granule of the fourth aspect may further comprise one or more additional enzymes, as discussed below in the enzyme section. Preferred enzymes are acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The granule of the fourth aspect may further comprise one or more microbes, as discussed below in the probiotics section. Preferred microbes are from *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp., *Streptococcus* sp. or any combination thereof.

The granule of the fourth aspect may further comprise one or more vitamins, as discussed below in the vitamins and minerals section. The granule of the fourth aspect may further comprise one or more minerals, as discussed below in the vitamins and minerals section. The granule of the fourth aspect may further comprise one or more amino acids, as discussed below in the amino acids section. The granule of the fourth aspect may further comprise one or more prebiotics, as discussed below in the prebiotics section. The granule of the fourth aspect may further comprise one or more phytogenics, as discussed below in the phytogenics section. The granule of the fourth aspect may further comprise one or more organic acids, as discussed below in the organic acids section.

Liquid Formulations Comprising Polypeptides Having Protease Activity

In a fifth aspect, the present invention relates to liquid formulations comprising:

(A) 0.001% to 25% w/w of one or more polypeptides having protease activity, wherein the polypeptide is an S8 protease selected from the list consisting of:
 (a) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
 (b) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2;
 (c) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;
 (d) a variant of SEQ ID NO: 1, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (e) a variant of SEQ ID NO: 2, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (f) a variant of SEQ ID NO: 3, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(g) a polypeptide comprising the polypeptide of (a), (b), (c), (d), (e) or (f) and an N-terminal and/or C-terminal His-tag and/or HQ-tag;
(h) a polypeptide comprising the polypeptide of (a), (b), (c), (d), (e) or (f) and an N-terminal and/or C-terminal extension of up to 10 amino acids, e.g., 1, 2, 3, 4, 5, 6, 7, 8, 9 or 10 amino acids; and
(i) a fragment of the polypeptide of (a), (b), (c), (d), (e) or (f) having protease activity and having at least 90% of the length of the mature polypeptide; and
(B) water.

In one embodiment of the fifth aspect, the invention relates to liquid formulations comprising:
(A) 0.001% to 25% w/w of one or more polypeptides having protease activity, wherein the polypeptide is an S8 protease selected from the list consisting of:
(a) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2;
(c) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;
(d) a variant of SEQ ID NO: 1, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(e) a variant of SEQ ID NO: 2, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(f) a variant of SEQ ID NO: 3, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(g) a polypeptide comprising the polypeptide of (a), (b), (c), (d), (e) or (f) and an N-terminal and/or C-terminal His-tag and/or HQ-tag;
(h) a polypeptide comprising the polypeptide of (a), (b), (c), (d), (e) or (f) and an N-terminal and/or C-terminal extension of up to 10 amino acids, e.g., 1, 2, 3, 4, 5, 6, 7, 8, 9 or 10 amino acids; and
(i) a fragment of the polypeptide of (a), (b), (c), (d), (e) or (f) having protease activity and having at least 90% of the length of the mature polypeptide;
(B) 20% to 80% w/w of polyol;
(C) optionally 0.001% to 2.0% w/w preservative; and
(D) water.

In one embodiment of the fifth aspect, the invention relates to liquid formulations comprising:
(A) 0.001% to 25% w/w of one or more polypeptides having protease activity, wherein the polypeptide is an S8 protease selected from the list consisting of:
(a) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2;
(c) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;
(d) a variant of SEQ ID NO: 1, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(e) a variant of SEQ ID NO: 2, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(f) a variant of SEQ ID NO: 3, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(g) a polypeptide comprising the polypeptide of (a), (b), (c), (d), (e) or (f) and an N-terminal and/or C-terminal His-tag and/or HQ-tag;
(h) a polypeptide comprising the polypeptide of (a), (b), (c), (d), (e) or (f) and an N-terminal and/or C-terminal extension of up to 10 amino acids, e.g., 1, 2, 3, 4, 5, 6, 7, 8, 9 or 10 amino acids; and
(i) a fragment of the polypeptide of (a), (b), (c), (d), (e) or (f) having protease activity and having at least 90% of the length of the mature polypeptide;
(B) 0.001% to 2.0% w/w preservative;
(C) optionally 20% to 80% w/w of polyol; and
(D) water.

In an embodiment to any part of the fifth aspect, the polypeptide (or variant) comprises one or more motifs TGXK[V/T][IN/V]X[N/S]MSLG (SEQ ID NO: 4). In an embodiment to any part of the fifth aspect, the polypeptide (or variant) is obtained or obtainable from the taxonomic order Bacillales, preferably the taxonomic family Bacillaceae, or more preferably the taxonomic genus *Bacillus*.

In an embodiment to any part of the fifth aspect, the polypeptide (or variant) has at least 40%, such as at least 50%, at least 60%, at least 70%, at least 75%, at least 80%, at least 85%, at least 90%, at least 95% or at least 100% of the protease activity of the polypeptide of SEQ ID NO: 1. In an embodiment to any part of the fifth aspect, the polypeptide (or variant) improves the ileal nitrogen digestibility by at least 1%, such as at least 1.5%, at least 2.0%, least 2.5%, at least 3.0%, least 3.5%, or at least 4.0% compared to negative control where no protease (variant) is added to the diet.

In one embodiment to any part of the fifth aspect, the liquid formulation comprises one or more polyols, preferably a polyol selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the fifth aspect, the liquid formulation comprises 20%-80% polyol (i.e., total amount of polyol), preferably 25%-75% polyol, more preferably 30%-70% polyol, more preferably 35%-65% polyol or most preferably 40%-60% polyol. In one embodiment to any part of the fifth aspect, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600. In one embodiment to any part of the fifth aspect, the liquid formulation comprises 20%-80% polyol (i.e., total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment to any part of the fifth aspect, the preservative is selected from the group consisting of sodium sorbate, potassium sorbate, sodium benzoate and potassium benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e., total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassium benzoate or any combination thereof.

In one embodiment to any part of the fifth aspect, the S8 protease is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

The liquid formulation of any of part of the fifth aspect may further comprise one or more components selected from the list consisting of: one or more formulating agents; one or more additional enzymes; one or more microbes; one or more vitamins; one or more minerals; one or more amino acids; one or more prebiotics; one or more phytogenics; one or more organic acids; and one or more other feed ingredients.

In one embodiment to any part of the fifth aspect, the liquid formulation comprises one or more formulating agents (such as those described herein), preferably a formulating agent selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1,2-propylene glycol, 1,3-propylene glycol, sodium sulfate, dextrin, cellulose, sodium thiosulfate, kaolin and calcium carbonate.

In one embodiment to any part of the fifth aspect, the liquid formulation comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectin esterase, triacylglycerol lipase, xylanase, beta-xylosidase or any combination thereof.

In one embodiment to any part of the fifth aspect, the liquid formulation comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

The liquid formulation of any of part of the fifth aspect may further comprise one or more vitamins, as discussed below in the vitamins and minerals section. The liquid formulation of any part of the fifth aspect may further comprise one or more minerals, as discussed below in the vitamins and minerals section. The liquid formulation of any part of the fifth aspect may further comprise one or more amino acids, as discussed below in the amino acids section. The liquid formulation of any of part of the fifth aspect may further comprise one or more prebiotics, as discussed below in the prebiotics section. The liquid formulation of any part of the fifth aspect may further comprise one or more phytogenics, as discussed below in the phytogenics section. The liquid formulation of any part of the fifth aspect may further comprise one or more organic acids, as discussed below in the organic acids section.

Properties pH-Activity

The pH-activity profile of the protease may be determined as described in the kinetic Suc-AAPF-pNA assay. Activity at a lower pH (e.g., 4-7) can be advantageous for the digestion of proteins in an animal.

pH-Stability

The pH-stability profile of the protease may be determined as described in the kinetic Suc-AAPF-pNA assay. Stability at a lower pH (e.g., pH 3) can be advantageous for the protease to survive the conditions of the GI tract of the animal.

Thermostability

Thermostability may be determined as described in Example 5, i.e., using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 1, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 1.

In still further particular embodiments, the thermostable protease of the invention has a melting temperature, $T_m$ (or a denaturation temperature, $T_d$), as determined using Differential Scanning Calorimetry (DSC) as described in example 5 (i.e., in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 6 by determining the residual activity of protease molecules after steam treatment at 85° C. or 90° C. for a short time.

Pelleting Stability

Pelleting stability may be determined as described in Example 7 by using enzyme granulate pre-mixed with feed. From the mixer, the feed is conditioned with steam to 95° C. After conditioning the feed is pressed to pellets and the residual activity determined.

Sources of Polypeptides Having Protease Activity

A polypeptide having protease activity according to the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a polypeptide having protease activity from a gram-positive bacterium within a phylum such as Actinobacteria or from a gram-negative bacterium within a phylum such as Proteobacteria.

In one aspect, the polypeptide is a protease from a bacterium of the order Bacillales, or from the family Bacillaceae, or from the genera *Bacillus*.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* or a related organism from Bacillales, and thus, for example, may be an allelic or species variant of the polypeptide encoding region of the polynucleotide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J.*

*Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; (b) optionally isolating the polypeptide; and (c) recovering the polypeptide. In one aspect, the cell is a *Bacillus* cell. In another aspect, the cell is a *Bacillus horneckiae* cell.

The present invention also relates to methods of producing a polypeptide of the present invention, said method comprising the steps of:

(a) cultivating a recombinant *Bacillus* host cell comprising an exogenous polynucleotide encoding the polypeptide of the present invention, wherein the polynucleotide is expressed and the polypeptide is produced;

(b) optionally isolating the polypeptide; and (c) optionally recovering the polypeptide.

In an embodiment, the recombinant *Bacillus* host cell is selected from the list consisting of *Bacillus alkalophilus, Bacillus amyloliquefaciens, Bacillus brevis, Bacillus circu-*

*lans, Bacillus clausii, Bacillus coagulans, Bacillus firmus, Geobacillus stearothermophilus, Bacillus lautus, Bacillus lentus, Bacillus licheniformis, Bacillus megaterium, Bacillus pumilus, Bacillus stearothermophilus, Bacillus subtilis*, and *Bacillus thuringiensis*. In a preferred embodiment, the recombinant *Bacillus* host cell is selected from the list consisting of *Bacillus licheniformis, Bacillus amyloliquefaciens*, and *Bacillus subtilis*.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells.

In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the protease activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

Formulation

The enzyme of the invention may be formulated as a liquid or a solid. For a liquid formulation, the formulating agent may comprise a polyol (such as, e.g., glycerol, ethylene glycol or propylene glycol), a salt (such as, e.g., sodium chloride, sodium benzoate, potassium sorbate) or a sugar or sugar derivative (such as, e.g., dextrin, glucose, sucrose, and sorbitol). Thus, in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g., as disclosed in WO 00/70034). The formulating agent may comprise a salt (organic or inorganic zinc, sodium, potassium or calcium salts such as, e.g., such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol).

In one embodiment, the composition is a solid composition, such as a spray dried composition, comprising the protease of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the protease of the invention optionally combined with one or more additional enzymes. The granule is composed of a core, and optionally one or more coatings (outer layers) surrounding the core.

Typically, the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. U.S. Pat. Nos. 4,016,040 and 4,713,245 also relate to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme, fillers and binders etc. are mixed with cellulose fibers to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled.

Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes, it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fiber materials (cellulose or synthetic fibers), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol), sugar or sugar derivative (such as, e.g., sucrose, dextrin, glucose, lactose, sorbitol), small organic molecules, starch, flour, cellulose and minerals and clay minerals (also known as hydrous aluminum phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In some embodiments, the thickness of the coating is below 100 μm, such as below 60 μm, or below 40 μm.

The coating should encapsulate the core unit by forming a substantially continuous layer. A substantially continuous layer is to be understood as a coating having few or no holes, so that the core unit is encapsulated or enclosed with few or no uncoated areas. In a particular embodiment, the layer or coating should be homogeneous in thickness.

The coating can further contain other materials as known in the art, e.g., fillers, anti-sticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 μm, such as less than 10 μm or less than 5 μm.

The salt coating may comprise a single salt or a mixture of two or more salts. The salt may be water soluble, in particular, having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminum. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 97/05245, WO 98/54980, WO 98/55599, WO 00/70034, WO 2006/034710, WO 2008/017661, WO 2008/017659, WO 00/20569, WO 01/004279, WO 97/05245, WO 00/01793, WO 2003/059086, WO 2003/059087, WO 2007/031483, WO 2007/031485, WO 2007/044968, WO 2013/192043, WO 2014/014647 and WO 2015/197719 or polymer coating such as described in WO 01/00042.

Specific examples of suitable salts are NaCl (CH20° C.=76%), $Na_2CO_3$ (CH20° C.=92%), $NaNO_3$ (CH20° C.=73%), $Na_2HPO_4$ (CH20° C.=95%), $Na_3PO_4$ (CH25° C.=92%), $NH_4Cl$ (CH20° C.=79.5%), $(NH_4)_2HPO_4$ (CH20° C.=93.0%), $NH_4H_2PO_4$ (CH20° C.=93.1%), $(NH_4)_2SO_4$ (CH20° C.=81.1%), KCl (CH20° C.=85%), $K_2HPO_4$ (CH20° C.=92%), $KH_2PO_4$ (CH20° C.=96.5%), $KNO_3$ (CH20° C.=93.5%), $Na_2SO_4$ (CH20° C.=93%), $K_2SO_4$ (CH20° C.=98%), $KHSO_4$ (CH20° C.=86%), $MgSO_4$ (CH20° C.=90%), $ZnSO_4$ (CH20° C.=90%) and sodium citrate (CH25° C.=86%). Other examples include $NaH_2PO_4$, $(NH_4)H_2PO_4$, $CuSO_4$, $Mg(NO_3)_2$, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e., a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the protease of the invention, one or more salt coatings and one or more wax coatings. Examples of enzyme granules with multiple coatings are shown in WO 93/07263, WO 97/23606 and WO 2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:

(a) a core comprising a protease according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed

The present invention also relates to animal feed comprising one or more proteases of the invention. In one embodiment, the invention relates to animal feed comprising the animal feed additive of aspect one, two or three and plant based material. In one embodiment, the invention relates to animal feed comprising the granule of aspect four and plant based material. In one embodiment, the invention relates to animal feed comprising the liquid formulation of aspect five and plant based material.

The invention further relates to pelleted animal feed. The pelleted animal feed may be prepared by pelleting the animal feed as described in the paragraph above. Thus, in one embodiment, the invention relates to pelleted animal feed comprising the animal feed additive of aspect one, two or three and plant based material. In one embodiment, the invention relates to pelleted animal feed comprising the granule of aspect four and plant based material. In one embodiment, the invention relates to pelleted animal feed comprising the liquid formulation of aspect five and plant based material.

In an embodiment, the plant based material comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof. In a preferred embodiment, the plant based material is soybean meal.

Animal feed compositions or diets have a relatively high content of protein. Poultry and pig diets can be characterized as indicated in Table B of WO 01/58275, columns 2-3. Fish diets can be characterized as indicated in column 4 of this Table B. Furthermore, such fish diets usually have a crude fat content of 200-310 g/kg.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolizable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In an embodiment, the vegetable protein source is material from one or more plants of the family Fabaceae, e.g., soybean, lupine, pea, or bean. In another embodiment, the vegetable protein source is material from one or more plants of the family Chenopodiaceae, e.g., beet, sugar beet, spinach or quinoa. Other examples of vegetable protein sources are rapeseed, and cabbage. In another embodiment, soybean is a preferred vegetable protein source. Other examples of vegetable protein sources are cereals such as barley, wheat, rye, oat, maize (corn), rice, and sorghum.

Animal diets can, e.g., be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) protease/enzyme preparation may also be added before or during the feed ingredient step. Typically, a liquid protease/enzyme preparation comprises the protease of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the protease can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10; —all these ranges being in mg protease protein per kg feed (ppm).

For determining mg protease protein per kg feed, the protease is purified from the feed composition, and the specific activity of the purified protease is determined using a relevant assay (see under protease activity). The protease activity of the feed composition as such is also determined using the same assay, and on the basis of these two determinations, the dosage in mg protease protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg protease protein in feed additives. Of course, if a sample is available of the protease used for preparing the feed additive or the feed, the specific activity is determined from this sample (no need to purify the protease from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, 2000, The ENZYME database, *Nucleic Acids Res.* 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al., "The carbohydrate-active enzymes database (CAZy) in 2013", *Nucl. Acids Res.* (1 Jan. 2014) 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolase (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), beta-glucanase (EC 3.2.1.6), beta-glucosidase (EC 3.2.1.21), triacylglycerol lipase (EC 3.1.1.3), lysophospholipase (EC 3.1.1.5), lysozyme (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), protease (EC 3.4), pullulanase (EC 3.2.1.41), pectin esterase (EC 3.1.1.11), xylanase (EC 3.2.1.8, EC 3.2.1.136), beta-xylosidase (EC 3.2.1.37), or any combination thereof.

In an embodiment, the composition of the invention comprises a galactanase (EC 3.2.1.89) and a beta-galactosidase (EC 3.2.1.23).

In an embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), Ave-Mix® Phytase (Aveve Biochem), Phyzyme® XP (Verenium/DuPont) and Axtra® PHY (DuPont). Other preferred phytases include those described in, e.g., WO 98/28408, WO 00/43503, and WO 03/066847.

In an embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In an embodiment, the composition of the invention comprises a protease (EC 3.4). Examples of commercially available proteases include Ronozyme® ProAct (DSM Nutritional Products), Winzyme Pro Plus® (Suntaq International Limited) and Cibenza® DP100 (Novus International).

In an embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio@ Excel or Rovabio® Advance (Adisseo), Endofeed® DC (Endo-1,3(4)-β-glucanase and endo-1,4-β-xylanase, Andres Pintaluba SA) or Amylofeed@ (endo-1,3(4)-β-glucanase and endo-1,4-β-xylanase and α-amylase, Andres Pintaluba SA).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In an embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In an embodiment, the animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In an embodiment, the composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSAO1 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In an embodiment, the composition, animal feed additive or animal feed further comprises a bacterium from one or more of the following strains of *Bacillus pumilus*: NRRL B-50016, ATCC 700385, NRRL B-50885 or NRRL B-50886.

In an embodiment, the composition, animal feed additive or animal feed further comprises a bacterium from one or more of the following strains of *Bacillus lichenformis*: NRRL B-50015, NRRL B-50621 or NRRL B-50623.

In an embodiment, the composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1\times10^{11}$ CFU/kg of dry matter. In an embodiment, the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In an embodiment, the bacterial count of each of the bacterial strains in the animal feed composition is between $1\times10^9$ and $1\times10^{11}$ CFU/animal/day. In one embodiment, the amount of probiotics is 0.001% to 10% by weight of the composition.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharides, yeast beta-glucans or protein contents and are normally derived from the cell wall of the yeast, *Saccharomyces cerevisiae*.

In one embodiment, the amount of prebiotics is 0.001% to 10% by weight of the composition. Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

In one embodiment, the amount of phytogeneics is 0.001% to 10% by weight of the composition. Examples of commercial products are Crina® (DSM Nutritional Products); Cinergy™, Biacid™, ProHacid™ Classic and ProHacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are short chain fatty acids (e.g., formic acid, acetic acid, propionic acid, butyric acid), medium chain fatty acids (e.g., caproic acid, caprylic acid, capric acid, lauric acid), di/tri-carboxylic acids (e.g., fumaric acid), hydroxy acids (e.g., lactic acid), aromatic acids (e.g., benzoic acid), citric acid, sorbic acid, malic acid, and tartaric acid or their salt (typically sodium or potassium salt such as potassium diformate or sodium butyrate).

In one embodiment, the amount of organic acid is 0.001% to 10% by weight of the composition. Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan. In one embodiment, the amount of amino acid is 0.001% to 10% by weight of the composition.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

In one embodiment, the amount of vitamins is 0.001% to 10% by weight of the composition. In one embodiment, the amount of minerals is 0.001% to 10% by weight of the composition.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise coloring agents, stabilizers, growth improving additives and aroma compounds/flavorings, polyunsaturated fatty acids (PUFAs); reactive oxygen generating species, antioxidants, anti-microbial peptides, anti-fungal polypeptides and mycotoxin management compounds.

Examples of coloring agents are carotenoids such as beta-carotene, astaxanthin, and lutein.

Examples of aroma compounds/flavorings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/90384.

Examples of polyunsaturated fatty acids are C18, C20 and C22 polyunsaturated fatty acids, such as arachidonic acid, docosohexenoic acid, eicosapentenoic acid and gamma-linoleic acid.

Examples of reactive oxygen generating species are chemicals such as perborate, persulphate, or percarbonate; and enzymes such as an oxidase, an oxygenase or a synthetase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in negative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Methods of Preparing an Animal Feed

The invention further relates to a method of preparing an animal feed, comprising mixing the animal feed additive of aspect one, two or three with at least one protein or protein source. The invention further relates to a method of preparing an animal feed, comprising mixing the granule of aspect four with at least one protein or protein source. The invention further relates to a method of preparing an animal feed, comprising mixing the liquid formulation of aspect five with at least one protein or protein source.

In an embodiment, the protein or protein source comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof. In a preferred embodiment, the protein or protein source is soybean meal.

The invention further relates to a method of preparing an animal feed comprising applying the liquid formulation of aspect five onto plant based material. In one embodiment, the liquid formulation is applied via a spray. In a further embodiment, the plant based material comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof. In a preferred embodiment, the plant based material is soybean meal.

Methods of Improving Animal Performance

The invention further relates to a method of improving one or more performance parameters of an animal, comprising administering to one or more animals the animal feed additive of aspect one, two or three. The invention further relates to a method of improving one or more performance parameters of an animal, comprising administering to one or more animals the granule of aspect four. The invention further relates to a method of improving one or more performance parameters of an animal, comprising administering to one or more animals the liquid formulation of aspect five.

In one embodiment, an animal feed is prepared from the animal feed additive, granule or liquid formulation as described herein and administered to the animal. The invention further relates to a method of improving one or more performance parameters of an animal, comprising administering to one or more animals an animal feed or pelleted animal feed comprising the S8 protease of the invention.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

Method for Improving the Nutritional Value of Animal Feed

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e., the weight of ingested feed relative to weight gain) of the animal might be improved.

Thus, the invention further relates to a method of improving the nutritional value of an animal feed, comprising adding the animal feed additive of aspect one, two or three to the feed. Thus, the invention further relates to a method of improving the nutritional value of an animal feed, comprising adding the granule of aspect four to the feed. Thus, the invention further relates to a method of improving the nutritional value of an animal feed, comprising adding the liquid formulation of aspect five to the feed.

In an embodiment, the feed comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof. In a preferred embodiment, feed comprises soybean meal.

Uses

The present invention is also directed to methods for using the polypeptides having protease activity, or compositions thereof, for, e.g., animal feed.

Use in Animal Feed

A protease of the invention may also be used in animal feed. In an embodiment, the present invention provides a method for preparing an animal feed composition comprising adding one or more proteases of the present invention to one or more animal feed ingredients.

The one or more proteases of the present invention may also be used in animal feed as feed enhancing enzymes that improve feed digestibility to increase the efficiency of its utilization according to WO 00/21381 and WO 2004/026334.

In a further embodiment, a protease of the present invention may be used in an animal feed or as a feed additive, where it may provide a positive effect on the animal's digestive tract and in this way improve animal performance in accordance to weight gain, feed conversion ratio (FCR), European Production Efficiency Factor (EPEF), European Production Efficacy Factor (EFF) or improved animal health such as decreased mortality rate. FCR is calculated as the feed intake in g/animal relative to the weight gain in g/animal.

In the use according to the invention the proteases can be fed to the animal before, after, or simultaneously with the diet. The latter is preferred.

In an embodiment, the form of the protease when it is added to the feed or when it is included in a feed additive is well-defined. Well-defined means that the protease preparation is at least 50% pure as determined by Size-exclusion chromatography (see Example 12 of WO 01/58275). In other embodiments, the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimizing dosage based upon the desired effect.

For the use in animal feed, however, the protease need not be pure; it may, e.g., include other enzymes, in which case it could be termed a protease preparation.

The protease preparation can be (a) added directly to the feed, or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In an embodiment, the vegetable protein source is material from one or more plants of the family Fabaceae, e.g., soybean, lupine, pea, or bean.

In another embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In an embodiment of a treatment process the protease(s) in question is affecting (or acting on, or exerting its hydrolyzing or degrading influence on) the proteins, such as vegetable proteins or protein sources. To achieve this, the protein or protein source is typically suspended in a solvent, e.g., an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g., by a heat-treatment step.

In another embodiment of a treatment process of the invention, the protease action is sustained, meaning, e.g., that the protease is added to the proteins, but its hydrolyzing influence is so to speak not switched on until later when desired, once suitable hydrolyzing conditions are established, or once any enzyme inhibitors are inactivated, or whatever other means could have been applied to postpone the action of the enzyme.

In one embodiment, the treatment is a pre-treatment of animal feed or proteins for use in animal feed, i.e., the proteins are hydrolyzed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e., the weight of ingested feed relative to weight gain) of the animal might be improved.

The protease can be added to the feed in any form, be it as a relatively pure protease or in admixture with other components intended for addition to animal feed, i.e., in the form of animal feed additives, such as the so-called pre-mixes for animal feed.

Suitable Embodiments of the Invention

Preferred embodiments of the invention are described in the set of items below.

1. An animal feed additive comprising one or more vitamins and one or more polypeptides having protease activity, wherein the polypeptide is an S8 protease selected from the group consisting of: (a) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;

(b) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2;

(c) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;

(d) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;

(e) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;

(f) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6;

(g) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7;

(h) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8;

(i) a polypeptide having at least 75%, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;

(j) a variant of SEQ ID NO: 1, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(k) a variant of SEQ ID NO: 2, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(l) a variant of SEQ ID NO: 3, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a variant of SEQ ID NO: 5, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(n) a variant of SEQ ID NO: 6, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(o) a variant of SEQ ID NO: 7, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(p) a variant of SEQ ID NO: 8, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(q) a variant of SEQ ID NO: 9, wherein the variant has protease activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(r) a polypeptide comprising the polypeptide of (a), (b), (c), (d), (e), (f), (g), (h), or (i) and an N-terminal and/or C-terminal His-tag and/or HQ-tag;

(s) a polypeptide comprising the polypeptide of (a), (b), (c), (d), (e), (f), (g), (h), or (i) and an N-terminal and/or C-terminal extension of up to 10 amino acids, e.g., 1, 2, 3, 4, 5, 6, 7, 8, 9 or 10 amino acids; and (t) a fragment of the polypeptide of (a), (b), (c), (d), (e), (f), (g), (h), or (i) having protease activity and having at least 90% of the length of the mature polypeptide.

2. The animal feed additive of item 1, wherein the S8 protease is obtained or obtainable from the taxonomic order Bacillales, preferably the taxonomic family Bacillaceae, or more preferably the taxonomic genus *Bacillus*.

3. The animal feed additive of any of items 1 to 2, wherein the S8 protease comprises the motif TGXK[V/T][I/V]X[N/S]MSLG (SEQ ID NO: 4).

4. The animal feed additive of any of items 1 to 3, wherein the animal feed additive does not comprise a surfactant.

5. The animal feed additive of any of items 1 to 4, wherein the S8 protease has at least 40%, such as at least 50%, at least 60%, at least 70%, at least 75%, at least 80%, at least 85%, at least 90%, at least 95% or at least 100% of the protease activity of the polypeptide of SEQ ID NO: 1.

6. The animal feed additive of any of items 1 to 4, wherein the S8 protease improves the ileal nitrogen digestibility by at least 1%, such as at least 1.5%, at least 2.0%, least 2.5%, at least 3.0%, least 3.5%, or at least 4.0% compared to negative control.

7. The animal feed additive of any of items 1 to 6, wherein the polypeptide comprises or consists of amino acids 1 to 314 of SEQ ID NO: 1, amino acids 1 to 311 of SEQ ID NO: 2 or amino acids 1 to 311 of SEQ ID NO: 3.

8. The animal feed additive of any of items 1 to 7, further comprising one or more components selected from the list consisting of:
one or more vitamins;
one or more minerals;
one or more amino acids;
one or more prebiotics;
one or more phytogenics;
one or more organic acids; and one or more other feed ingredients.

9. The animal feed additive of any of items 1 to 8, further comprising one or more formulating agents.

10. The animal feed additive of item 9, wherein the one or more formulating agent is selected from the group consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

11. The animal feed additive of any of items 1 to 10, further comprising one or more additional enzymes.

12. The animal feed additive of item 11 wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

13 The animal feed additive of any of items 1 to 12, further comprising one or more microbes.

14. The animal feed additive of item 13, wherein the one or more microbes are selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

15. The animal feed additive of any of items 1 to 14, wherein the S8 protease is formulated as a granule.

16. The animal feed additive of item 15, wherein the granule comprises a core particle and one or more coatings.

17. The animal feed additive of item 16, wherein the coating comprises a salt and/or wax and/or flour.

18. The animal feed additive of any of items 1 to 14, wherein the additive is in the form of a liquid formulation.

19. The animal feed additive of item 18, wherein the S8 protease is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

20. The animal feed additive of item 18 or 19, wherein the formulation further comprises 20% to 80% w/w of polyol.

21. The animal feed additive of item 20, wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600 or any combination thereof.

22. The animal feed additive of any of items 18 to 21, wherein the formulation further comprises 0.01% to 2.0% w/w preservative.

23. The animal feed additive of item 22, wherein the preservative is selected from the group consisting of sodium sorbate, potassium sorbate, sodium benzoate and potassium benzoate or any combination thereof.

24. A granule comprising the animal feed additive of any of items 1 to 14.

25. The granule of item 24, wherein the granule comprises a core particle and one or more coatings.

26. The granule of item 25, wherein the coating comprises a salt and/or wax and/or flour.

27. A liquid formulation comprising the animal feed additive of any of items 1 to 14.

28. The liquid formulation of item 27, wherein the S8 protease is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

29. The liquid formulation of item 27 or 28, wherein the formulation further comprises 20% to 80% w/w of polyol.

30. The liquid formulation of item 29, wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600 or any combination thereof.

31. The liquid formulation of any of items 27 to 30, wherein the formulation further comprises 0.01% to 2.0% w/w preservative.

32. The liquid formulation of item 31, wherein the preservative is selected from the group consisting of sodium sorbate, potassium sorbate, sodium benzoate and potassium benzoate or any combination thereof.

33. A method of preparing an animal feed comprising applying the liquid formulation of any of items 27 to 32 onto plant based material.

34. The method of item 33, wherein the liquid formulation is applied via a spray.

35. The method of item 33 or 34, wherein the plant based material comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

36. The method of any of items 33 to 35, wherein the plant based material is in pelleted form.

37. An animal feed comprising the animal feed additive of any of items 1 to 23, the granule of any of items 24 to 26 or the liquid formulation of any of items 27 to 32 and plant based material.

38. The animal feed of item 37, wherein the plant based material comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

39. A pelleted animal feed prepared using the method of any of items 33 to 36 or by pelleting the animal feed of item 37 or 38.

40. A method of improving one or more performance parameters of an animal comprising administering to one or more animals the animal feed additive of any of items 1 to 23, the granule of any of items 24 to 26, the liquid formulation of any of items 27 to 32, the animal feed of item 37 or 38 or the pelleted animal feed of item 39.

41. The method of item 40, wherein improving the performance of an animal means improved body weight gain, improved European Production Efficiency Factor (EPEF) and/or improved FCR.

42. A method of preparing an animal feed comprising mixing the animal feed additive of any of items 1 to 23, the granule of any of items 24 to 26 or the liquid formulation of any of items 27 to 32 with at least one protein or protein source.

43. A method for the treatment of proteins, comprising the step of adding the animal feed additive of any of items 1 to 23, the granule of any of items 24 to 26 or the liquid formulation of any of items 27 to 32 to at least one protein or protein source.

44. A method for increasing digestibility and/or solubility of protein, comprising mixing the animal feed additive of any of items 1 to 23, the granule of any of items 24 to 26 or the liquid formulation of any of items 27 to 32 with at least one protein or protein source.

45. The method of any of items 40 to 44, wherein the protein or protein source comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

46. A method for improving the nutritional value of an animal feed, comprising adding the animal feed additive of any of items 1 to 23, the granule of any of items 24 to 26 or the liquid formulation of any of items 27 to 32 to the feed.

47. The method of item 46, wherein the animal feed comprises legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

48. Use of the animal feed additive of any of items 1 to 23, the granule of any of items 24 to 26 or the liquid formulation of any of items 27 to 32:
in the preparation of a composition for use in animal feed;
for improving the nutritional value of an animal feed;
for increasing digestible and/or soluble protein in animal feed;
for increasing the degree of hydrolysis of proteins in animal diets;
for improving one or more performance parameters in an animal; and/or for the treatment of proteins.

49. A method of producing a polypeptide, comprising the steps of:
(a) cultivating a recombinant *Bacillus* host cell comprising an exogenous polynucleotide encoding the polypeptide as defined in item 1, wherein the polynucleotide is expressed and the polypeptide is produced; and, optionally
(b) recovering the polypeptide.

50. The method to item 49, wherein the exogenous polynucleotide is integrated into the chromosome of the host cell and operably linked with a promoter.

EXAMPLES

Strains

A *Bacillus horneckiae* strain was isolated from an environmental sample in Turkey on or before 1995 as disclosed in WO 2015/091990.

*Bacillus* sp. TY145 was isolated from a sample of Antarctic soil ca. 1989 as disclosed in WO 92/17577.

Protease Assays

1) Kinetic Suc-AAPF-pNA assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in OD$_{405}$ was monitored as a measure of the protease activity.

2) End Point Suc-AAPF-pNA Assay:
pNA substrate: Suc-AAPF-pNA (Bachem L-1400).
Temperature: controlled (assay temperature).
Assay buffers: 100 mM succinic acid, 100 mM HEPES, 100 mM CHES, 100 mM CABS, 1 mM CaCl$_2$, 150 mM KCl, 0.01% Triton X-100, pH 7.0.

200 µl pNA substrate (50 mg dissolved in 1.0 ml DMSO and further diluted 50× with the Assay buffers) were pipetted in an Eppendorf tube and placed on ice. 20 µl peptidase sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath and adding 600 µl 500 mM succinic acid, pH 3.5. 200 µl supernatant was transferred to a microtiter plate. OD$_{405}$ was read as a measure of peptidase activity. A buffer blind was included in the assay (instead of enzyme).

2) Protazyme AK Assay:
Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM CaCl$_2$, 150 mM KCl, 0.01% Triton X-100, pH 9.0.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath. Then the tube was centrifuged in an ice cold centrifuge for a few minutes and 200 µl supernatant was transferred to a microtiter plate. OD$_{650}$ was read as a measure of protease activity. A buffer blind was included in the assay (instead of enzyme).

3) O-Pthaldialdehyde (OPA) Assay:
This assay detects primary amines and hence cleavage of peptide bonds by a protease can be measured as the difference in absorbance between a protease treated sample and a control sample. The assay was conducted essentially according to Nielsen et al. (Nielsen et al., 2001, "Improved method for determining food protein degree of hydrolysis", *J. Food Sci.* 66: 642-646).

0.5 ml sample was filtered through a PALL 96-well filter plate PN8175 (10 min, 2700 rpm, 5° C.). The samples were diluted appropriately (e.g., 10, 50 or 100 times) in deionized water and 25 µl of each sample was loaded into a 96 well microtiter plate (5 replicates). 200 µl OPA reagent (100 mM di-sodium tetraborate decahydrate, 3.5 mM sodium dodecyl sulphate (SDS), 5.7 mM di-thiothreitol (DDT), 6 mM o-Phthaldialdehyde) was dispensed into all wells, the plate was shaken (60 sec, 650 rpm) and absorbance measured at 340 nm.

Example 1: Expression and Purification of the S8 Protease from *Bacillus horneckiae*

The S8 protease from *Bacillus horneckiae* (SEQ ID NO: 1) was expressed and purified as described in Example 1 of WO 2015/091990. A kinetic Suc-AAPF-pNA assay was used for obtaining the pH-activity profile and the pH-stability profile. An End-point Suc-AAPF-pNA assay was used for obtaining the temp-activity profile at pH 7. Characteristics for the S8 Protease from *Bacillus horneckiae* (SEQ ID NO: 1)

The relative molecular weight as determined by SDS-PAGE was approx. Mr=35 kDa.

The N-terminal sequence determined by EDMAN degradation was: EVTATPS.

The molecular weight of the major peak (ca. 50%) determined by intact molecular weight analysis was 32132.0 Da.

The mature sequence of the major peak (from EDMAN N-terminal sequencing data and intact MS data):

```
                                                     (SEQ ID NO: 1)
EVTATPSTQTPWGIKSIYNDQSITKTTGGSGIKVAVLDTGVHTGHIDL

AGSSEQCKDFTQSNPLVNGSCTDRQGHGTHVAGTVLAHGGSDGQGVYG

VAPQAKLWAYKVLGDNGSGYSDDIAAAIRHVADEASRTGSKVVINMSL
```

-continued

```
GSSGKDSLIASAVDYAYGKGVLIVAAAGNSGSGSNTIGYPAALVNAVA

VAALENVQQNGTYRVANFSSRGNPATAGDFRIQERDVEVSAPGASVES

TWYNGGYNTISGTSMATPHVAGLAAKIWSSNSSLSHSQLRTELQNRAK

VYDIKGGIGAGTGDDYASGFGYPRVK
```

The calculated molecular weight from this mature sequence is 32132.0 Da.

Intact molecular weight analysis showed ca. 10% of the product was amino acids 2-314 and ca. 40% of the product was amino acids 4-314.

Example 2.1: Expression and Purification of the S8 Protease from *Bacillus* sp. TY145

The S8 protease from *Bacillus* sp. TY145 (SEQ ID NO: 2) was expressed and purified as described in Example 1 of WO 92/17577. A kinetic Suc-AAPF-pNA assay was used for obtaining the pH-activity profile and the pH-stability profile. A Protazyme AK assay was used for obtaining the temp-activity profile at pH 9.

Characteristics for the S8 Protease from *Bacillus* sp. TY145 (SEQ ID NO: 2)

The relative molecular weight as determined by SDS-PAGE was approx. Mr=34 kDa.

The N-terminal sequence determined by EDMAN degradation was: AVPSTQT.

The molecular weight determined by intact molecular weight analysis was 31784 Da.

The mature sequence (from EDMAN N-terminal sequencing data and Intact MS data):

```
                                          (SEQ ID NO: 2)
AVPSTQTPWGIKSIYNDQSITKTTGGSGIKVAVLDTGVYTSHLDLAGS

AEQCKDFTQSNPLVDGSCTDRQGHGTHVAGTVLAHGGSNGQGVYGVAP

QAKLWAYKVLGDNGSGYSDDIAAAIRHVADEASRTGSKVVINMSLGSS

AKDSLIASAVDYAYGKGVLIVAAAGNSGSGSNTIGFPGGLVNAVAVAA

LENVQQNGTYRVADFSSRGNPATAGDYIIQERDIEVSAPGASVESTWY

TGGYNTISGTSMATPHVAGLAAKIWSANTSLSHSQLRTELQNRAKVYD

IKGGIGAGTGDDYASGFGYPRVK
```

The calculated molecular weight from this mature sequence is 31783.7 Da.

Intact molecular weight analysis also showed ca. 10% of the product comprised an extra EVT on the N-terminus.

Example 2.2 Expression Example for Five S8 Proteases from *Bacillus* (Homologs of SEQ ID NO: 1)

Five further S8 proteases were expressed in *Bacillus subtilis*. Expression of SEQ ID NO: 5: the S8 protease 1 from *Bacillus* sp-13380 (*Bacillus* sp-1, GENESEQP: BDV61032) is described in WO2017064253-A1. Expression of SEQ ID NO: 6, the S8 protease from *Bacillus idriensis* (GENESEQP:BCB40142). Expression of SEQ ID NO: 7: the S8 protease 2 from *Bacillus* sp-13380 (*Bacillus* sp-1, GENESEQP:BCB40140); Expression of SEQ ID NO: 8, the S8 protease from *Bacillus* sp-62451 (*Bacillus* sp-2, GENESEQP:BCB40144) are described in patent WO2015091989-A1.

Expression of the S8 protease from *Bacillus oceanisediminis* (SEQ ID NO:9) was done in the following way. The gene encoding the S8 proteases *Bacillus oceanisediminis* (SEQ ID NO:10) was codon optimized and synthesized by Integrated DNA Technologies (Interleuvenlaan 12A, B-3001 Leuven, Belgium). The gene was expressed as a secreted enzyme where the genes native secretion signal was replaced with a *Bacillus clausii* secretion signal (SEQ ID NO: 11). The construct was made as a linear integration construct, where the synthetic genes was fused by PCR between two *Bacillus subtilis* homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The SOE PCR method is also described in patent application WO 2003095658. In both constructs the gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The linear PCR construct were transformed into *Bacillus subtilis*. Transformants were selected on LB plates supplemented with 6 µg of chloramphenicol per ml. A recombinant *Bacillus subtilis* clone was grown in liquid culture. The recombinant enzyme was accumulated in the supernatant upon natural cell lysis. The enzyme containing supernatant was harvested and the enzymes purified as described in Example 1.

Example 3: Construction, Expression and Purification of S8 Protease Variant (SEQ ID NO: 3)

A variant of the TY145 protease (SEQ ID NO: 3) was constructed, expressed and purified as described in Example 1 of WO 2016/097354. A kinetic Suc-AAPF-pNA assay was used for obtaining the pH-activity profile and the pH-stability profile. A Protazyme AK assay was used for obtaining the temp-activity profile at pH 9.

Characteristics for the S8 Protease Variant (SEQ ID NO: 3)

The relative molecular weight as determined by SDS-PAGE was approx. Mr=37 kDa.

The N-terminal sequence determined by EDMAN degradation was: AVPSTQT.

The molecular weight determined by intact molecular weight analysis was 32089.1 Da.

The mature sequence (from EDMAN N-terminal sequencing data and Intact MS data):

```
                                          (SEQ ID NO: 3)
AVPSTQTPWGIKSIYNDQSITKTTGGKGIKVAVLDTGVYTSHLDLAGS

AEQCKDFTQSNPLVDGSCTDRQGHGTHVAGTVLAHGGSNGQGVYGVAP

QAKLWAYKVLGDKGEGYSDDIAAAIRHVADEASRTGSKVVINMSLGSS

AKDSLIASAVDYAYGKGVLIVAAAGNEGPKPNTIGYPAGFVNAVAVAA

LENVQEKGTYRVADFSSRGNPATAGDYIIQERDIEVSAPGASVESTWY

TGGYNTISGTSMATPHVAGLAAKIWSANTSLSHSQLRTELQNRAKVYD

IKGGIGAGPGDDYASGFGYPRVK
```

The calculated molecular weight from this mature sequence is 32089.3 Da

Intact molecular weight analysis also showed ca. 10% of the product comprised an extra EVT or VT on the N-terminus.

Example 4: pH Curves on SBM-Maize Slurries

The pH activity curves of the S8 protease of the invention on a maize-soybean meal slurry were determined according to the method below.

Substrate: SBM-maize (30:70)
Temperature: 40° C.
Assay buffers: 100 mM succinic acid, 100 mM HEPES, 100 mM CHES, 100 mM CABS buffer, 12.5 mM $CaCl_2$, 150 mM KCl, 0.01% Triton X-100, adjusted to desired pH (3, 4, 5, 6, 7) with NaOH or HCl To 2 g SBM-maize (30:70) substrate was added 20 ml assay buffer which was adjusted to the desired pH with NaOH or HCl. The slurry was stirred for 5 min and 2 ml portions of the slurry were transferred to each well in a 24 well-plate on a plate mixer with combined heating and magnetic mixing. The samples were preincubated for 30 min at 40° C. The protease was diluted to 100 ul in 100 mM sodium acetate buffer (9.565 g/L NaOAc, 1.75 g/L acetic acid, 5 mM $CaCl_2$, 0.01% BSA, 0.01% Tween20, pH 6.0) to achieve a final concentration of 200 mg EP/kg substrate, and added to the wells. After 3 hours at 40° C. under magnetic stirring, the plate was centrifuged (10 min, 4000 rpm, 0° C.) and the supernatant was analyzed using the OPA (o-phthaldialdehyde) assay. The activity of the proteases is the amount of free α-amino ends as determined by absorbance at 340 nm minus the blank (sample run without enzyme), and is given in Table 4 below.

TABLE 4 pH-activity of different proteases on maize-SBM

| Protease | pH 3 | pH 4 | pH 5 | pH 6 | pH 7 |
|---|---|---|---|---|---|
| Bacillus horneckiae (SEQ ID NO: 1) | 0.01 | 0.15 | 1.38 | 1.5 | 0.94 |
| Bacillus sp. TY145 (SEQ ID NO: 2) | 0.00 | 0.77 | 2.08 | 3.26 | 4.54 |
| Bacillus sp. variant (SEQ ID NO: 3) | 0.00 | 0.69 | 1.28 | 1.96 | 2.76 |

Example 5: Thermostability

An aliquot of the protein sample of protease is either desalted or buffer-exchanged into 20 mM Na-acetate, pH 4.0 using a prepacked PD-10 column or dialyzed against 2×500 ml 20 mM Na-acetate, pH 4.0 at 4° C. in a 2-3 hour step followed by an overnight step. The sample is 0.45 µm filtered and diluted with buffer to approx. 2 A280 units. The dialysis buffer is used as reference in Differential Scanning Calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 6: Steam Stability

The residual activity of the protease after steam treatment may be evaluated using the following assay.

In these experiments, a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, the samples placed on ice, re-suspended and evaluated with respect to protease activity using, e.g., the Suc-AAPF-pNA or o-Phthaldialdehyde (OPA) assay. Each enzyme sample is compared to a similar sample that had not been steam treated in order to calculate residual activity.

Example 7: Pelleting Stability Tests

The enzyme is granulated in a manner as described in U.S. Pat. No. 4,106,991, Example 1. The obtained granulate is dried in a fluid bed to a water content below 1% and sifted to obtain a product with the particle range 250 µm to 850 µm. Finally, the product is coated with palm oil and calcium carbonate in a manner as described in U.S. Pat. No. 4,106, 991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer, the feed is led to the conditioner (a cascade mixer with steam injection) at a rate of approximately 300 kg/hour. The conditioner heats up the feed to 95° C. (measured at the outlet) by injecting steam. The residence time in the conditioner is 30 seconds. From the conditioner, the feed is led to a Simon Heesen press equipped with 3.0×35 mm horizontal die and pressed to pellets with a length of around 15 mm. After the press the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

Example 8: Ileal Nitrogen Digestibility Trial in Broilers Using the S8 Protease from Bacillus Horneckiae (SEQ ID NO: 1)

Animal and Feeding

One day old chickens (Cobb500) obtained from a commercial hatchery (Accouvoir multiplicateur Grelier, La Bohardière, France) were used. The chickens were housed in wire-floor battery cages (0.75 m2/cage, 6 chickens/cage) with ad libitum access to feed and water. The feeding was divided into two phases, Starter and Grower (1-7, and 8-21, respectively) according to the nutritional need of the chickens. Allocation of the chickens into the cages was based on the day 1 body weight, in order to minimize the body weight variations between cages. All birds were subjected to the same feeding strategy during the first 16 days of life followed by a five-day experimental period from days 17-21. During the experimental period, the cages were allocated on either a negative control diet (NC), positive control diet (PC), or enzyme treatment, constructed from the NC sprayed with liquid protease solution, see Table 5. The PC was formulated to hold the same metabolizable energy, crude protein, lysine and methionine concentration as the NC, however using protein sources of a greater digestibility compared to NC. All diets contained $TiO_2$ as a digestibility marker.

TABLE 5

Composition and chemical analysis of the diets

| Ingredient g/100 g feed | NC | NC + protease | PC |
| --- | --- | --- | --- |
| Corn | 55.73 | 55.73 | 57.79 |
| Soy bean meal | 37.30 | 37.30 | 30.89 |
| Soy protein concentrate | — | — | 4.50 |
| Vegetable oil | 2.00 | 2.00 | 2.00 |
| Limestone | 1.00 | 1.00 | 1.00 |
| Di-calcium phosphate | 1.86 | 1.86 | 1.74 |
| Vitamin premix | 1.00 | 1.00 | 1.00 |
| $TiO_2$ | 0.10 | 0.10 | 0.10 |
| Avatec ® (Coccidiostat) | 0.06 | 0.06 | 0.06 |
| NaCl | 0.50 | 0.50 | 0.50 |
| DL-Methionine | 0.28 | 0.28 | 0.28 |
| Lysine HCl | 0.15 | 0.15 | 0.14 |
| Threonine | 0.01 | 0.01 | — |
| Protease, ppm | — | 15 | — |
| ME, Kcal/kg feed | 3085 | 3085 | 3085 |
| CP | 22.0 | 22.0 | 22.0 |
| D Lysine | 1.19 | 1.19 | 1.19 |
| D Methionine | 0.55 | 0.55 | 0.55 |
| Calcium | 0.90 | 0.90 | 1.18 |
| Phosphorus | 0.75 | 0.75 | 0.73 |
| Phosphorus available | 0.45 | 0.45 | 0.45 |

Data and Sample Collection

Total cage body weight and feed consumption were obtained between days 16 and 21. On day 21 all chickens were sacrificed via cervical dislocation. The chickens were dissected and the content of the terminal ileum were collected. The terminal ileum was defined as 17 cm proximal to a point 2 cm before the ileo-caecal junction as described by Jallier et al. (2003, Influence of the methodology of sampling content from different parts of the ileum on the values of apparent ileal digestibility in broiler chickens, Br. Poult. Sci. 44: 807-809). The ileal digesta were pooled within cage, freeze-dried, and ground for chemical analysis. The crude protein and $TiO_2$ concentration were determined in both digesta and feed samples for later estimation of apparent ileal nitrogen digestibility AIDN (%) which is given in Table 6:

$$AIDN\ (\%)=100-[(CMf/CMe)\times(CNe/CNf)]\times100$$

wherein

CMf=concentration of marker in feed;
CMe=concentration of marker in ileal digesta;
CNf=concentration of nutrient in feed;
CNe=concentration of nutrient in ileal digesta The nitrogen content was determined by a LECO apparatus FP-528 (LECO® Corporation) according to the Dumas method (Dumas, 1831, Procedes de l'Analyse Organique, Ann. Chim. Phys. 247: 198-213). Nitrogen content was transformed to crude protein using a factor of 6.25.

Titanium dioxide concentrations in feed and digesta were determined by inducted coupled plasma (ICP) apparatus ICP-OES 5100 (Agilent Technologies) according to DIN EN ISO 11885:1997 (DIN EN ISO 1998) after $H_2SO_4$ mineralization of the samples.

TABLE 6

AIDN results from in vivo trial in broilers

| Treatment | % apparent ileal nitrogen-digestibility, average |
| --- | --- |
| NC | 75.8 |
| PC | 78.8 |
| Bacillus horneckiae (SEQ ID NO: 1) | 84.2 |

The Bacillus horneckiae protease significantly (P<0.01 compared to NC) increased the apparent ileal nitrogen digestibility compared to both the NC and PC.

Example 9: Ileal Nitrogen Digestibility Trial in Broilers Using the S8 Protease from Bacillus Horneckiae (SEQ ID NO: 1) and a Variant S8 Protease from Bacillus sp.

The trial was run as described in Example 8 and the AIDN results are presented in Table 7 below.

TABLE 7

AIDN results from in vivo trial in broilers

| Treatment | % apparent ileal nitrogen-digestibility, average |
| --- | --- |
| NC | 80.4 |
| PC | 80.5 |
| Bacillus horneckiae (SEQ ID NO: 1) | 83.3 |
| Variant from Bacillus sp. (SEQ ID NO: 3) | 81.9 |

Both the Bacillus horneckiae protease and the protease variant from Bacillus sp. increased the apparent ileal nitrogen digestibility compared to both the NC and PC. In this in vivo trial, the inherent protein digestibility of the feed ingredients was unexpectedly high, meaning that the PC only showed a minimal increase in digestibility compared to the NC. Even so, the proteases still increased the apparent ileal nitrogen digestibility compared to PC, showing that the proteases can work on even good quality diets.

Example 10: Animal Feed and Animal Feed Additives

Granule

The granule is prepared by granulating a protease of the invention with a filler such as sodium sulfate, magnesium sulfate, calcium carbonate and/or cellulose and then optionally coating the granule with a wax coating (e.g., hydrogenated palm oil) or a salt coating (e.g., sodium sulfate and/or magnesium sulfate).

Alternatively, the granule is prepared by absorbing a liquid solution of a protease of the invention onto an inert core and then optionally coating the granule with a wax coating (e.g., hydrogenated palm oil) or a salt coating (e.g., sodium sulfate and/or magnesium sulfate).

Liquid Formulation

A liquid formulation of a protease of the invention comprises 0.1% to 10% w/w enzyme protein, 40-60% glycerol, 0.1 to 0.5% sodium benzoate and water. The liquid formulation is sprayed onto the pelleted animal feed described above or onto mash feed.

Animal Feed Additive

A premix formulation of a protease of the invention containing 0.01 g to 10 g enzyme protein per kilo of premix (optionally formulated as a coated granule) is added to the following premix:

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Examples of Animal Feed

This is an example of a broiler feed comprising the animal feed additive as described above:

62.55% Maize
33.8% Soybean meal (50% crude protein)
1.0% Soybean oil
0.2% DL-Methionine
0.22% DCP (dicalcium phosphate)
0.76% CaCO₃ (calcium carbonate)
0.32% Sand
0.15% NaCl (sodium chloride)
1% of the above animal feed additive (premix).

The ingredients are mixed, and the feed is pelleted at the desired temperature, e.g., 60, 65, 75, 80, 85, 90 or even 95° C.

By way of example only, a feedstuff for chickens, e.g., broiler chickens, may comprise one or more of the ingredients listed in the example percentages given in Table 8.1 below.

TABLE 8.1

Example of broiler diet in starter and finisher phase

| Ingredients | Starter (%) | Finisher (%) |
|---|---|---|
| Maize | 46.2 | 46.7 |
| Wheat middling's | 6.7 | 10.0 |
| Maize DDGS | 7.0 | 7.0 |
| Soybean Meal 48% CP | 32.8 | 26.2 |
| Animal/veg fat blend | 3.0 | 5.8 |
| L-Lysine HCl | 0.3 | 0.3 |
| DL-Methionine | 0.3 | 0.3 |
| L-Threonine | 0.1 | 0.1 |
| Salt | 0.3 | 0.4 |
| Limestone | 1.1 | 1.1 |
| Dicalcium phosphate | 1.2 | 1.2 |
| Vitamin and mineral premix | 0.3 | 0.3 |

By way of example only, the diet specification for chickens, such as broiler chickens, may be as set out as given in Table 8.2 below.

TABLE 8.2

Example of diet specification for chickens in starter and finisher phase

| Diet specification | Starter | Finisher |
|---|---|---|
| Crude protein (%) | 23.00 | 20.40 |
| Metabolizable energy (kcal/kg) | 2950 | 3100 |
| Calcium (%) | 0.85 | 0.85 |
| Available phosphorus (%) | 0.38 | 0.38 |
| Sodium (%) | 0.18 | 0.19 |
| Digestible lysine (%) | 1.21 | 1.07 |
| Digestible methionine (%) | 0.62 | 0.57 |
| Digestible methionine + cysteine (%) | 0.86 | 0.78 |
| Digestible threonine (%) | 0.76 | 0.68 |

By way of example only, a feedstuff for laying hens may comprise one or more of the ingredients listed in the example percentages given in Table 8.3 below.

TABLE 8.3

Example of layer diet in laying phase

| Ingredient | Laying phase (%) |
|---|---|
| Maize | 10.0 |
| Wheat | 53.6 |
| Maize DDGS | 5.0 |
| Soybean meal 48% CP | 14.9 |
| Wheat middling's | 3.0 |
| Soybean oil | 1.8 |
| L-Lysine HCl | 0.2 |
| DL-Methionine | 0.2 |
| L-Threonine | 0.1 |
| Salt | 0.3 |
| Dicalcium phosphate | 1.6 |
| Limestone | 8.9 |
| Vitamin and mineral premix | 0.6 |

By way of example only the diet specification for laying hens may be as set out as given in Table 8.4 below.

TABLE 8.4

Example of diet specification for layers in laying phase

| Diet specification | Laying phase |
|---|---|
| Crude protein (%) | 16.10 |
| Metabolizable energy (kcal/kg) | 2700 |
| Lysine (%) | 0.85 |
| Methionine (%) | 0.42 |
| Methionine + cysteine (%) | 0.71 |
| Threonine (%) | 0.60 |
| Calcium (%) | 3.85 |
| Available phosphorus (%) | 0.42 |
| Sodium (%) | 0.16 |

By way of example only, a feedstuff for turkeys may comprise one or more of the ingredients listed in the example percentages given in Table 8.5 below.

TABLE 8.5

Example of turkey diet in phases 1 to 4

| Ingredient | Phase 1 (%) | Phase 2 (%) | Phase 3 (%) | Phase 4 (%) |
|---|---|---|---|---|
| Wheat | 33.6 | 42.3 | 52.4 | 61.6 |
| Maize DDGS | 7.0 | 7.0 | 7.0 | 7.0 |
| Soybean meal 48% CP | 44.6 | 36.6 | 27.2 | 19.2 |
| Rapeseed meal | 4.0 | 4.0 | 4.0 | 4.0 |
| Soybean oil | 4.4 | 4.2 | 3.9 | 3.6 |
| L-Lysine HCl | 0.5 | 0.5 | 0.4 | 0.4 |
| DL-Methionine | 0.4 | 0.4 | 0.3 | 0.2 |

TABLE 8.5-continued

Example of turkey diet in phases 1 to 4

| Ingredient | Phase 1 (%) | Phase 2 (%) | Phase 3 (%) | Phase 4 (%) |
|---|---|---|---|---|
| L-Threonine | 0.2 | 0.2 | 0.1 | 0.1 |
| Salt | 0.3 | 0.3 | 0.3 | 0.3 |
| Limestone | 1.0 | 1.1 | 1.1 | 1.0 |
| Dicalcium phosphate | 3.5 | 3.0 | 2.7 | 2.0 |
| Vitamin and mineral premix | 0.4 | 0.4 | 0.4 | 0.4 |

By way of example only the diet specification for turkeys may be as set out as given in Table 8.6 below.

TABLE 8.6

Example of diet specification for turkeys in phases 1 to 4

| Diet specification | Phase 1 | Phase 2 | Phase 3 | Phase 4 |
|---|---|---|---|---|
| Crude protein (%) | 29.35 | 26.37 | 22.93 | 20.00 |
| Metabolizable energy (kcal/kg) | 2.850 | 2.900 | 2.950 | 3.001 |
| Calcium (%) | 1.43 | 1.33 | 1.22 | 1.02 |
| Available phosphorus (%) | 0.80 | 0.71 | 0.65 | 0.53 |
| Sodium (%) | 0.16 | 0.17 | 0.17 | 0.17 |
| Digestible lysine (%) | 1.77 | 1.53 | 1.27 | 1.04 |
| Digestible methionine (%) | 0.79 | 0.71 | 0.62 | 0.48 |
| Digestible methionine + cysteine (%) | 1.12 | 1.02 | 0.90 | 0.74 |
| Digestible threonine (%) | 1.03 | 0.89 | 0.73 | 0.59 |

By way of example only, a feedstuff for piglets may comprise one or more of the ingredients listed in the example percentages given in Table 8.7 below.

TABLE 8.7

Example of piglet diet in phases 1 and 2

| Ingredient | Phase 1 (%) | Phase 2 (%) |
|---|---|---|
| Maize | 20.0 | 7.0 |
| Wheat | 25.9 | 46.6 |
| Rye | 4.0 | 10.0 |
| Wheat middling's | 4.0 | 4.0 |
| Maize DDGS | 6.0 | 8.0 |
| Soybean meal 48% CP | 25.7 | 19.9 |
| Dried whey | 10.0 | 0.0 |
| Soybean oil | 1.0 | 0.7 |
| L-Lysine HCl | 0.4 | 0.5 |
| DL-Methionine | 0.2 | 0.2 |
| L-Threonine | 0.1 | 0.2 |
| L-Tryptophan | 0.03 | 0.04 |
| Limestone | 0.6 | 0.7 |
| Dicalcium phosphate | 1.6 | 1.6 |
| Vitamin and mineral premix | 0.2 | 0.2 |
| Salt | 0.2 | 0.4 |

By way of example only the diet specification for piglets may be as set out as given in Table 8.8 below.

TABLE 8.8

Example of diet specification for piglets in phases 1 to 2

| Diet specification | Phase 1 | Phase 2 |
|---|---|---|
| Crude protein (%) | 21.50 | 20.00 |
| Digestible energy (kcal/kg) | 3380 | 3320 |
| Swine net energy (kcal/kg) | 2270 | 2230 |
| Calcium (%) | 0.80 | 0.75 |
| Digestible phosphorus (%) | 0.40 | 0.35 |
| Sodium (%) | 0.20 | 0.20 |

TABLE 8.8-continued

Example of diet specification for piglets in phases 1 to 2

| Diet specification | Phase 1 | Phase 2 |
|---|---|---|
| Digestible lysine (%) | 1.23 | 1.14 |
| Digestible methionine (%) | 0.49 | 0.44 |
| Digigestible methionine + cysteine (%) | 0.74 | 0.68 |
| Digestible threonine (%) | 0.80 | 0.74 |

By way of example only, a feedstuff for grower/finisher pigs may comprise one or more of the ingredients listed in the example percentages given in Table 8.9 below.

TABLE 8.9

Example of grower/finisher diet

| Ingredient | Grower/Finisher (%) |
|---|---|
| Maize | 27.5 |
| Soybean meal 48% CP | 15.4 |
| Maize DDGS | 20.0 |
| Wheat bran | 11.1 |
| Rice bran | 12.0 |
| Canola seed meal | 10.0 |
| Limestone | 1.6 |
| Dicalcium phosphate | 0.01 |
| Salt | 0.4 |
| Vitamin and mineral premix | 0.3 |
| Lysine HCl | 0.2 |
| Vegetable oil | 0.5 |

By way of example only the diet specification for grower/finisher pigs may be as set out as given in Table 8.10 below.

TABLE 8.10

Example of diet specification for grower/finisher pigs

| Diet specification | Grower/Finisher |
|---|---|
| Crude protein (%) | 22.60 |
| Metabolizable energy (kcal/kg) | 3030 |
| Calcium (%) | 0.75 |
| Available phosphorus (%) | 0.29 |
| Digestible lysine (%) | 1.01 |
| Digestible methionine + cysteine (%) | 0.73 |
| Digestible threonine (%) | 0.66 |

Example 11: Apparent Jejunal Nitrogen Digestibility Trial in Broilers for New Proteases Compared to Benchmark (Cibenza)

Animal and Feeding

One day old chickens (Cobb500) obtained from a commercial hatchery (Accouvoir multiplicateur Grelier, La Bohardière, France) were used. The chickens were housed in wire-floor battery cages (0.75 m2/cage, 6 chickens/cage). They were provided with ad libitum access to the feed provided in Table 9 and water until day 7. Birds were weighed on day 7 and allocated to one of the 6 treatments using body weight as the criterion. The same diet was fed to the birds until day 16. The experimental period then ran from 16 to 21 days of chicken life. During the experimental period, birds were fed on either a positive control diet (PC), negative control diet (NC), or NC+test enzyme (Table 9). The test enzymes used in the experiment are SEQ ID NO: 1 (S8, *B. hornechiae*) and SEQ ID NO:3 (S8, *Bacillus* sp-11238)

The enzymes were provided in liquid form and were applied to the treatments by spraying using an ultra-low pressure system coupled with a Forberg F60 mixer. The PC was formulated to provide the same metabolizable energy, crude protein, lysine and methionine concentration as the NC, however it contained protein sources of a greater digestibility compared to NC. All diets contained $TiO_2$ as a digestibility marker.

TABLE 9

Composition and chemical analysis of the diets

| Ingredient g/100 g feed | NC | NC + protease | PC |
|---|---|---|---|
| Corn | 55.73 | 55.73 | 57.79 |
| Soy bean meal | 37.30 | 37.30 | 30.89 |
| Soy protein concentrate | — | — | 4.50 |
| Vegetable oil | 2.00 | 2.00 | 2.00 |
| Limestone | 1.00 | 1.00 | 1.00 |
| Di-calcium phosphate | 1.86 | 1.86 | 1.74 |
| Vitamin premix | 1.00 | 1.00 | 1.00 |
| $TiO_2$ | 0.10 | 0.10 | 0.10 |
| Avatec ® (Coccidiostat) | 0.06 | 0.06 | 0.06 |
| NaCl | 0.50 | 0.50 | 0.50 |
| DL-Methionine | 0.28 | 0.28 | 0.28 |
| Lysine HCl | 0.15 | 0.15 | 0.14 |
| Threonine | 0.01 | 0.01 | — |
| Protease, ppm | — | 15 | — |
| Targeted energy, amino acid and mineral values | | | |
| ME, Kcal/kg feed | 3085 | 3085 | 3085 |
| CP | 22.0 | 22.0 | 22.0 |
| D Lysine | 1.19 | 1.19 | 1.19 |
| D Methionine | 0.55 | 0.55 | 0.55 |
| Calcium | 0.90 | 0.90 | 1.18 |
| Phosphorus | 0.75 | 0.75 | 0.73 |
| Phosphorus availability | 0.45 | 0.45 | 0.45 |

Data and Sample Collection

Average body weight and feed consumption per cage and per treatment were obtained between days 16 and 21. On day 21 all chickens were sacrificed via cervical dislocation. The chickens were dissected and the content of the jejunum were collected. The jejunum was defined as the segment of the small intestine beginning at the end of the pancreatic loop (duodenum) and ending distally at 1 cm proximal to the Meckel's diverticulum. The jejunal digesta were pooled within a cage, freeze-dried, and ground for chemical analysis. The crude protein and $TiO_2$ concentration were determined in both digesta and feed samples for later estimation of apparent jejunal nitrogen digestibility AJDN (%) which is given in Table 10:

$$AJDN\ (\%) = 100 - [(CMf/CMe) \times (CNe/CNf)] \times 100$$

wherein

CMf=concentration of marker in feed;
CMe=concentration of marker in jejunal digesta;
CNf=concentration of nutrient in feed;
CNe=concentration of nutrient in jejunal digesta The nitrogen content was determined using a LECO apparatus FP-528 (LECO® Corporation) according to the Dumas method (Dumas, 1831, Procedes de l'Analyse Organique, Ann. Chim. Phys. 247:198-213). Nitrogen content was transformed to crude protein using a factor of 6.25.

Titanium dioxide concentrations in feed and digesta were determined using an ICP-OES 5100 instrument (Agilent Technologies) according to DIN EN ISO 11885:1997 (DIN EN ISO 1998) after $H_2SO_4$ mineralization of the samples.

TABLE 10

Results of first in vivo trial

| Treatment | % Apparent jejunal nitrogen-digestibility, average |
|---|---|
| NC | 57.88 |
| PC | 60.44 |
| SEQ ID NO: 1 | 62.61 |
| SEQ ID NO: 2 | 61.26 |
| SEQ ID NO: 3 | 62.04 |
| Cibenza | 57.18 |

The results demonstrate that the proteases increased the apparent jejunal nitrogen digestibility compared to both the NC and PC and to the benchmark (Cibenza).

Example 12: Apparent Jejunal Nitrogen Digestibility Trial in Broilers for New Protease Homologs Compared to Benchmark (Cibenza)

Animal and Feeding

One day old chickens (Cobb500) obtained from a commercial hatchery (Accouvoir multiplicateur Grelier, La Bohardière, France) were used. The chickens were housed in wire-floor battery cages (0.75 m2/cage, 6 chickens/cage). They were provided with ad libitum access to feed [What kind of feed?] and water until day 7. Birds were weighed on day 7 and allocated to one of the 8 treatments using body weight as the criterion. A similar diet [Describe diet?] was fed to the birds until day 16. The experimental period then ran from 16 to 21 days of chicken life. During the experimental period, birds were fed on either a positive control diet (PC), negative control diet (NC), or NC+test enzyme (Table 11). The test enzymes used in the experiment were:

| | |
|---|---|
| SEQ ID NO: 5 | S8, *Bacillus* sp-13380 (78% to SEQ ID NO: 1) |
| SEQ ID NO: 6 | S8, *Bacillus idriensis* (80% to SEQ ID NO: 1) |
| SEQ ID NO: 7 | S8, *Bacillus* sp-13380 (89% to SEQ ID NO: 1) |
| SEQ ID NO: 8 | S8, *Bacillus* sp-62451 (90% to SEQ ID NO: 1) |
| SEQ ID NO: 9 | S8, *Bacillus oceanisediminis* (87% SEQ ID NO: 1) |

The enzymes were provided in liquid form and were applied to the treatments by spraying using an ultra-low pressure system coupled with a Forberg F60 mixer. The PC was formulated to provide the same metabolizable energy, crude protein, lysine and methionine concentration as the NC, however it contained protein sources of a greater digestibility compared to NC. All diets contained $TiO_2$ as a digestibility marker.

TABLE 11

Composition and chemical analysis of the diets

| Ingredient g/100 g feed | NC | NC + protease | PC |
|---|---|---|---|
| Corn | 55.73 | 55.73 | 57.79 |
| Soy bean meal | 37.30 | 37.30 | 30.89 |
| Soy protein concentrate | — | — | 4.50 |
| Vegetable oil | 2.00 | 2.00 | 2.00 |
| Limestone | 1.00 | 1.00 | 1.00 |
| Di-calcium phosphate | 1.86 | 1.86 | 1.74 |
| Vitamin premix | 1.00 | 1.00 | 1.00 |
| $TiO_2$ | 0.10 | 0.10 | 0.10 |
| Avatec ® (Coccidiostat) | 0.06 | 0.06 | 0.06 |
| NaCl | 0.50 | 0.50 | 0.50 |
| DL-Methionine | 0.28 | 0.28 | 0.28 |
| Lysine HCl | 0.15 | 0.15 | 0.14 |
| Threonine | 0.01 | 0.01 | — |

TABLE 11-continued

Composition and chemical analysis of the diets

| Ingredient g/100 g feed | NC | NC + protease | PC |
|---|---|---|---|
| Protease, ppm | — | 15 | — |
| Targeted energy, amino acid and mineral values | | | |
| ME, Kcal/kg feed | 3085 | 3085 | 3085 |
| CP | 22.0 | 22.0 | 22.0 |
| D Lysine | 1.19 | 1.19 | 1.19 |
| D Methionine | 0.55 | 0.55 | 0.55 |
| Calcium | 0.90 | 0.90 | 1.18 |
| Phosphorus | 0.75 | 0.75 | 0.73 |
| Phosphorus availability | 0.45 | 0.45 | 0.45 |

Data and Sample Collection

Average body weight and feed consumption per cage and per treatment were obtained between days 16 and 21. On day 21 all chickens were sacrificed via cervical dislocation. The chickens were dissected and the content of the jejunum were collected. The jejunum was defined as the segment of the small intestine beginning at the end of the pancreatic loop (duodenum) and ending distally at 1 cm proximal to the Meckel's diverticulum. The jejunal digesta were pooled within cage, freeze-dried, and ground for chemical analysis. The crude protein and $TiO_2$ concentration were determined in both digesta and feed samples for later estimation of apparent jejunal nitrogen digestibility AJDN (%) which is given in Table 12:

$$AJDN\ (\%) = 100 - [(CMf/CMe) \times (CNe/CNf)] \times 100$$

wherein
CMf=concentration of marker in feed;
CMe=concentration of marker in jejunal digesta;
CNf=concentration of nutrient in feed;
CNe=concentration of nutrient in jejunal digesta The nitrogen content was determined using a LECO apparatus FP-528 (LECO® Corporation) according to the Dumas method (Dumas, J. B. A., Procedes de l'Analyse Organique, Ann. Chim. Phys. 247:198-213 (1831). Nitrogen content was transformed to crude protein using the factor 6.25.

Titanium dioxide concentrations in feed and digesta were determined using an ICP-OES 5100 instrument (Agilent Technologies) according to DIN EN ISO 11885:1997 (DIN EN ISO 1998) after $H_2SO_4$ mineralization of the samples.

TABLE 12

Results of first in vivo trial

| Treatment | % Apparent jejunal nitrogen-digestibility, average |
|---|---|
| NC | 53.50 |
| SEQ ID NO: 5 | 55.67 |
| SEQ ID NO: 7 | 54.23 |
| SEQ ID NO: 6 | 54.14 |
| SEQ ID NO: 9 | 53.83 |
| Cibenza | 53.82 |

The results demonstrate that the proteases increased the apparent jejunal nitrogen digestibility compared to both the NC and to the benchmark (Cibenza)

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Example 12. Activity of 10 PE-Variants of SEQ ID NO: 1 on Feed Relevant Material (SBM/Corn) at pH 7

The proteases are incubated with a SBM-corn slurry at pH 7 at 40° C. under stirring. After incubation the effect of the protease is measured by the OPA method A buffer stock (100 mM succinic acid, 100 mM HEPES, 100 mM CHES, 100 mM CAPS, 12.5 mM $CaCl_2*2H_2O$, 306 mM KCl, 0.01% Triton X-100) is made and adjusted to pH 7.36 with 10M NaOH or 37% HCl. Mixing of 1.4 g milled SBM (soybean meal), 0.6 g milled corn with 20 ml of buffer stock gives a slurry with resulting pH 7. The slurry is premixed for 5 min at room temperature on a magnetic stirrer.

24-well plates (with cross magnets) are placed on a combined heating and stirring device for preheating at 40° C. 2 ml slurry with pH 7 is transferred to each well, and the plate is closed with sealing tape and pre-incubated for 30 min. 100 ul buffer (blank) or enzyme solution is added to the wells (corresponding to 200 mg enzyme/kg feed), the sealing tape is closed and the plates are incubated for 3 hours. The plate is centrifuged for 10 min at 4000 rpm (2500×g) at 0° C. The supernatant is transferred to eppendorf tubes and analyzed using the OPA methodology described above.

All the PE variants tested have higher activity than the wildtype at pH 7 on SBM:corn.

| SEQ ID NO: 1 Variant | Activity (pH 7) | St dev |
|---|---|---|
| S173P, S175P, T297P H390, N59D, L61Y | 2.74 | 0.33 |
| S173P, S175P, T297P H39D, L61P | 2.74 | 0.60 |
| S173P, S175P, T297P I43P, L61P, H123W, V124A | 2.28 | 0.28 |
| S173P, S175P, T297P H39D, N59D, L61Y, H83T | 2.53 | 0.02 |
| S173P, S175P, T297P L61Y, V124A, R130D | 2.79 | 0.50 |
| S173P, S175P, T297P H39D, I43P, N59D, L61Y | 2.79 | 0.35 |
| S173P, S175P, T297P H83T, V124A, R130D | 2.00 | 0.51 |
| S173P, S175P, T297P I43P, L61P, E127N, S129M | 3.03 | 0.10 |
| S173P, S175P, T297P I43P, L61P, V124A, R130D | 1.62 | 0.07 |
| S173P, S175P, T297P I43P, N59D, H123W, V124A | 1.89 | 0.05 |
| (none) SEQ ID NO 1 | 0.85 | 0.04 |

Example 13. SEQ ID NO: 3. In Vitro Data on Feed Relevant Material

Same procedure as above.

| Protease | Activity pH 7 |
|---|---|
| ProAct | 3.27 |
| SEQ ID NO: 3 | 4.25 |

At pH 7, SEQ ID NO: 3 has higher activity on SBM:corn than ProAct®.

Example 14 Cloning and Expression Examples for PE Variants of SEQ ID NO 1

Example 14.1: Construction of Variants by Site-Directed Mutagenesis

Site-directed variants were constructed of the *Bacillus horneckiae* serine protease S8A (SEQ ID NO: 1), comprising specific substitutions according to the invention. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence and can be repeated by everybody skilled in the art.

Mutagenic oligos were designed corresponding to the DNA sequence flanking the desired site(s) of mutation, separated by the DNA base pairs defining the insertions/deletions/substitutions, and purchased from an oligo vendor such as Integrated DNA Technologies (IDT). To test the protease variants of the invention, the mutated DNA comprising a variant of the invention is integrated into a competent *B. subtilis* strain by homologous recombination, fermented using standard protocols (yeast extract based media, 4 days, 30° C.), and screened by activity assay.

Example 14.2: Expression for Activity Assay

The constructed variants were plated on LB agar supplemented with 6 ug/ml chloramphenicol and grown for 37° C. for one day. After growth, colonies were picked to individual wells of standard 24 deep well plates (DWP) containing 3 mL TBgly broth supplemented with 6 ug/ml chloramphenicol and trace metals (50 mM FeCl3, 20 mM $CaCl_2$), 10 mM MnCl2, 10 mM ZnSO4, 2 mM CuCl2, and 2 mM NiCl2, (F. William Studier, "Protein production by auto-induction in high-density shaking cultures", Protein Expression and Purification, 41 (2005) 207-234).

The wild type *Bacillus horneckiae* serine protease S8A, was also inoculated as reference in four wells on each plate. The DWP plates were grown for four days at 30° C. with shaking at 220 rpm. After growth, plates were centrifugated at 2500 rpm for 10 minutes and the supernatants re-gridded in 96-well microtiter plates that were then used for screening for residual activity.

Example 14.3: Fermentation for Purification

Fermentation may be performed by methods well known in the art or as follows. The different *B. subtilis* strains harboring the variants were streaked on LB agar plates and grown overnight at 37° C. The colonies were transferred to 100 ml PS-1 media (PS-1: 100 g/L Sucrose (Danisco cat. no. 109-0429), 40 g/L crust soy (soy bean flour), 10 g/L $Na_2HPO_4.12H_2O$ (Merck cat. no. 6579), 0.1 ml/L replace-Dowfax63N10 (Dow) in 500 ml shake flasks. Cultivation typically takes 4 days at 300° C. shaking with 270 rpm. Cells and other undissolved material were removed from the fermentation broth by centrifugation at 4500 rpm for 20-25 minutes.

Example 15 Assay Description for Screening SEQ ID NO 1 Variants for Improved Gastric Stability Media and Solution
One liter 100 mM Acetate/MES/HEPES/Glycine buffer was composed of 8.2 g Sodium Acetate, 19.5 g MES, 23.8 g HEPES, 7.5 g Glycine. This buffer was supplemented with 1 mL $CaCl_2$ (1M), 50 mL 20% SDS, 1 mL 10% Triton-X and pH adjusted to pH7 with 5N NaOH.

Gastric Challenge Buffer pH3.4 was prepared by mixing of 715 ml of 0.1M Citric Acid and 285 ml of 0,2M $Na_2HPO_4$.

Stop Reagent was composed of 0,2M $Na_2HPO_4$.

Protazyme AK assay plate pH7 were prepared in V bottom Nunc U96PP 0.5 ml 96 well-plates. Hundred Protazyme AK tablets (Megazyme T-PRAK-200T) (around 10.825 g) were dissolved in 200 ml of Acetate/MES/HEPES/Glycine/CaCl2/SDS/Triton-X100 by stirring for 10 minutes at room temperature. 180 µL of this solution was aliquoted into MTP V bottom 96 well plates (Nunc U96PP 0.5 ml) using 8 channel pipet and wide bore tips. Assay plates were sealed and frozen until use.

*Bacillus* broths of SEQ ID NO: 1 variants were aliquoted in two identical grids. Each grid was containing duplicate samples and two reference backbones were also present on each grid of all plates.

Assay Description
The assay was run on a Biomek FXp (Beckman Coulter). The assay was consisting of a pH drop to pH3.4 (gastric challenge) for 10 minutes (primary screening) and 15 minutes (secondary screening made on combined mutations from the primary screening) at 23 C for the different variants of SEQ ID NO: 1. During that incubation time, the backbones stabilities of the different variants were differently affected by the pH drop. Gastric challenge assay was stopped by adding the stop reagent to neutralize the reaction in the challenge grid. To avoid inter plate variations, samples tested for this gastric challenge assay were divided in two grids within on 96 well plate: a control grid, which was not submitted to the pH drop and a challenge grid which was stressed by the pH drop.

The second part of the assay was consisting of revealing the residual activity by an incubation on Protazyme AK pH7 plates after the gastric challenge assay. The Protazyme AK assay was incubated for 15 minutes at 23 C under a 500 rpm shaking. The reaction was stopped by centrifugation and supernatants transferred to a reading spectrophotometer plate. A Residual Activity (RA) ratio was calculated for each variant by calculating the ratio of (Average Absorbance variant from challenge grid)/(Average Absorbance variant from control grid)*100. This RA number was used to rank variants for their improved gastric stability. Two rounds of screening were made: a first round to identify the most promising primary mutations and a second to identify the most stabilized variants made from the combined primary mutations. Absorbance of spectrophotometer plates were analysed at 590 nm.

Example 16 Purification of PE-Variants of Protease

Activity Assay
  Suc-AAPF-pNA assay:
  pNA substrate: Suc-AAPF-pNA (Bachem L-1400).
  Temperature: Room temperature (25° C.)
  Assay buffer: 100 mM succinic acid, 100 mM HEPES, 100 mM CHES, 100 mM CABS, 1 mM $CaCl_2$, 150 mM KCl, 0.01% Triton X-100, pH 9.0.
  20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in OD405 was monitored as a measure of the protease activity.

Purification of SEQ ID NO 1 PE-Variants
The PE-variants were expressed in *B. subtilis*. The culture broth was centrifuged (26000×g, 20 min) and the supernatant was carefully decanted from the precipitate. The supernatant was filtered through a Nalgene 0.2 µm filtration unit to remove the rest of the *Bacillus* host cells. The 0.2 µm filtrate was mixed 1:1 with 3.0M $(NH_4)_2SO_4$ and the mixture was applied to a Phenyl-sepharose FF (high sub) column (from GE Healthcare) equilibrated in 50 mM H₃BO₃, 10 mM MES/NaOH, 2 mM CaCl₂, 1.5M (NH₄)₂SO₄, pH 6.0. After washing the column with the equilibration buffer, the protease was step-eluted with 50 mM H3B03, 10 mM MES, 2 mM CaCl₂, pH 6.0. The eluted peak (containing the protease activity) was collected and applied to a Bacitracin agarose column (from Upfront chromatography) equilibrated in 50 mM H₃BO₃, 10 mM MES, 2 mM CaCl₂, pH 6.0. After washing the column extensively with the equilibration buffer, the protease was eluted with 50 mM H₃BO₃, 10 mM MES, 2 mM CaCl₂, 1M NaCl, pH 6.0 with 25% (v/v) 2-propanol. The elution peak (containing the protease activity) was transferred to 20 mM MES, 2 mM CaCl₂, pH 6.0 on a G25 sephadex column (from GE Healthcare). The G25 transferred peak was the purified preparation and was used for further experiments.

When the purified PE-variant protease preparations were analysed by nonreducing SDS-PAGE and the gel was stained with coomassie, the PE-variant proteases were seen as a major dominant band at approx. 34-37 kDa.

Example 17. In Vivo Broiler Trials

Materials and Methods

Four independent floor pen trials and one cage pen broiler study were performed to evaluate growth performance and apparent ileal digestibility of nitrogen.

Animals and Housing

On the day of arrival (day 1), the chickens (Ross 308/708, Cobb 500) were divided by weight into groups of 18-25 birds. Each group was placed in one floor-pen littered with wood shavings and allocated to one of the different treatments. In the cage pen trail 5 birds have been used per replicate.

Each treatment was replicated with 8-12 groups. The chickens were housed in an environmentally controlled room. The room temperature was adapted to the age of the birds. The birds had free access to feed and water.

Feed Composition, Treatments and Length of Feeding

Feeding phase:
Starter (0-14)
Grower (day 14-28)
Finisher (day 28-35)
Experimental diet with enzyme supplementation: Day 0-35
Feed distribution: Post pelleting or Mash
The enzymes were provided in liquid form and were applied post-pelleting or on mash.
Final volume of the product solution: 300 to 500 ml for –200 kg diet.

The experimental diets (Starter and Grower) were based on maize-soybean meal (see Table below)). The diets were formulated to contain 215-220 g crude protein and 12.9 MJ/kg MEN for the starter period and 190-195 g crude protein and 13.4 MJ/kg MEN for the grower period. The basal diets did contain coccidiostat according to local practice.

| Ingredients (%) | Starter (d 1-14) | Grower (d 14-35) |
|---|---|---|
| Maize 8.0% | 51.30-52.70 | 58.76-60.20 |
| Soy O/C 44% | 38.50-39.70 | 31.00-32.30 |
| Soya Oil | 3.70-3.90 | 4.20-4.50 |
| Premix[1] | 1.00 | 1.00 |
| Others | 2.7-5.5 | 2.0-5.04 |
| Calculated content | | |
| Crude protein (g/kg) | 215-220 | 190-195 |
| Metabolizable energy (MJ/kg)[2] | 12.9 | 13.4 |

[1]Vitamin-mineral premix provided per kilogram of diet: Vitamin A: 10'000 I.U.; vitamin E: 40 IU.; vitamin K3: 3.0 mg; vitamin C: 100 mg; vitamin B1: 2.50 mg; vitamin B2: 8.00 mg; vitamin B6: 5.00 mg; vitamin B12: 0.03 mg; niacin: 50.0 mg; pantothenate calcium: 12.0 mg; folic acid: 1.50 mg; biotin 0.15 mg; cholin: 450 mg; ethoxyquine: 54 mg; Na: 1.17 g; Mg: 0.89; Mn: 80 mg; Fe: 60 mg; Cu: 30 mg; Zn: 54 mg; I: 1.24 mg; Co: 0.6 mg; Se: 0.3 mg The diets were fed either un-supplemented (negative control, C), or supplemented with 1. SEQ ID NO: 1 at 10 mg Enzyme protein per kg feed or
2. SEQ ID NO: 2 at 10 mg Enzyme protein per kg feed or
3. synthetic amino acids in a positive control.

For post pelleting applications, appropriate amount of the liquid preparations of the proteases were diluted in water and sprayed onto the respective pelleted feed to get the final concentrations in the feed corresponding to the different treatments. For procedural balance of all treatments the same volume of water was also sprayed onto the pellets of the control diets.

Experimental Parameters and Analyses

For the experiments, the birds were weighed (as replicate group) on days 1, 24, 28 and 35. The feed consumption for the intermediate periods was determined. Body weight gain and feed conversion ratio (feed/gain) were calculated. In addition, Ileal content were collected at the end of the trial (day 35) for the determination of apparent ileal digestibility of Nitrogen.

RESULTS AND CONCLUSION

The results obtained in the studies showed that the inclusion of the proteases was effective in improving the feed conversion ratio of broilers fed diets. In particular, the results showed that the enzyme treatments consistently improve performance across all tested enzymes of the invention. This consistency and the improvement level is sought after in the industry.

What is claimed is:

1. An animal feed, comprising:
   (a) a granule comprising a core and one or more coatings, wherein the granule comprises an isolated polypeptide having protease activity, said isolated polypeptide selected from the group consisting of polypeptides having at least 85% sequence identity to SEQ ID NO: 1 and polypeptides having at least 85% sequence identity to SEQ ID NO: 2; and
   (b) a protein source;
   wherein said animal feed is a pelleted animal feed.

2. The animal feed of claim 1, wherein the protein source comprises soybean meal.

3. The animal feed of claim 1, further comprising a carbohydrate source.

4. The animal feed of claim 3 wherein the carbohydrate source comprises maize, wheat, and/or rye.

5. The animal feed of claim 1, further comprising a formulating agent selected from the group consisting of glycerol, ethylene glycol, 1,2-propylene glycol, 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, cellulose, and any combination thereof.

6. The animal feed of claim 1, further comprising a vitamin selected from the group consisting of vitamin A, vitamin D3, vitamin E, vitamin K, vitamin C, vitamin B12, biotin, choline, vitamin B1, vitamin B2, vitamin B6, niacin, folic acid, panthothenate, and any combination thereof.

7. The animal feed of claim 1, further comprising a mineral selected from the group consisting of boron, cobalt, chloride, chromium, copper, fluoride, iodine, iron, manganese, molybdenum, iodine, selenium, zinc, calcium, magnesium, phosphorus, potassium, sodium, and any combination thereof.

8. The animal feed of claim 1, further comprising an amino acid selected from the group consisting of lysine, alanine, beta-alanine, threonine, methionine, tryptophan, and any combination thereof.

9. The animal feed of claim 1, wherein the polypeptide has at least 85% sequence identity to SEQ ID NO: 1.

10. The animal feed of claim 1, wherein the polypeptide has at least 90% sequence identity to SEQ ID NO: 1.

11. The animal feed of claim 1, wherein the polypeptide has at least 95% sequence identity to SEQ ID NO: 1.

12. The animal feed of claim 1, wherein the polypeptide has at least 85% sequence identity to SEQ ID NO: 2.

13. The animal feed of claim 1, wherein the polypeptide has at least 90% sequence identity to SEQ ID NO: 2.

14. The animal feed of claim 1, wherein the polypeptide has at least 95% sequence identity to SEQ ID NO: 2.

15. The animal feed of claim 1, wherein the polypeptide comprises SEQ ID NO: 1.

16. The animal feed of claim 1, wherein the polypeptide comprises SEQ ID NO: 2.

17. The animal feed of claim 1, wherein the polypeptide comprises SEQ ID NO: 3.

18. The animal feed of claim 1, wherein the polypeptide is
   a fragment of SEQ ID NO: 1, wherein the fragment has protease activity and comprises at least 283 amino acids of SEQ ID NO: 1; or
   a fragment of SEQ ID NO: 2, wherein the fragment has protease activity and comprises at least 279 amino acids of SEQ ID NO: 2.

19. The animal feed of claim 1, wherein the polypeptide comprises the TGXKV[I/V]XXMSLG motif set forth herein as SEQ ID NO: 4.

20. The animal feed of claim 1, wherein the polypeptide is a variant of SEQ ID NO: 1 or 2, and wherein the variant comprises a set of mutations selected from the group consisting of
   H39D, I43P, N59D, L61Y, S173P, S175P, T297P;
   H39D, N59D, L61P, H83T, S173P, S175P, T297P;
   H39D, N59D, L61P, S173P, S175P, T297P;
   H39D, N59D, L61Y, H83T, S173P, S175P, T297P;
   H39D, N59D, L61Y, S173P, S175P, T297P;
   H39D, N59D, H83T, S173P, S175P, T297P;
   H39D, N59D, E127N, S129M, S173P, S175P, T297P;
   H39D, L61P, S173P, S175P, T297P;
   H39D, L61Y, H83T, S173P, S175P, T297P;
   H39D, L61Y, H123W, V124A, S173P, S175P, T297P;
   H39D, H83T, H123W, V124A, S173P, S175P, T297P;
   H39D, H83T, E127N, S129M, S173P, S175P, T297P;
   I43P, N59D, L61P, H83T, S173P, S175P, T297P;
   I43P, N59D, H123W, V124A, S173P, S175P, T297P;
   I43P, N59D, S173P, S175P, T297P;
   I43P, L61P, H83T, S173P, S175P, T297P;
   I43P, L61P, H123W, V124A, S173P, S175P, T297P;
   I43P, L61P, V124A, R130D, S173P, S175P, T297P;
   I43P, L61P, E127N, S129M, S173P, S175P, T297P;
   I43P, L61P, S173P, S175P, T297P;
   I43P, L61Y, H123W, V124A, S173P, S175P, T297P;
   I43P, L61Y, V124A, R130D, S173P, S175P, T297P;
   I43P, H83T, V124A, R130D, S173P, S175P, T297P;
   N59D, L61P, E127N, S129M, S173P, S175P, T297P;
   N59D, L61Y, H123W, V124A, S173P, S175P, T297P;
   N59D, H83T, H123W, V124A, S173P, S175P, T297P;
   N59D, H83T, S173P, S175P, T297P;
   N59D, E127N, S129M, S173P, S175P, T297P;
   L61P, H83T, E127N, S129M, S173P, S175P, T297P;
   L61P, H83T, S173P, S175P, T297P;
   L61P, H123W, V124A, R130D, S173P, S175P, T297P;
   L61P, V124A, R130D, S173P, S175P, T297P;
   L61P, E127N, S129M, S173P, S175P, T297P;
   L61Y, H83T, E127N, S129M, S173P, S175P, T297P;
   L61Y, H83T, S173P, S175P, T297P;
   L61Y, V124A, R130D, S173P, S175P, T297P;
   L61Y, E127N, S129M, S173P, S175P, T297P;
   H83T, V124A, R130D, S173P, S175P, T297P;
   H83T, E127N, S129M, S173P, S175P, T297P;
   H123W, V124A, R130D, S173P, S175P, T297P; and
   S173P, S175P, T297P;
wherein the positions correspond to the amino acid sequence of SEQ ID NO: 2.

21. The animal feed of claim 1, wherein the polypeptide has at least 95% identity to SEQ ID NO:2 and is a variant comprising one or more substitutions selected from the group consisting of S27K, N109K, S111E, S171E, S173P, G174K, S175P, F180Y, G182A, L184F, Q198E, N199K and T297P, wherein the positions correspond to the amino acid sequence of SEQ ID NO: 2.

22. The animal feed of claim 1, further comprising one or more additional enzymes.

23. A method, comprising administering to an animal the animal feed of claim 1.

24. The method of claim 23, wherein said animal is a chicken.

* * * * *